(12) United States Patent
Taylor et al.

(10) Patent No.: US 12,102,845 B2
(45) Date of Patent: Oct. 1, 2024

(54) ULTRASOUND-BASED NEUROMODULATION SYSTEM

(71) Applicant: ReCor Medical, Inc., Palo Alto, CA (US)

(72) Inventors: Kevin Taylor, San Mateo, CA (US); Jaime Merino, Elmont, NY (US); Paul Chandler, Santa Cruz, CA (US); Jacob Raquet, Los Gatos, CA (US); Isidro M. Gandionco, Fremont, CA (US); Austin R. Roth, San Mateo, CA (US)

(73) Assignee: Recor Medical, Inc., Palo Alto, CA (US)

( * ) Notice: Subject to any disclaimer, the term of this patent is extended or adjusted under 35 U.S.C. 154(b) by 1038 days.

(21) Appl. No.: 16/664,700

(22) Filed: Oct. 25, 2019

(65) Prior Publication Data

US 2020/0121961 A1 Apr. 23, 2020

Related U.S. Application Data

(62) Division of application No. 14/773,285, filed as application No. PCT/US2014/022804 on Mar. 10, 2014, now Pat. No. 10,456,605.

(Continued)

(51) Int. Cl.
*A61N 7/02* (2006.01)
*A61B 17/32* (2006.01)
(Continued)

(52) U.S. Cl.
CPC ...... *A61N 7/022* (2013.01); *A61B 17/320068* (2013.01); *A61B 18/1492* (2013.01);
(Continued)

(58) Field of Classification Search
CPC .. A61N 7/00; A61N 7/022; A61N 2007/0021; A61N 2007/0026;
(Continued)

(56) References Cited

U.S. PATENT DOCUMENTS 3,938,502 A 2/1976 Bom
4,643,186 A 2/1987 Rosen
(Continued)

FOREIGN PATENT DOCUMENTS

DE 20 2005 022 060 U1 11/2012
EP 0 623 360 B1 11/1994
(Continued)

OTHER PUBLICATIONS

Bhatt, et al., A Controlled Trial of Renal Denervation for Resistant Hypertension, N. Engl. J. Med., 370:1393-1401 (2014).
(Continued)

*Primary Examiner* — Ronald Hupczey, Jr.
*Assistant Examiner* — Bradford C. Blaise
(74) *Attorney, Agent, or Firm* — Theresa Ann Raymer

(57) ABSTRACT

A neuromodulation system including a catheter has a balloon along its distal end. An ultrasound transducer positioned within an interior of the balloon can be selectively activated to emit acoustic energy radially outwardly, targeting nerve tissue and other portions of the subject anatomy. Targeted nerve tissue can be heated by the application of ultrasonic energy to neuromodulate the tissue. The system may be delivered over a guidewire. A catheter enhances fluid delivery to a distal end of the catheter while reducing an overall diameter of the catheter. The catheter comprises a guidewire lumen that is eccentric relative to a center axis of the catheter.

38 Claims, 13 Drawing Sheets

Related U.S. Application Data

(60) Provisional application No. 61/814,167, filed on Apr. 19, 2013, provisional application No. 61/784,790, filed on Mar. 14, 2013.

(51) Int. Cl.
  *A61B 18/00* (2006.01)
  *A61B 18/04* (2006.01)
  *A61B 18/14* (2006.01)
  *A61N 7/00* (2006.01)

(52) U.S. Cl.
  CPC .............. *A61B 2018/00023* (2013.01); *A61B 2018/0022* (2013.01); *A61B 2018/00285* (2013.01); *A61B 2018/00404* (2013.01); *A61B 2018/00434* (2013.01); *A61B 2018/00511* (2013.01); *A61B 2018/00577* (2013.01); *A61B 18/04* (2013.01); *A61N 7/00* (2013.01); *A61N 2007/0021* (2013.01); *A61N 2007/003* (2013.01); *A61N 2007/0078* (2013.01)

(58) Field of Classification Search
  CPC ...... A61N 2007/003; A61N 2007/0073; A61N 2007/0078; A61N 17/22004; A61N 17/2202; A61N 17/320068; A61N 17/320069; A61N 2017/22027; A61B 2018/00023; A61B 2018/0022; A61B 2018/00285; A61B 2018/00404; A61B 2018/00434; A61B 2018/00511; A61B 2018/00577; A61B 18/04; A61B 18/1492
  See application file for complete search history.

(56) References Cited

U.S. PATENT DOCUMENTS

| | | | |
|---|---|---|---|
| 4,650,466 A | 3/1987 | Luther |
| 4,709,698 A | 12/1987 | Johnston et al. |
| 4,802,490 A | 2/1989 | Johnston |
| 4,841,977 A | 6/1989 | Griffith et al. |
| 4,983,169 A | 1/1991 | Furukawa |
| 5,000,185 A | 3/1991 | Yock |
| 5,114,423 A | 5/1992 | Kasprzyk |
| 5,295,992 A | 3/1994 | Cameron |
| 5,295,995 A | 3/1994 | Kleiman |
| 5,308,356 A | 5/1994 | Blackshear et al. |
| 5,324,255 A | 6/1994 | Passafaro et al. |
| 5,327,885 A | 7/1994 | Griffith |
| 5,354,220 A | 10/1994 | Ganguly et al. |
| 5,368,591 A | 11/1994 | Lennox |
| 5,391,197 A | 2/1995 | Burdette et al. |
| 5,400,267 A | 3/1995 | Denen et al. |
| 5,423,220 A | 6/1995 | Finsterwald et al. |
| 5,423,811 A | 6/1995 | Imran et al. |
| 5,456,259 A | 10/1995 | Barlow et al. |
| 5,524,491 A | 6/1996 | Cavalloni |
| 5,558,672 A | 9/1996 | Edwards et al. |
| 5,575,788 A | 11/1996 | Baker et al. |
| 5,620,479 A | 4/1997 | Diederich |
| 5,630,837 A | 5/1997 | Crowley |
| 5,657,755 A | 8/1997 | Desai |
| 5,685,839 A | 11/1997 | Edwards et al. |
| 5,688,266 A | 11/1997 | Edwards et al. |
| 5,713,849 A | 2/1998 | Bosma et al. |
| 5,722,397 A | 3/1998 | Eppstein |
| 5,769,812 A | 6/1998 | Stevens et al. |
| 5,775,338 A | 7/1998 | Hastings |
| 5,800,482 A | 9/1998 | Pomeranz et al. |
| 5,803,083 A | 9/1998 | Buck et al. |
| 5,938,645 A | 8/1999 | Gordon |
| 6,066,134 A | 5/2000 | Eggers et al. |
| 6,097,985 A | 8/2000 | Kasevich et al. |
| 6,102,863 A | 8/2000 | Pflugrath et al. |
| 6,117,101 A | 9/2000 | Diederich et al. |
| 6,128,522 A | 10/2000 | Acker et al. |
| 6,149,596 A | 11/2000 | Bancroft |
| 6,190,377 B1 | 2/2001 | Kuzdrall |
| 6,216,704 B1 | 4/2001 | Ingle et al. |
| 6,254,598 B1 | 7/2001 | Edwards |
| 6,277,077 B1 | 8/2001 | Brisken et al. |
| 6,283,989 B1 | 9/2001 | Laufer et al. |
| 6,292,695 B1 | 9/2001 | Webster |
| 6,296,619 B1 | 10/2001 | Brisken et al. |
| 6,299,583 B1 | 10/2001 | Eggers et al. |
| 6,355,030 B1 | 3/2002 | Aldrich et al. |
| 6,383,151 B1 | 5/2002 | Diederich et al. |
| 6,475,146 B1 | 11/2002 | Frelburger et al. |
| 6,492,762 B1 | 12/2002 | Pant et al. |
| 6,514,249 B1 | 2/2003 | Maguire et al. |
| 6,517,534 B1 | 2/2003 | McGovern et al. |
| 6,529,756 B1 | 3/2003 | Phan |
| 6,584,360 B2 | 6/2003 | Francischelli et al. |
| 6,599,256 B1 | 7/2003 | Acker et al. |
| 6,599,288 B2 | 7/2003 | Maguire et al. |
| 6,607,502 B1 | 8/2003 | Maguire et al. |
| 6,635,054 B2 | 10/2003 | Fjield et al. |
| 6,645,202 B1 | 11/2003 | Pless et al. |
| 6,648,883 B2 | 11/2003 | Francischelli et al. |
| 6,669,638 B1 | 12/2003 | Miller et al. |
| 6,669,655 B1 | 12/2003 | Acker |
| 6,692,490 B1 | 2/2004 | Edwards |
| 6,712,767 B2 | 3/2004 | Hossack et al. |
| 6,719,755 B2 | 4/2004 | Sliwa, Jr. et al. |
| 6,740,040 B1 | 5/2004 | Mandrusov et al. |
| 6,763,722 B2 | 7/2004 | Fjield et al. |
| 6,793,635 B2 | 9/2004 | Ryan et al. |
| 6,837,886 B2 | 1/2005 | Collins |
| 6,913,581 B2 | 7/2005 | Corl et al. |
| 6,953,469 B2 | 10/2005 | Ryan |
| 6,954,977 B2 | 10/2005 | Maguire |
| 6,978,174 B2 | 12/2005 | Gelfand et al. |
| 7,052,695 B2 | 5/2006 | Kalish |
| 7,156,816 B2 | 1/2007 | Schwartz et al. |
| 7,162,303 B2 | 1/2007 | Levin et al. |
| 7,285,116 B2 | 10/2007 | de la Rama et al. |
| 7,291,413 B2 | 11/2007 | Allen et al. |
| 7,297,413 B2 | 11/2007 | Mitsumori |
| 7,347,852 B2 | 3/2008 | Hobbs et al. |
| 7,371,231 B2 | 5/2008 | Rioux et al. |
| 7,473,224 B2 | 1/2009 | Makin |
| 7,540,846 B2 | 6/2009 | Harhen et al. |
| 7,573,182 B2 | 8/2009 | Savage |
| 7,591,996 B2 | 9/2009 | Hwang et al. |
| 7,617,005 B2 | 11/2009 | Demarais et al. |
| 7,620,451 B2 | 11/2009 | Demarais et al. |
| 7,621,873 B2 | 11/2009 | Owen et al. |
| 7,625,371 B2 | 12/2009 | Morris et al. |
| 7,647,115 B2 | 1/2010 | Levin et al. |
| 7,653,438 B2 | 1/2010 | Deem et al. |
| 7,678,104 B2 | 3/2010 | Keidar |
| 7,717,948 B2 | 5/2010 | Demarais et al. |
| 7,756,583 B2 | 7/2010 | Demarais et al. |
| 7,837,676 B2 | 11/2010 | Sinelnikov et al. |
| 7,846,317 B2 | 12/2010 | Meltzer et al. |
| 7,873,417 B2 | 1/2011 | Demarais et al. |
| 7,937,143 B2 | 5/2011 | Demarais et al. |
| 7,942,871 B2 | 5/2011 | Thapliyal et al. |
| 8,024,050 B2 | 9/2011 | Libbus et al. |
| 8,025,688 B2 | 9/2011 | Diederich et al. |
| 8,131,371 B2 | 3/2012 | Demarals et al. |
| 8,137,274 B2 | 3/2012 | Weng et al. |
| 8,233,221 B2 | 7/2012 | Suijver et al. |
| 8,251,986 B2 | 8/2012 | Chornenky et al. |
| 8,287,472 B2 | 10/2012 | Ostrovsky et al. |
| 8,447,414 B2 | 5/2013 | Johnson et al. |
| 8,475,442 B2 | 7/2013 | Hall et al. |
| 8,483,831 B1 | 7/2013 | Hiavka et al. |
| 8,485,993 B2 | 7/2013 | Orszulak et al. |
| 8,504,147 B2 | 8/2013 | Deem et al. |
| D697,036 S | 1/2014 | Kay et al. |
| 8,626,300 B2 | 1/2014 | Demarais et al. |
| 8,702,619 B2 | 4/2014 | Wang |
| 8,715,209 B2 | 5/2014 | Gertner |

(56) References Cited

U.S. PATENT DOCUMENTS

| | | |
|---|---|---|
| 8,734,438 B2 | 5/2014 | Behnke |
| D708,810 S | 7/2014 | Lewis, Jr. |
| 8,774,913 B2 | 7/2014 | Demarais et al. |
| 8,790,281 B2 | 7/2014 | Diederich et al. |
| 8,808,345 B2 | 8/2014 | Clark et al. |
| 8,818,514 B2 | 8/2014 | Zarins et al. |
| D712,352 S | 9/2014 | George et al. |
| D712,353 S | 9/2014 | George et al. |
| D712,833 S | 9/2014 | George et al. |
| 8,845,629 B2 | 9/2014 | Demarais et al. |
| 8,932,289 B2 | 1/2015 | Mayse et al. |
| 8,974,445 B2 | 3/2015 | Warnking et al. |
| 9,022,948 B2 | 5/2015 | Wang |
| 9,028,472 B2 | 5/2015 | Mathur et al. |
| 9,066,720 B2 | 6/2015 | Ballakur et al. |
| 9,072,902 B2 | 7/2015 | Mathur et al. |
| 9,155,590 B2 | 10/2015 | Mathur |
| 9,186,198 B2 | 11/2015 | Demarais et al. |
| 9,186,212 B2 | 11/2015 | Nabulovsky et al. |
| 9,289,132 B2 | 3/2016 | Ghaffari |
| 9,326,816 B2 | 5/2016 | Srivastava |
| 9,327,123 B2 | 5/2016 | Yamasaki |
| 9,333,035 B2 | 5/2016 | Rudie |
| 9,339,332 B2 | 5/2016 | Srivastava |
| 9,345,530 B2 | 5/2016 | Ballakur et al. |
| 9,375,154 B2 | 6/2016 | Wang |
| 9,427,579 B2 | 8/2016 | Fain et al. |
| 9,439,598 B2 | 9/2016 | Shimada et al. |
| 9,649,064 B2 | 5/2017 | Toth et al. |
| 9,675,413 B2 | 6/2017 | Deem et al. |
| 9,700,372 B2 | 7/2017 | Schaer |
| 9,707,034 B2 | 7/2017 | Schaer |
| 9,723,998 B2 | 8/2017 | Wang |
| 9,730,639 B2 | 8/2017 | Toth et al. |
| 9,743,845 B2 | 8/2017 | Wang |
| 9,750,560 B2 | 9/2017 | Ballakur et al. |
| 9,770,291 B2 | 9/2017 | Wang et al. |
| 9,770,593 B2 | 9/2017 | Gross |
| 9,801,684 B2 | 10/2017 | Fain |
| 9,820,811 B2 | 11/2017 | Wang |
| 9,907,983 B2 | 3/2018 | Thapliyal et al. |
| 9,931,047 B2 | 4/2018 | Srivastava |
| 9,943,666 B2 | 4/2018 | Warnking |
| 9,956,034 B2 | 5/2018 | Toth et al. |
| 9,968,790 B2 | 5/2018 | Toth et al. |
| 9,981,108 B2 | 5/2018 | Warnking |
| 9,999,463 B2 | 6/2018 | Puryear et al. |
| 10,004,458 B2 | 6/2018 | Toth et al. |
| 10,004,557 B2 | 6/2018 | Gross et al. |
| 10,010,364 B2 | 7/2018 | Harringtpm |
| 10,016,233 B2 | 7/2018 | Pike |
| 10,022,085 B2 | 7/2018 | Toth et al. |
| 10,039,901 B2 | 8/2018 | Warnking |
| 10,123,903 B2 | 11/2018 | Warnking et al. |
| 10,143,419 B2 | 12/2018 | Toth et al. |
| 10,179,020 B2 | 1/2019 | Ballakur et al. |
| 10,179,026 B2 | 1/2019 | Ng |
| 10,182,865 B2 | 1/2019 | Naga et al. |
| 10,226,633 B2 | 3/2019 | Toth et al. |
| 10,245,429 B2 | 4/2019 | Deem et al. |
| 10,292,610 B2 | 5/2019 | Srivastava |
| 10,293,190 B2 | 5/2019 | Zarins et al. |
| 10,363,359 B2 | 7/2019 | Toth et al. |
| 10,368,775 B2 | 8/2019 | Hettrick et al. |
| 10,376,310 B2 | 8/2019 | Fain et al. |
| 10,383,685 B2 | 8/2019 | Gross et al. |
| 10,398,332 B2 | 9/2019 | Min et al. |
| 10,470,684 B2 | 11/2019 | Toth et al. |
| 10,478,249 B2 | 11/2019 | Gross et al. |
| 10,499,937 B2 | 12/2019 | Warnking |
| 10,543,037 B2 | 1/2020 | Shah |
| 10,850,091 B2 | 12/2020 | Zarins et al. |
| 11,801,085 B2 | 10/2023 | Wu et al. |
| 2001/0007940 A1 | 7/2001 | Tu et al. |
| 2001/0023365 A1 | 9/2001 | Medhkour et al. |
| 2002/0002334 A1 | 1/2002 | Okuno et al. |
| 2002/0002371 A1 | 1/2002 | Acker et al. |
| 2002/0022833 A1 | 2/2002 | Maguire et al. |
| 2002/0042610 A1 | 4/2002 | Sliwa, Jr. et al. |
| 2002/0062123 A1 | 5/2002 | McClurken et al. |
| 2002/0065512 A1 | 5/2002 | Fjield et al. |
| 2002/0072741 A1 | 6/2002 | Sliwa, Jr. et al. |
| 2002/0087156 A1 | 7/2002 | Maguire et al. |
| 2002/0150693 A1 | 10/2002 | Kobayashi et al. |
| 2002/0151889 A1 | 10/2002 | Swanson et al. |
| 2002/0156469 A1 | 10/2002 | Yon et al. |
| 2002/0165535 A1 | 11/2002 | Lesh |
| 2002/0173724 A1 | 11/2002 | Dorando et al. |
| 2002/0193681 A1 | 12/2002 | Vitek et al. |
| 2002/0193781 A1 | 12/2002 | Loeb |
| 2003/0004439 A1 | 1/2003 | Pant et al. |
| 2003/0028111 A1 | 2/2003 | Vaezy et al. |
| 2003/0060813 A1 | 3/2003 | Loeb et al. |
| 2003/0074039 A1 | 4/2003 | Puskas |
| 2003/0125726 A1* | 7/2003 | Maguire ............... A61N 7/02 606/41 |
| 2003/0138571 A1 | 7/2003 | Kunishi et al. |
| 2003/0181963 A1 | 9/2003 | Pellegrino et al. |
| 2003/0204138 A1 | 10/2003 | Choi |
| 2003/0216721 A1 | 11/2003 | Diederich et al. |
| 2003/0216792 A1 | 11/2003 | Levin |
| 2003/0216794 A1 | 11/2003 | Becker et al. |
| 2003/0225331 A1 | 12/2003 | Diederich et al. |
| 2003/0233099 A1 | 12/2003 | Danaek et al. |
| 2004/0019349 A1 | 1/2004 | Fuimaono et al. |
| 2004/0044286 A1 | 3/2004 | Hossack et al. |
| 2004/0082859 A1 | 4/2004 | Schaer |
| 2004/0097819 A1 | 5/2004 | Duarte |
| 2004/0106880 A1 | 6/2004 | Weng et al. |
| 2004/0122494 A1 | 6/2004 | Eggers et al. |
| 2004/0167415 A1 | 8/2004 | Gelfand et al. |
| 2004/0181178 A1 | 9/2004 | Aldrich et al. |
| 2004/0230116 A1 | 11/2004 | Cowan et al. |
| 2004/0242999 A1 | 12/2004 | Vitek et al. |
| 2004/0253450 A1 | 12/2004 | Seita et al. |
| 2005/0009218 A1 | 1/2005 | Kunihiro |
| 2005/0035901 A1 | 2/2005 | Lyon |
| 2005/0038340 A1 | 2/2005 | Vaezy et al. |
| 2005/0159738 A1 | 7/2005 | Visram et al. |
| 2005/0203501 A1 | 9/2005 | Aldrich et al. |
| 2005/0215990 A1 | 9/2005 | Govari |
| 2005/0228283 A1 | 10/2005 | Gifford et al. |
| 2005/0228459 A1 | 10/2005 | Levin et al. |
| 2005/0228460 A1 | 10/2005 | Levin et al. |
| 2005/0234523 A1 | 10/2005 | Levin et al. |
| 2005/0256518 A1 | 11/2005 | Rama et al. |
| 2005/0261672 A1 | 11/2005 | Deem et al. |
| 2005/0288730 A1 | 12/2005 | Deem |
| 2006/0041277 A1 | 2/2006 | Deem et al. |
| 2006/0052695 A1 | 3/2006 | Adam et al. |
| 2006/0058711 A1 | 3/2006 | Harhen et al. |
| 2006/0064081 A1 | 3/2006 | Rosinko |
| 2006/0088705 A1 | 4/2006 | Mitsumori |
| 2006/0100514 A1 | 5/2006 | Lopath |
| 2006/0118127 A1 | 6/2006 | Chinn |
| 2006/0121200 A1 | 6/2006 | Halpert et al. |
| 2006/0142827 A1 | 6/2006 | Willard et al. |
| 2006/0154072 A1 | 7/2006 | Schlossman et al. |
| 2006/0155269 A1 | 7/2006 | Warnking |
| 2006/0184069 A1 | 8/2006 | Vaitekunas |
| 2006/0184072 A1 | 8/2006 | Manna |
| 2006/0212076 A1 | 9/2006 | Demarais et al. |
| 2006/0212078 A1 | 9/2006 | Demarais et al. |
| 2006/0217772 A1 | 9/2006 | Libbus et al. |
| 2006/0229594 A1 | 10/2006 | Francischelli et al. |
| 2006/0235286 A1 | 10/2006 | Stone et al. |
| 2006/0241523 A1 | 10/2006 | Sinelnikov et al. |
| 2006/0265014 A1 | 11/2006 | Demarais et al. |
| 2006/0265015 A1 | 11/2006 | Demarais et al. |
| 2006/0270976 A1 | 11/2006 | Savage et al. |
| 2006/0276852 A1 | 12/2006 | Demarais et al. |
| 2007/0060921 A1 | 3/2007 | Janssen et al. |
| 2007/0072741 A1 | 3/2007 | Robideau |
| 2007/0106292 A1 | 5/2007 | Kaplan |

(56) References Cited

U.S. PATENT DOCUMENTS

| | | |
|---|---|---|
| 2007/0124458 A1 | 5/2007 | Kumar |
| 2007/0129720 A1 | 6/2007 | Demarais et al. |
| 2007/0129760 A1 | 6/2007 | Demarais et al. |
| 2007/0135875 A1 | 6/2007 | Demarais et al. |
| 2007/0173899 A1 | 7/2007 | Levin et al. |
| 2007/0175359 A1 | 8/2007 | Hwang |
| 2007/0203547 A1 | 8/2007 | Costello et al. |
| 2007/0203549 A1 | 8/2007 | Demarais et al. |
| 2007/0249046 A1 | 10/2007 | Shields, Jr. |
| 2007/0255267 A1 | 11/2007 | Diederich et al. |
| 2007/0255342 A1 | 11/2007 | Laufer |
| 2007/0265609 A1 | 11/2007 | Thapliyal et al. |
| 2007/0265610 A1 | 11/2007 | Thapliyal et al. |
| 2007/0265687 A1 | 11/2007 | Deem et al. |
| 2007/0282407 A1 | 12/2007 | Demarais et al. |
| 2007/0293762 A1 | 12/2007 | Sawada et al. |
| 2008/0039746 A1 | 2/2008 | Hissong et al. |
| 2008/0052186 A1 | 2/2008 | Walker et al. |
| 2008/0151001 A1 | 6/2008 | Sudo et al. |
| 2008/0215031 A1* | 9/2008 | Belfort ............ A61B 17/12099 606/192 |
| 2008/0252172 A1 | 10/2008 | Yetter et al. |
| 2008/0255449 A1 | 10/2008 | Warnking et al. |
| 2008/0255478 A1 | 10/2008 | Burdette |
| 2008/0255642 A1 | 10/2008 | Zarins et al. |
| 2009/0024195 A1 | 1/2009 | Rezai et al. |
| 2009/0036948 A1 | 2/2009 | Levin et al. |
| 2009/0062873 A1 | 3/2009 | Wu et al. |
| 2009/0076409 A1 | 3/2009 | Wu et al. |
| 2009/0118125 A1 | 5/2009 | Kobayashi et al. |
| 2009/0118725 A1 | 5/2009 | Auth et al. |
| 2009/0124964 A1 | 5/2009 | Leach et al. |
| 2009/0149753 A1 | 6/2009 | Govari et al. |
| 2009/0171202 A1 | 7/2009 | Kirkpatrick et al. |
| 2009/0189485 A1 | 7/2009 | Iyoki |
| 2009/0204006 A1 | 8/2009 | Wakabayashi et al. |
| 2009/0221939 A1 | 9/2009 | Demarais et al. |
| 2009/0228003 A1 | 9/2009 | Sinelnikov |
| 2009/0234407 A1 | 9/2009 | Hastings et al. |
| 2009/0248005 A1 | 10/2009 | Rusin et al. |
| 2009/0248011 A1 | 10/2009 | Hlavka et al. |
| 2009/0299360 A1 | 12/2009 | Ormsby |
| 2009/0312673 A1 | 12/2009 | Thapliyal et al. |
| 2009/0312693 A1 | 12/2009 | Thapliyal et al. |
| 2009/0312755 A1 | 12/2009 | Thapliyal et al. |
| 2010/0016762 A1 | 1/2010 | Thapliyal et al. |
| 2010/0033940 A1 | 2/2010 | Yamaguchi et al. |
| 2010/0049099 A1 | 2/2010 | Thapliyal et al. |
| 2010/0113928 A1 | 5/2010 | Thapliyal et al. |
| 2010/0113985 A1 | 5/2010 | Thapliyal et al. |
| 2010/0114094 A1 | 5/2010 | Thapliyal et al. |
| 2010/0125198 A1 | 5/2010 | Thapliyal et al. |
| 2010/0130892 A1 | 5/2010 | Warnking |
| 2010/0137860 A1 | 6/2010 | Demarais et al. |
| 2010/0137952 A1 | 6/2010 | Demarais et al. |
| 2010/0152582 A1 | 6/2010 | Thapliyal et al. |
| 2010/0168731 A1 | 7/2010 | Wu et al. |
| 2010/0168737 A1 | 7/2010 | Grunewald |
| 2010/0168739 A1 | 7/2010 | Wu et al. |
| 2010/0174282 A1 | 7/2010 | Demarais et al. |
| 2010/0179424 A1 | 7/2010 | Warnking et al. |
| 2010/0189974 A1 | 7/2010 | Ochi et al. |
| 2010/0191112 A1 | 7/2010 | Demarais et al. |
| 2010/0198065 A1 | 8/2010 | Thapliyal et al. |
| 2010/0249859 A1 | 9/2010 | Dilorenzo |
| 2010/0291722 A1 | 11/2010 | Kim |
| 2011/0004184 A1 | 1/2011 | Proksch et al. |
| 2011/0060324 A1 | 3/2011 | Wu et al. |
| 2011/0087096 A1 | 4/2011 | Behar |
| 2011/0087097 A1 | 4/2011 | Behar |
| 2011/0104060 A1 | 5/2011 | Seward |
| 2011/0112400 A1 | 5/2011 | Emery et al. |
| 2011/0118598 A1 | 5/2011 | Gertner |
| 2011/0118723 A1 | 5/2011 | Turner et al. |
| 2011/0125206 A1 | 5/2011 | Bornzin |
| 2011/0137298 A1 | 6/2011 | Nguyen et al. |
| 2011/0172527 A1 | 7/2011 | Gertner |
| 2011/0178516 A1 | 7/2011 | Orszulak et al. |
| 2011/0200171 A1 | 8/2011 | Beetel et al. |
| 2011/0208096 A1 | 8/2011 | Demarais et al. |
| 2011/0257523 A1 | 10/2011 | Hastings et al. |
| 2011/0257562 A1 | 10/2011 | Schaer |
| 2011/0257563 A1 | 10/2011 | Thapliyal et al. |
| 2011/0257564 A1 | 10/2011 | Demarais et al. |
| 2011/0301662 A1 | 12/2011 | Bar-Yoseph et al. |
| 2011/0319765 A1 | 12/2011 | Gertner et al. |
| 2012/0004656 A1 | 1/2012 | Jackson et al. |
| 2012/0065493 A1 | 3/2012 | Gertner |
| 2012/0065554 A1 | 3/2012 | Pikus |
| 2012/0078278 A1 | 3/2012 | Bales et al. |
| 2012/0095461 A1 | 4/2012 | Herscher et al. |
| 2012/0123243 A1 | 5/2012 | Hastings |
| 2012/0123303 A1 | 5/2012 | Sogard et al. |
| 2012/0143097 A1 | 6/2012 | Pike, Jr. |
| 2012/0165667 A1 | 6/2012 | Altmann et al. |
| 2012/0172723 A1 | 7/2012 | Gertner |
| 2012/0215106 A1 | 8/2012 | Sverdlik et al. |
| 2012/0232436 A1 | 9/2012 | Warnking |
| 2012/0238918 A1 | 9/2012 | Gertner |
| 2012/0238919 A1 | 9/2012 | Gertner |
| 2012/0265198 A1 | 10/2012 | Crow et al. |
| 2012/0296232 A1 | 11/2012 | Ng |
| 2012/0316439 A1 | 12/2012 | Behar |
| 2013/0012844 A1 | 1/2013 | Demarais et al. |
| 2013/0023897 A1 | 1/2013 | Wallace |
| 2013/0072928 A1 | 3/2013 | Schaer |
| 2013/0085489 A1 | 4/2013 | Fain et al. |
| 2013/0090650 A1 | 4/2013 | Jenson et al. |
| 2013/0096550 A1 | 4/2013 | Hill |
| 2013/0103064 A1 | 4/2013 | Arenson et al. |
| 2013/0110012 A1 | 5/2013 | Gertner |
| 2013/0116737 A1 | 5/2013 | Edwards et al. |
| 2013/0123770 A1* | 5/2013 | Smith ................ A61N 7/022 606/28 |
| 2013/0131668 A1 | 5/2013 | Schaer |
| 2013/0131743 A1 | 5/2013 | Yamasaki et al. |
| 2013/0138018 A1 | 5/2013 | Gertner |
| 2013/0150749 A1 | 6/2013 | McLean et al. |
| 2013/0158441 A1 | 6/2013 | Demarais et al. |
| 2013/0158442 A1 | 6/2013 | Demarais et al. |
| 2013/0165822 A1 | 6/2013 | Demarais et al. |
| 2013/0165924 A1 | 6/2013 | Mathur et al. |
| 2013/0165925 A1 | 6/2013 | Mathur et al. |
| 2013/0172872 A1* | 7/2013 | Subramaniam .... A61B 18/1492 606/33 |
| 2013/0197555 A1 | 8/2013 | Schaer |
| 2013/0204167 A1 | 8/2013 | Sverdlik et al. |
| 2013/0211396 A1 | 8/2013 | Sverdlik et al. |
| 2013/0211437 A1 | 8/2013 | Sverdlik et al. |
| 2013/0218054 A1 | 8/2013 | Sverdlik et al. |
| 2013/0274614 A1 | 10/2013 | Shimada et al. |
| 2013/0274658 A1 | 10/2013 | Steinke et al. |
| 2013/0282084 A1 | 10/2013 | Mathur et al. |
| 2013/0289369 A1 | 10/2013 | Margolis |
| 2013/0289682 A1 | 10/2013 | Barman et al. |
| 2013/0304047 A1 | 11/2013 | Grunewald et al. |
| 2013/0331739 A1 | 12/2013 | Gertner |
| 2014/0012133 A1 | 1/2014 | Sverdlik et al. |
| 2014/0018788 A1 | 1/2014 | Engelman et al. |
| 2014/0018794 A1 | 1/2014 | Anderson et al. |
| 2014/0025069 A1 | 1/2014 | Willard et al. |
| 2014/0031727 A1 | 1/2014 | Warnking |
| 2014/0039477 A1 | 2/2014 | Sverdlik et al. |
| 2014/0046313 A1 | 2/2014 | Pederson et al. |
| 2014/0058294 A1* | 2/2014 | Gross ................ A61B 5/4836 601/2 |
| 2014/0067029 A1 | 3/2014 | Schauer et al. |
| 2014/0074083 A1 | 3/2014 | Horn et al. |
| 2014/0107639 A1 | 4/2014 | Zhang et al. |
| 2014/0163540 A1 | 6/2014 | Iyer et al. |
| 2014/0180196 A1 | 6/2014 | Stone et al. |
| 2014/0180197 A1 | 6/2014 | Sverdlik et al. |
| 2014/0194785 A1 | 7/2014 | Gertner |
| 2014/0200489 A1 | 7/2014 | Behar et al. |

(56) References Cited

U.S. PATENT DOCUMENTS

| | | |
|---|---|---|
| 2014/0214018 A1 | 7/2014 | Behar et al. |
| 2014/0249524 A1 | 9/2014 | Kocur |
| 2014/0257271 A1* | 9/2014 | Mayse .............. A61B 18/1492 606/41 |
| 2014/0272110 A1 | 9/2014 | Taylor et al. |
| 2014/0274614 A1 | 9/2014 | Min et al. |
| 2014/0275924 A1 | 9/2014 | Min et al. |
| 2014/0276742 A1 | 9/2014 | Nabutovsky et al. |
| 2014/0276752 A1 | 9/2014 | Wang et al. |
| 2014/0276755 A1 | 9/2014 | Cao et al. |
| 2014/0276789 A1 | 9/2014 | Dandler et al. |
| 2014/0277033 A1 | 9/2014 | Taylor et al. |
| 2014/0288551 A1 | 9/2014 | Bharmi et al. |
| 2014/0288616 A1 | 9/2014 | Rawat et al. |
| 2014/0303617 A1 | 10/2014 | Shimada |
| 2015/0223877 A1 | 8/2015 | Behar et al. |
| 2015/0289931 A1 | 10/2015 | Puryear et al. |
| 2015/0290427 A1 | 10/2015 | Warnking |
| 2015/0335919 A1 | 11/2015 | Behar et al. |
| 2016/0000345 A1 | 1/2016 | Kobayashi et al. |
| 2016/0008635 A1* | 1/2016 | Burdette .............. B06B 1/0625 601/3 |
| 2016/0016016 A1 | 1/2016 | Taylor et al. |
| 2016/0045121 A1 | 2/2016 | Akingba et al. |
| 2017/0027460 A1 | 2/2017 | Shimada et al. |
| 2017/0035310 A1 | 2/2017 | Shimada et al. |
| 2017/0296264 A1 | 10/2017 | Wang |
| 2018/0022108 A1 | 1/2018 | Mori et al. |
| 2018/0042670 A1 | 2/2018 | Wang et al. |
| 2018/0064359 A1 | 3/2018 | Pranaitis |
| 2018/0078307 A1 | 3/2018 | Wang et al. |
| 2018/0185091 A1 | 7/2018 | Toth et al. |
| 2018/0221087 A1 | 8/2018 | Puryear et al. |
| 2018/0249958 A1 | 9/2018 | Toth et al. |
| 2018/0250054 A1 | 9/2018 | Gross et al. |
| 2018/0280082 A1 | 10/2018 | Puryear et al. |
| 2018/0289320 A1 | 10/2018 | Toth et al. |
| 2018/0310991 A1 | 11/2018 | Pike |
| 2018/0333204 A1 | 11/2018 | Ng |
| 2019/0046111 A1 | 2/2019 | Toth et al. |
| 2019/0046264 A1 | 2/2019 | Toth et al. |
| 2019/0076191 A1 | 3/2019 | Wang |
| 2019/0110704 A1 | 4/2019 | Wang |
| 2019/0134396 A1 | 5/2019 | Toth et al. |
| 2019/0151670 A1 | 5/2019 | Toth et al. |
| 2019/0183560 A1 | 6/2019 | Ballakur et al. |
| 2019/0307361 A1 | 10/2019 | Hettrick et al. |
| 2020/0046248 A1 | 2/2020 | Toth et al. |
| 2020/0077907 A1 | 3/2020 | Shimada et al. |

FOREIGN PATENT DOCUMENTS

| | | |
|---|---|---|
| EP | 0 659 387 A2 | 6/1995 |
| EP | 0 767 630 B1 | 4/1997 |
| EP | 0 774 276 A2 | 5/1997 |
| EP | 0 838 980 A2 | 4/1998 |
| EP | 1 042 990 A1 | 10/2000 |
| EP | 1 100 375 B1 | 5/2001 |
| EP | 1 384 445 A1 | 1/2004 |
| EP | 1579889 | 9/2005 |
| EP | 1 598 024 A2 | 11/2005 |
| EP | 1 647 305 B1 | 4/2006 |
| EP | 2 218 479 A2 | 8/2010 |
| EP | 2359764 | 8/2011 |
| EP | 2430996 | 3/2012 |
| EP | 2 457 614 A1 | 5/2012 |
| EP | 2 460 486 B1 | 6/2012 |
| EP | 2 495 012 A1 | 9/2012 |
| EP | 1503685 | 10/2012 |
| EP | 2 521 593 B1 | 11/2012 |
| EP | 2 561 903 A1 | 2/2013 |
| EP | 2 561 905 A1 | 2/2013 |
| EP | 1299035 | 2/2013 |
| EP | 2 626 022 A2 | 8/2013 |
| EP | 2 632 373 | 9/2013 |
| EP | 2 662 041 A2 | 11/2013 |
| EP | 2 662 043 A2 | 11/2013 |
| EP | 2968984 | 8/2016 |
| EP | 2995250 | 10/2019 |
| EP | 3799931 | 4/2021 |
| GB | 2 037 166 A | 7/1980 |
| JP | 07-178173 A | 7/1995 |
| JP | 10-127678 A | 5/1998 |
| JP | 11-218100 A | 8/1999 |
| JP | 2000-054153 A | 2/2000 |
| JP | 2002-078809 A | 3/2002 |
| JP | 2005-526579 A | 9/2005 |
| JP | 2008-515544 A | 5/2008 |
| JP | 2010-503466 A1 | 2/2010 |
| WO | WO-90/00420 A1 | 1/1990 |
| WO | WO-92/07622 A1 | 5/1992 |
| WO | WO-92/20291 A1 | 11/1992 |
| WO | WO-94/05365 A1 | 3/1994 |
| WO | WO-94/11057 A1 | 5/1994 |
| WO | WO-95/19143 A1 | 7/1995 |
| WO | WO-95/25472 A1 | 9/1995 |
| WO | WO-96/00039 A1 | 1/1996 |
| WO | WO-97/13463 A1 | 4/1997 |
| WO | WO-97/36548 A1 | 10/1997 |
| WO | WO-98/41178 A1 | 9/1998 |
| WO | WO-98/42403 A1 | 10/1998 |
| WO | WO-98/49957 A1 | 11/1998 |
| WO | WO-98/52465 A1 | 11/1998 |
| WO | WO-99/02096 A1 | 1/1999 |
| WO | WO 9902096 | 1/1999 |
| WO | WO-99/35987 A1 | 7/1999 |
| WO | WO-99/44519 A2 | 9/1999 |
| WO | WO-99/44523 A1 | 9/1999 |
| WO | WO-99/52423 A1 | 10/1999 |
| WO | WO-99/56812 A2 | 11/1999 |
| WO | WO-00/16850 A1 | 3/2000 |
| WO | WO-00/27292 A1 | 5/2000 |
| WO | WO-00/41881 A2 | 7/2000 |
| WO | WO-00/42934 A1 | 7/2000 |
| WO | WO-00/51511 A1 | 9/2000 |
| WO | WO-00/51683 A1 | 9/2000 |
| WO | WO-00/56237 A2 | 9/2000 |
| WO | WO-00/57495 A1 | 9/2000 |
| WO | WO-00/67648 A1 | 11/2000 |
| WO | WO-00/67656 A1 | 11/2000 |
| WO | WO-00/67659 A1 | 11/2000 |
| WO | WO-00/67830 A1 | 11/2000 |
| WO | WO-00/67832 A2 | 11/2000 |
| WO | WO-01/13357 A1 | 2/2001 |
| WO | WO-01/22897 A1 | 4/2001 |
| WO | WO-01/37925 A2 | 5/2001 |
| WO | WO-01/70114 A1 | 9/2001 |
| WO | WO-01/80723 A2 | 11/2001 |
| WO | WO-01/82814 A2 | 11/2001 |
| WO | WO 01/95820 | 12/2001 |
| WO | WO-02/05868 A2 | 1/2002 |
| WO | WO 02/005897 | 1/2002 |
| WO | WO 2002/019934 | 3/2002 |
| WO | WO-02/083196 A2 | 10/2002 |
| WO | WO-02/085192 A2 | 10/2002 |
| WO | WO-03/003930 A1 | 1/2003 |
| WO | WO 03/022167 | 3/2003 |
| WO | WO 03/051450 | 6/2003 |
| WO | WO-03/059437 A2 | 7/2003 |
| WO | WO-03/099382 A1 | 12/2003 |
| WO | WO-04/023978 A2 | 3/2004 |
| WO | WO-2004/091255 A1 | 10/2004 |
| WO | WO-2005/009218 A2 | 2/2005 |
| WO | WO-2006/041847 A1 | 4/2006 |
| WO | WO 2006/041881 | 4/2006 |
| WO | WO-2006/041881 A2 | 4/2006 |
| WO | WO-2006/060053 A2 | 6/2006 |
| WO | WO 2007/014003 | 2/2007 |
| WO | WO-2007/124458 A2 | 11/2007 |
| WO | WO-2007/135875 A1 | 11/2007 |
| WO | WO-2007/146834 A2 | 12/2007 |
| WO | WO-2008/003058 A2 | 1/2008 |
| WO | WO-2008/036479 A2 | 3/2008 |

(56) References Cited

FOREIGN PATENT DOCUMENTS

| | | |
|---|---|---|
| WO | WO-2008/052186 A2 | 5/2008 |
| WO | WO-2008/061152 A2 | 5/2008 |
| WO | WO-2008/151001 A2 | 12/2008 |
| WO | WO-2009/149315 A2 | 12/2009 |
| WO | WO-2010/033940 A1 | 3/2010 |
| WO | WO-2010/067360 A2 | 6/2010 |
| WO | WO-2011/046880 A2 | 4/2011 |
| WO | WO-2011/053757 A1 | 5/2011 |
| WO | WO-2011/082279 A2 | 7/2011 |
| WO | WO-2011/088399 A1 | 7/2011 |
| WO | WO-2011/094367 A1 | 8/2011 |
| WO | WO-2011/139589 | 11/2011 |
| WO | WO-2011/139589 A2 | 11/2011 |
| WO | WO-2012/112165 | 8/2012 |
| WO | WO-2012/112165 A1 | 8/2012 |

OTHER PUBLICATIONS

Bunch, Jared, et al., Mechanisms of Phrenic Nerve Injury During Radiofrequency Ablation at the Pulmonary Vein Orifice, Journal of Cardiovascular Electrophysiology, 16(12): 1318-1325 (2005).
Campese, et al., Renal afferent denervation prevents hypertension in rats with chronic renal failure, Hypertension, 25:878-882 (1995).
Dibona, Renal nerves in compensatory renal response to contralateral renal denervation, Renal Physiology, 238 (1):F26-F30 (1980).
International Search Report & Written Opinion dated Jul. 9, 2014 in Int'l PCT Patent Application Serial No. PCT/US2014/22804 (109317-3110).
International Search Report & Written Opinion dated Nov. 29, 2011 in international PCT Patent Appl No. PCT/US2011/025543 (109317-2810).
International Search Report dated Feb. 9, 2014 in Int'l PCT Patent Appl Serial No. PCT/US2014/022796 (109317-2910).
Oliveira, et a., Renal Denervation Normalizes Pressure and Baroreceptor Reflex in High Renin Hypertension in Conscious Rats, Hypertension 19:17-21 (1992).
OnlineMathLearning.com, Volume Formula, "Volume of a Hollow Cylinder", Oct. 24, 2008.
Smithwick, R.H., Surgery in hypertension, Lancet, 2:65 (1948).
Smithwick, R.H., Surgical treatment of hypertension, Am J Med 4:744-759 (1948).
Wang, S., et al., Effects of Low Intensity Ultrasound on the Conduction Property of Neural Tissues, IEEE International Ultrasonics, Ferroelectrics, and Frequency Control, Joint 50th Anniversary Conference, 2004.
International Search Report dated Jul. 9, 2014 in Int'l PCT Patent Application Serial No. PCT/US2014/22804 (109317-3110).
Written Opinion dated Jul. 9, 2014 in Int'l PCT Patent Application Serial No. PCT/US2014/22804 (109317-3110).
Arruda, M.S., et al. "Development and validation of an ECG algorithm for identifying accessory pathway ablation site in Wolff-Parkinson-White syndrome." J Cardiovasc Electrophysiol, 9:2-12 (1998).
Avitall, B., et al. "The creation of linear continuous lesions in the atria with an expandable loop catheter." J Am Coll Cardiol, 33,4:972-974 (1999).
Bartlett, T.G., et al. "Current management of the Wolff-Parkinson-White syndrome." J Card Surg. 8:503-515 (1993).
Benito, F., et al. "Radio frequency catheter ablation of accessory pathways in infants," Heart, 78:160-162 (1997).
Blumenfeld, J.D., et al. "β-Adrenergic receptor blockade as a therapeutic approach for suppressing the renin-angiotensin-aldosterone system in norrnotensive and hypertensive subjects." AJH, 12:451-459 (1999).
Callans, D. J. "Narrowing of the superior vena cava—right atrium junction during radiofrequency catheter ablation for inappropriate sinus tachycardia: Analysis with intracardiac echocardiography." JACC, 33:1667-1670 (1999).

Cao, H., et al. "Flow effect on lesion formation in RF cardiac catheter ablation." IEEE T Bio-Med Eng, 48:425-433 (2001).
Chen, S.-A., et al. "Complications of diagnostic electrophysiologic studies and radiofrequency catheter ablation in patients with tachyarrhythmias: An eight-year survey of 3,966 consecutive procedures in a tertiary referral center." Am J Cardiol, 77:41-46 (1996).
Chen, Shih-Ann, M.D., "Initiation of Atrial Fibrillation by Ectopic Beats Originating From the Pulmonary Veins," Circulation 100(18):1879-86, 1999.
Chinitz, et al., "Mapping Reentry Around Atriotomy Scars Using Double Potentials," Pacing and Clinical Electrophysiology, Cardiostim 96 Proceedings, Part II, vol. 19:1978-1983 (1996).
Cioni, R., et al. "Renal artery stenting in patients with a solitary functioning kidney." Cardiovasc Intervent Radiol, 24:372-377 (2001).
Cosby, R.L., et al. "The role of the sympathetic nervous system and vasopressin in the pathogenesis of the abnormal sodium and water." Nefrologia, V, 4:271-277 (1985).
Cosio, Francisco G., "Atrial Flutter Mapping and Ablation II," Pacing & Clin. Electrophysiol. 19(6):965-75, 1996.
Cox, J.L. "The status of surgery for cardiac arrhythmias." Circulation, 71 :413-417 (1985).
Cox, J.L. et al. "Five-year experience with the Maze procedure for atrial fibrillation." Ann Thorac Surg, 56:814-824 (1993).
Cruickshank, J.M. "Beta-blockers continue to surprise us." Eur Heart J, 21:354-364 (2000).
Curtis, J.J., et al. "Surgical therapy for persistent hypertension after renal transplantation," Transplantation, 31:125-128 (1981).
Demazumder, D., et al. "Comparison of irrigated electrode designs for radiofrequency ablation of myocardium." J Interv Card Electr, 5:391-400 (2001).
DiBona, G.F. "Neural control of the kidney: Functionally specific renal sympathetic nerve fibers." Am J Physiol Regulatory Integrative Comp Physiol, 279:R1517-R1524 (2000).
DiBona, G.F. "Sympathetic nervous system and kidney in hypertension," Nephrol and Hypertension, 11:197-200 (2002).
DiBona, G.F., et al. "Neural control of renal function," Physiol Rev, 77:75-197 (1997).
DiBona, G.F., et al. "Renal hemodynamic effects of activation of specific renal sympathetic nerve fiber groups." Am J Physiol Regul Integr Comp Physiol, 276:R539-R539 (1999).
Diederich C.J. et al. "Transurethral Ultrasound Array for Prostate Thermal Therapy: Initial Studies", IEEE Transactions on Ultrasonic, Ferroelectronics And Frequency Control Ieeee USA, vol. 43, No. 6, Nov. 1996, pp. 1011-1022.
Doggrell, S.A., et al. "Rat models of hypertension, cardiac hypertrophy and failure." Cardiovasc Res, 39:89-105 (1998).
Dong Q., et al. "Diagnosis of renal vascular disease with MR angiography." RadioGraphies, 19:1635-1554 (1999).
Dubuc, M., et al. "Feasibility of cardiac cryoablation using a transvenous steerable electrode catheter," J Interv Cardiac Electrophysiol, 2:285-292 (1998).
Feld, Gregory K., "Radiofrequency Catheter Ablation for the Treatment of Human Type I Atrial Flutter," Circulation, 86(3):1233-1240 (1992).
Gallagher, John J., "Wolff-Parkinson-White Syndrome: Surgery to Radiofrequency Catheter Ablation," 1997.
Gilard, M., et al. "Angiographic anatomy of the coronary sinus and its tributaries." PACE, 21:2280-2284 (1998).
Gorisch, W., et al. "Heat-induced contraction of blood vessels." Lasers Surg Med, 2:1-13 (1982).
Haines, D.E. et al. "Tissue heating during radiofrequency catheter ablation; A thermodynamic model and observations in isolated perfused and superfused canine right ventricular free wall." PACE, 12:962-976 (1989).
Haissaguerre, et al., "Radiofrequency Catheter Ablation in Unusual Mechanisms of Atrial Fibrillation," Journal of Cardiovascular Electrophysiology, 5(9):743-1751 (1994).
Haissaguerre, et al., "Right and Left Atrial Radiofrequency Catheter Therapy of Paroxysmal Atrial Fibrillation," Journal of Cardiovascular Electrophysiology, 7(12):1133-1144 (1996).
Haissaguerre, Michel, "Electrophysiological End Point for Catheter Ablation of Atrial Fibrillation Initiated From Multiple Venous Foci," Circulation, 101:1409-1417 (2000).

(56) References Cited

OTHER PUBLICATIONS

Haissaguerre, Michel, M.D., "Predominant Origin of Atrial Panarrhythmic Triggers in the Pulmonary Veins: A Distinct Electrophysiologic Entity," 1997.
Haissaguerre, Michel, M.D., et al., "Spontaneous Initiation of Atrial Fibrillation by Ectopic Beats Originating in the Pulmonary Veins," The New England Journal of Medicine, 339(10):659-666 (1998).
Han, Y-M., et al. "Renal artery embolization with diluted hot contrast medium: An experimental study," J Vasc Interv Radiol, 12:862-868 (2001).
Hansen, J.M., et al. "The transplanted human kidney does not achieve functional reinnervation." Clin Sci, 87, 1:13-20 (1994).
Hatala, Robert, "Radiofrequency Catheter Ablation of Left Atrial Tachycardia Originating Within the Pulmonary Vein in a Patient with Dextrocardia," Pacing and Clinical Electrophysiology, 19(6):999-1002 (1996).
Hindricks, G. "The Multicentre European Radiofrequency Survey (MERFS): Complications of radiofrequency catheter ablation of arrhythmias." Eur Heart J, 14:1644-1653 (1993).
Ho, S.Y., et al. "Architecture of the pulmonary veins: Relevance to the radiofrequency ablation." Heart 86:265-270 (2001).
Hocini, et al., "Concealed Left Pulmonary Vein Potentials Unmasked by Left Atrial Stimulation," Pacing and Clinical Electrophysiology, 23(11):1828-1831, part 2 (2000).
Hocini, et al., "Multiple Sources initiating Atrial Fibrillation from a Single Pulmonary Vein Identified by a Circumferential Catheter," Pacing and Clinical Electrophysiology, 23(11):1828-1831, Part 2 (2000).
Hsieh, et al., "Double Multielectrode Mapping Catheters Facilitate Radiofrequency Catheter Ablation of Focal Atrial Fibrillation Originating from Pulmonary Veins," Journal of Cardiovascular Electrophysiology, 10(2):136-144 (1999).
Huang et al., "Renal denervation prevents and reverses hyperinsulinemia-induced hypertension in rats," Hypertension 32, pp. 249-254 (1998).
Huang, S.K.S., et al. "Radiofrequency catheter ablation of cardiac arrhythmias: Basic concepts and clinical applications." 2nd ed. Armonk, NY: Futura Publishing Co. (2000).
Igawa, et al., "The Anatomical Features of the Junction between the Left Atrium and the Pulmonary Veins: The Relevance with Atrial Arrhythmia", Circulation, Journal of the American Heart Association, Abstracts from the 72nd Scientific Sessions, 100(18):1-285 (1999).
Jackman, W.M., et al. "Treatment of supraventricular tachycardia due to atrioventricular nodal reentry by radiofrequency catheter ablation of slow-pathway conduction." N England J Med, 327, 5:313-318 (Jul. 30, 1992).
Jain, M.K., et al. "A three-dimensional finite element model of radiofrequency ablation with blood flow and its experimental validation." Ann Biomed Eng, 28:1075-1084 (2000).
Jais, Pierre, M.D., "A Focal Source of Atrial Fibrillation Treated by Discrete Radiofrequency Ablation," Circulation, 95(3):572-576 (1996).
Kapural, L., et al. "Radiofrequency ablation for chronic pain control." Curr Pain Headache Rep, 5:517-525 (2001).
Kay, et al., "Radiofrequency Ablation for Treatment of Primary Atrial Tachycardia," Journal of the American College of Cardiology, 21(4):901-909 (1993).
Koepke, J.P., et al. "The physiology teacher: Functions of the renal nerves." The Physiologist, 28, 1:47-52 (1985).
Kompanowska-Jezierska, et al. "Early effects of renal denervation in the anaesthetised rat: Natriuresis and increased cortical blood flow," J Physiol, 531.2:527-534 (2001).
Krimholtz et al., "New Equivalent Circuits for Elementary Piezoelectric Transducers," Electronics Lettres, vol. 6, No. 13, pp. 398-399, Jun. 25, 1970.
Kumagai, et al., "Treatment of Mixed Atrial Fibrillation and Typical Atrial Flutter by Hybrid Catheter Ablation," Pacing and Clinical Electrophysiology, 23(11):1839-1842, Part 2 (2000).
Labonte, S. "Numerical model for radio-frequency ablation of the endocardium and its experimental validation." IEEE T Bio-med Eng, 41,2:108-115 (1994).
Lee, S.-J., et al. "Ultrasonic energy in endoscopic surgery," Yonsei Med J, 40:545-549 (1999).
Leertouwer, T.c., et al. "In-vitro validation, with histology, of intravascular ultrasound in renal arteries." J Hypertens, 17:271-277 (1999).
Lesh, M.D., "An Anatomic Approach to Prevention of Atrial Fibrillation: Pulmonary Vein Isolation with Through-the-Balloon Ultrasound Ablation (TTB-US)," Thorac. Cardiovasc. Surg. 47 (1999) (Suppl.) 347-51.
Lesh, Michael D., M. D., "Radiofrequency Catheter Ablation of Atrial Arrhythmias," Circulation, 89(3):1074-1089 (1994).
Liem, L. Bing, "In Vitro and In Vivo Results of Transcatheter Microwave Ablation Using Forward-Firing Tip Antenna Design," Pacing and Clinical Electrophysiology, Cardiostim '96 Proceedings, 19(11), Part 2 pp. 2004-2008 (1996).
Lin, Wei-Shiang, M.D., "Pulmonary Vein Morphology in Patients with Paroxysmal Atrial Fibrillation Initiated by Ectopic Beats Originating From the Pulmonary Veins," Circulation 101(11):1274-81, 2000.
Lowe, J.E. "Surgical treatment of the Wolff-Parkinson-White syndrome and other supraventricular tachyarrhythmias." J Card Surg, 1 :117-134 (1986).
Lundin, S. et al. "Renal sympathetic activity in spontaneously hypertensive rats and normotensive controls, as studied by three different methods." Acta Physiol Scan, 120,2:265-272 (1984).
Lustgarten, D.L., et al. "Cryothermal ablation: Mechanism of tissue injury and current experience in the treatment of tachyarrhythmias," Progr Cardiovasc Dis, 41:481-498 (1999).
Mallavarapu, Christopher, "Radiofrequency Catheter Ablation of Atrial Tachycardia with Unusual Left Atrial Sites of Origin," Pacing and Clinical Electrophysiology, vol. 19(6), pp. 988-992 (1996).
McRury, I.D., et al. "Nonuniform heating during radiofrequency catheter ablation with long electrodes." Circulation, 96:4057-4064 (1997).
Mehdirad, A., et al. "Temperature controlled RF ablation in canine ventricle and coronary sinus using 7 Fr or 5 Fr ablation electrodes." Pace, 21:310-321 (1998).
Miller, B.F., and Keane, C.B. "Miller-Keane Encyclopedia & Dictionary of Medicine, Nursing, & Allied Health." Philadelphia: Saunders (1997) ("ablation").
Misaki, T., et al. "Surgical treatment of patients with Wolff-ParkinsonWhite syndrome and associated Ebstein's anomaly." J Thorae Cardiovase Surg, 110: 1702-1707 (1995).
Moak, J.P., et al. "Case report: Pulmonary vein stenosis following RF ablation of paroxysmal atrial fibrillation: Successful treatment with balloon dilation." J Interv Card Electrophys, 4:621-631 (2000).
Montenero, Sandro, Annibale, "Electrograms for Identification of the Atrial Ablation Site During Catheter Ablation of Accessory Pathways," Pacing and Clinical Electrophysiology, vol. 19(6), pp. 905-912 (1996).
Moubarak, Jean B., "Pulmonary Veins-Left Atrial Junction: Anatomic and Histological Study," Pacing & Clin. Electrophys. 23(11 pt. 2):1836-8, 2000.
Nakagawa, A., et al. "Selective ablation of porcine and rabbit liver tissue using radiofrequency: Preclinical study." Eur Surg Res, 31:371-379 (1999).
Nakagawa, H., et al. "Comparison of in vivo tissue temperature profile and lesion geometry for radiofrequency ablation with a saline-irrigated electrode versus temperature control in a eanine thigh muscle preparation." Circulation, 91 :2264-2273 (1995).
Nakagawa, H., et al. "Inverse relationship between electrode size and lesion size during radiofrequency ablation with active electrode cooling." Circulation, 98:458-465 (1998).
Neutel, J. M. "Hypertension and its management: A problem in need of new treatment strategies." JRAAS, I:S 1 O-S 13 (2000).
O'Connor, B.K., et al. "Radiofrequency ablation of a posteroseptal accessory pathway via the middle cardiac vein in a six-year-old child." Pace, 20:2504-2507 (1997).
Oliveira et al., "Renal Denervation Normalized Pressure and Baroreceptor Reflex in High Renin Hypertension in Conscious Rats," Hypertension Suppl. II vol. 19 No. 2 pp. 17-21 (1992).
Oral, H., et al. "Pulmonary vein isolation for paroxysmal and persistent atrial fibrillation," Circulation, 105: 1077-1081 (2002).

(56) References Cited

OTHER PUBLICATIONS

Page, I., et al. "The effect of renal denervation in the level of arterial blood pressure and renal function in essential hypertension." J Clin Invest, XIV:27-30 (1935).
Panescu, D., et al. "Radiofrequency multielectrode catheter ablation in the atrium." Phys Med Biol, 44:899-915 (1999).
Pavin, D., et al. "Permanent left atrial tachycardia: Radiofrequency catheter ablation through the coronary sinus." J Cardiovasc Electrophysiol, 12:395-398 (2002).
Peet, M., "Hypertension and its surgical treatment by bilateral supradiaphragmatic splanchnicectomy," Am. J. Surgery, pp. 48-68 (1948).
Petersen, H. H., et al. "Lesion dimensions during temperature controlled radiofrequency catheter ablation of left ventricular porcine myocardium: Impact of ablation site, electrode size, and convective cooling." Circulation, 99:319-325 (1999).
Pohl, M.A. "Renovascular hypertension and ischemic nephropathy" A chapter in a book edited by Sehrier, R.W. "Atlas of diseases of the kidney: Hypertension and the kidney." Blackwell Science (1999).
Prager, Nelson, A., "Long Term Effectiveness of Surgical Treatment of Ectopic Atrial Tachycardia," Journal of the American College of Cardiology, vol. 22(1):85-92 (1993).
Pugsley, M.K., et al. "The vascular system" An overview of structure and function. J Pharmacol Toxical Methods, 44:333-340 (2000).
Rappaport et al. "Wide-Aperture Microwave Catheter-Based Cardiac Ablation", Proceedings of the First Joint BMES/EMBS Conference, Oct. 13-16, 1999, p. 314.
Reuter, David, M.D., et al., "Future Directions of Electrotherapy for Atrial Fibrillation," Journal of Cardiovascular Electrophysiology, 9(8):S202-S210 (1998).
Robbins, Ivan, M.D., "Pulmonary Vein Stenosis After Catheter Ablation of Atrial Fibrillation," Circulation, 98:1769-1775 (1998).
Sanderson, J.E., et al. "Effect of B-blockage on baroreceptor and autonomic function in heart failure." Clin Sei, 69:137-146 (1999).
Schauerte, P., et al. "Catheter ablation of cardiac autonomic nerves for prevention of vagal atrial fibrillation," Circulation, 102:2774-2780 (2000).
Scheinman, M. M., et al. "The 1998 NASPE prospective catheter ablation registry." Pace, 23:1020-1028 (2000).
Scheinman, Melvin M., "NASPE Survey on Catheter Ablation," 1995.
Smithwick et al., "Splanchnicetomy for Essential Hypertension," J. Am. Med. Assn. 152:16, pp. 1501-1504 (1953).
Solis-Herruzo et al., "Effects Lumbar Sympathetic Block on Kidney Function in Cirrhotic Patients with Hepatorneal Syndrome," J. Hepatol. 5, pp. 167-173 (1987).
Stella, A., et al. "Effects of reversible renal denervation on hemodynamic and excretory functions of the ipsilateral and contralateral kidney in the cat," J Hypertension, 4:181-188 (1986).
Stellbrink, C., et al. "Transcoronary venous radiofrequency catheter ablation of ventricular tachycardia." J Cardiovasc Electropysiol 8:916-921 (1997).
Swain, et al., An endoscopically deliverable tissue-transfixing device for securing biosensors in the gastrointestinal tract, Gastrointestinal Endoscopy. 1994, 40:AB35.
Swartz, John F., "A Catheter-based Curative Approach to Atrial Fibrillation in Humans," Circulation, Abstracts from the 67th Scientific Sessions, Clinical Cardiology: Radio Frequency Ablation of Atrial Arrhythmias, 90(4), part 2, I-335 (1994).
Swartz, John F., M.D., "Radiofrequency Endocardial Catheter Ablation of Accessory Atrioventricular Pathway Atrial Insertion Sites," Circulation, 87:487-499 (1993).
Takahashi, H., et al. "Retardation of the development of hypertension in DOCA-salt rats by renal denervation." Jpn Circ J, 48:567-574 (1984).
Tanaka et al., "A new radiofrequency thermal balloon catheter for pulmonary vein isolation," Journal of the American College of Cardiology 38(7):2079-86, Dec. 2001.
Tracy, Cynthia M., "Radiofrequency Catheter Ablation of Ectopic Atrial Tachycardia Using Paced Activation Sequence Mapping," J. of the Amer. College of Cardiol. 21(4):910-7, 1993.
Tungjitkusolmun, S. "Ablation." A chapter in a book edited by Webster, J. G., "Minimally invasive medical technology." Bristol UK: IOP Publishing, 219 (2001).
Uchida, F., et al. "Effect of radio frequency catheter ablation on parasympathetic denervation: A comparison of three different ablation sites," Pace, 21:2517-2521 (1998).
Uflacker, R., "Atlas of vascular anatomy: An angiographic approach." Baltimore: Williams & Wilkins, 424 (1997).
Valente, J. F. "Laparoscopic renal denervation for intractable ADPKD-related pain," Nephrol Dial Transplant, 16:160 (2001).
Van Hare, G. F., et al., "Percutaneous radiofrequency catheter ablation for supraventricular arrhythmias in children." JACC, 17:1613-1620 (1991).
Van Hare, George F., "Radiofrequency Catheter Ablation of Supraventricular Arrhythmias in Patients With Congenital Heart Disease: Results and Technical Considerations," J. of the Amer. College of Cardiol, 22(3):883-90, 1993.
Volkmer, Marius, M.D., "Focal Atrial Tachycardia from Deep Inside the Pulmonary Veins," Pace vol. 20:533, p. 1183 (1997).
Vujaskovie, Z., et al. "Effects of intraoperative hyperthermia on canine seiatie nerve: Histopathology and morphometric studies." Int JHyperthermia, 10,6:845-855 (1994).
Walsh, Edward P., M.D., "Transcatheter Ablation of Ectopic Atrial Tachycardia in Young Patients Using Radiofrequency Current," Circulation, 86(4):1138-1146 (1992).
Weinstock, M., et al. "Renal denervation prevents sodium retention and hypertension in salt-sensitive rabbits with genetic baroreflex impairment," Clinical Science, 90:287-293 (1996).
Weir, M. R., et al. "The renin-angiotensin-aldosterone system: A specific target for hypertension management." Am J Hypertens, 12:205S-213S (1999).
Yamamoto, T., et al. "Blood velocity profiles in the human renal artery by Doppler ultrasound and their relationship to atherosclerosis." Arterisocl Throm Vas, 16: 172-177 (1996).
Zhang et al., "The development of a RF electrical pole catheter for heart ablation," China Academic Journal Electronic Publishing House 23(5): 279-80, Sep. 1999 (With English Abstract).
Zipes, Douglas P., M.D., "Catheter Ablation of Arrhythmias," 1994.
Extended EP Search Report dated Dec. 5, 2016 in EP Patent Application Serial No. 16183988.1 (109317-3131).
www.dictionary.com/browse/degrease, retrieved Jun. 7, 2016.
European Search Report dated Feb. 17, 2016 in European Patent Application No. 14775754.6.
Accornero, Neri, et al., "Selective Activation of Peripheral Nerve Fibre Groups of Different Diameter by Triangular Shaped Stimulus Pulses", J. Physiol. (1977), 273, 539-560, 22 Q9S.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 758-765 (2012).
American Heart Association—Pulmonary Hypertension: High Blood Pressure in the Heart-to-Lung System, (last reviewed Oct. 31, 2016).
Appeal Brief of Patent Owner from Reexamination 95-002, 110.
Aytac, et al., "Correlation Between the Diameter of the Main Renal Artery and the Presence of an Accessory Renal Artery", J Ultrasound Med 22:433-439, 2003 (.
Azizi, Michel et al., Ultrasound renal denervation for hypertension resistant to a triple medication pill (Radiance-HTN Trio): a randomised, multicentre, single-blind, sham-controlled trial, 397 Lancet 2476 (2021).
Bailey, M.R. et al., Physical Mechanisms of the Therapeutic Effect of Ultrasound (A Review), Acoustical Physics, vol. 49, No. 4, 2003, pp. 369-388.
Bengel, et al., Serial Assessment of Sympathetic Reinnervation After Orthotopic Heart Transplantation; A Longitudinal Study Using PET and C-11 Hydroxyephedrine, Circulation. 1999;99: 1866-1871.
Bhatt, D.L., et al., A Controlled Trial of Renal Denervation for Resistant Hypertension, New England J. Med., 370:1393-1401 (2014).

(56) References Cited

OTHER PUBLICATIONS

Bhatt, Deepak L. et al., Long-term outcomes after catheter-based renal artery denervation for resistant hypertension: final follow-up of the randomised Symplicity HTN-3 Trial, 400 Lancet 1405 (2022).
Bisdas, Theodosios et al., Initial Experience with the 6-F and 8-F Indigo Thrombectomy System for Acute Renovisceral Occlusive Events, Journal of Endovascular Therapy, vol. 24, No. 4, 604-610 (2017).
Blanketjin, Peter, Sympathetic Hyperactivity in Chronic Kidney Disease, Neprhrol Dial Transplant, vol. 19, No. 6, 1354-1357 (2004).
Blum et al., Treatment of Ostial Renal-Artery Stenoses with Vascular Endoprostheses after Unsuccessful Balloon Angioplasty, N. Engl. J. Med. 336 459-65 (1997).
Bonsignore, C., "A Decade of Evolution in Stent Design", Proceedings of the International Conference on Shape Memory and Superelastic Technologies, (2003).
Bradfield, Jason S. et al., Renal denervation as adjunctive therapy to cardiac sympathetic denervation for ablation refractory ventricular tachycardia, Heart Rhythm Society, vol. 17, No. 2, 220-227 (2020).
Bush, et al., "Endovascular revascularization of renal artery stenosis: Technical and clinical results", Journal of Vascular Surgery, May 2001, 1041-1049 (2001).
Camasao, D.B. et al., The mechanical characterization of blood vessels and their substitutes in the continuous quest for physiological-relevant performances: A critical review, Materials Today Bio, vol. 10 (2021).
Carter, J. , "Microneurography and Sympathetic Nerve Activity: A Decade-By-Decade Journey across 50 Years," Journal of Neurophysiology, vol. 121, No. 4. doi: 10.1 152/jn.00570.2018.
Carter, Stefan et al., Measurement of Renal Artery Pressures by Catheterization in Patients with and without Renal Artery Stenosis, Circulation, vol. XXXIII, 443-449 (1966).
Charlesworth, Peter et al., Renal Artery Injury From a Fogarty Balloon Catheter, Journal of Vascular Surgery, vol. 1, No. 4, 573-576 (1984).
Chart showing priority claims of the '629 patent, exhibit to Petition for Inter Partes Review of U.S. Pat. No. 8,845,629, filed Jan. 13, 2022 in the Patent Trial and Appeal Board, United States Patent and Trademark Office, Petition No. PTAB-IPR2022-00431.
Chiesa et al., Endovascular Stenting for the Nutcracker Phenomenon, J. Endovasc. Ther., 8:652-655 (2001).
Corrected Patent Owner's Response to Office Action, dated May 10, 2013, from File History of Inter Partes Reexamination No. 95/002,110.
Correspondence from PTAB Deputy Chief Clerk to Counsel re conference call request-Exhibit 3001 in the Patent Trial and Appeal Board, United States Patent and Trademark Office, Petition No. PTAB-IPR2022-00431.
Curriculum Vitae of Dr. John M. Moriarty.
Curriculum Vitae of Dr. Michael Bohm.
Curriculum Vitae of Farrell Mendelsohn.
Curriculum Vitae of Dr. Chris Daft.
Dangas, G., et al., Intravascular Ultrasound-Guided Renal Artery Stenting, J Endovasc Ther, 2001;8:238-247 (2001).
Deardorff, Dana et al., Ultrasound Applicators with Internal Water-Cooling for High-Powered Interstitial Thermal Therapy, IEEE Transactions on Biomedical Engineering, vol. 47, No. 10, 1356-1365 (2000).
Decision of the Patent Trial and Appeal Board in U.S. Appl. No. 14/731,347.
Declaration of Chris Daft dated Jan. 11, 2022, in the Patent Trial and Appeal Board, United States Patent and Trademark Office, Petition No. PTAB-IPR2022-00431.
Second Declaration of Chris Daft. Dated Jan. 10, 2023, in the Patent Trial and Appeal Board, United States Patent and Trademark Office, Petition No. PTAB-IPR2022-00431.
Declaration of Dr. Daniel van der Weide, dated Oct. 26, 2022, in the Patent Trial and Appeal Board, United States Patent and Trademark Office, Petition No. PTAB-IPR2022-00431.

Declaration of Dr. Dieter Haemmerich, dated Aug. 29, 2012, in the Patent Trial and Appeal Board, United States Patent and Trademark Office, In re U.S. Pat. No. 7,717,948.
Declaration of Dr. John M. Moriarty in German Nullity proceedings for EP 2261905, dated Jul. 13, 2022.
Declaration of Dr. John Moriarty, dated Jan. 19, 2023, in the Patent Trial and Appeal Board, United States Patent and Trademark Office, Petition No. PTAB-IPR2022-00431.
Declaration of Jonathan Bradford in Support of Patent Owner'sResponse, dated Oct. 27, 2022.
Declaration of Jonathan Bradford dated May 10, 2022, in the Patent Trial and Appeal Board, United States Patent and Trademark Office, Petition No. PTAB-IPR2022-00431.
Declaration of Dr. Michael Bohm dated Sep. 29, 2022 on behalf of Medtronic Inc.
Declaration of Dr. Robert Tucker, dated Oct. 27, 2022, in the Patent Trial and Appeal Board, United States Patent and Trademark Office, Petition No. PTAB-IPR2022-00431.
Declaration of Farrell Mendelsohn dated Jan. 10, 2022, in the Patent Trial and Appeal Board, United States Patent and Trademark Office, Petition No. PTAB-IPR2022-00431.
Defendant's Reply to Court Order of Oct. 4, 2022 and Plaintiff's Surrejoinder of Sep. 29, 2022 in the Mannheim District Court, case No. 7 O 14/21, dated Oct. 31, 2022.
Defendant's Response dated May 11, 2022 in the Munich Federal Patent Court, Nullity Suit 6 Ni 32/22.
DiBona, Gerald F., "Neural Control of the Kidney, Past, Present and Future," 41 [Part II] Hypertension 621 24 (2003).
DiBona, Gerald F. et al., "Neural Control of Renal Function", 77 Physiological Reviews No. 1, 75 (1997).
DiBona, Gerald, Sympathetic Nervous System and Kidney in Hypertension, Current Opinion in Nephrology and Hypertension, vol. 11, 197-200 (2002).
Diederich, et al., Ultrasound Catheters for Circumferential Cardiac Ablation, in Proceedings of SPIE Conference on Thermal Treatment of Tissue with Image Guidance San Jose, California, Jan. 1999 SPIE vol. 3594.
Diedrich, A. et al.,"Analysis of Raw Microneurographic Recordings Based on Wavelet De-Noising Technique and 1 Classification Algorithm: Wavelet Analysis in Microneurography," IEEE Trans Biomed Eng. Jan. 2003 ; 50(1): 41-50_doi:10.1109fTBME.2002.807323.
Draney, Mary et al., Three-Dimensional Analysis of Renal Artery Bending Motion During Respiration, International Society of Endovascular Specialists, vol. 12, 380-386 (2005).
EP Board of Appeals Communication dated Dec. 17, 2019—Preliminary Remarks for EP appeal No. T2680/16-3.3.4.01.
Erikson, Kenneth et al., Ultrasound in Medicine: A Review, IEEE Transactions on Sonics and Ultrasonics, vol. 21, No. 3 (1974).
European Communication dated Oct. 23, 2013 in EP Application No. 12180431.4.
European Office Action re Application No. 12180431.4.
European Patent No. 12167931, Claims of the Main Request dated Sep. 30, 2016.
European Search Report (supplementary) dated Feb. 17, 2016 in European Patent Application No. 14775754.6.
European Search Report dated Mar. 1, 2021 in European Patent Application No. 20202272.9.
European Search Report for Patent Application No. EP12180431 dated Jan. 17, 2013.
Fengler, Karl et al., A Three-Arm Randomized Trial of Different Renal Denervation Devices and Techniques in Patients With Resistant Hypertension (Radiosound-HTN), 139 Circulation 590 (2019).
File History to EP1802370B1 Part 1.
File History to EP1802370B1 Part 2.
File History to EP1802370B1 Part 3.
Gallitto, Enrico et al., Renal Artery Orientation Influences the Renal Outcome in Endovascular Thoraco-abdominal Aortic Aneurysm Repair, European Society of Endovascular Surgery, vol. 56, No. 3, 382-390 (2018).
Gervais, Debra A. et al., Radiofrequency ablation of renal cell carcinoma: Part 2, Lessons learned with ablation of 100 tumors, 185 AJR Am. J. Roentgenol. 72 (2005).

(56) References Cited

OTHER PUBLICATIONS

Goldberg, S. Nahum et al., EUS-guided radiofrequency ablation in the pancreas: results in a porcine model, 50 Gastrointest. Endosc. 392 (1999).
Golwyn et al., Percutaneous Transcatheter Renal Ablation with Absolute Ethanol for Uncontrolled Hypertension or Nephrotic Syndrome: Results in 11 Patients with End-Stage Renal Disease, J. Vasco and Interventional Radiology, 8,527-433 (1997).
Gorsich, W., et al., Heat-Induced Contraction of Blood Vessels, Lasers in Surgery and Medicine, 2:1-13 (1982).
Gray, Henry, Gray's Anatomy: The Anatomical Basis of Medicine and Surgery, Churchill Livingstone, New York, NY (1995).
Habict, Antje et al., Sympathetic Overactivity and Kidneys, The Middle European Journal of Medicine, vol. 115, 634-640 (2003).
Hansen et al., The Transplanted Human Kidney Does Not Achieve Functional Reinnervation, 87 Clinical Science 13 (1994).
Harrison, R.R. et al., "A Low-Power Integrated Circuit for a Wireless 1 OD-Electrode Neural Recording System," IEEE Journal of Solid-State Circuits, vol. 42, No. 1, pp. 123-133, Jan. 2007. doi: 10.1 109/JSSC.2006.886567.
He, D. S. et al., Application of Ultrasound Energy for Intracardiac Ablation of Arrhythmias, European Heart Journal, vol. 16, 961-966 (1995).
Heffner, H. et al., "Gain, Band Width, and Noise Characteristics of the Variable-Parameter Amplifier," Journal of Applied Physics, vol. 29, No. 9, Sep. 1958, 1 1 pages.
Holmes, David R. et al., Pulmonary vein stenosis complicating ablation for atrial fibrillation: clinical spectrum and interventional considerations, 2 JACC Cardiovasc. Interv. 267 (2009).
Hsu, Thomas H. S. et al., Radiofrequency ablation of the kidney: acute and chronic histology in porcine model, 56 Urology 872 (2000).
Huang, S.K.S. and Wilbur, D. Eds, Radiofrequency Catheter Ablation of Cardiac Arrhythmias, Basic Concepts and Clinical Applications, Futura Publishing Company, Inc., Armonk, New York (2000).
Huang, et al., Renal Denervation Prevents and Reverses Hyperinsulinemia-Induced Hypertension in Rats, Hypertension 32 (1998) pp. 249-254.
Institution Decision Granting Institution of Inter Partes Review 35 U.S.C. sec. 314, dated Aug. 8, 2022 in the Patent Trial and Appeal Board, United States Patent and Trademark Office, Petition No. PTAB-IPR2022-00431.
Isles et al., Management of Renovascular Disease: A Review of Renal Artery Stenting in Ten Studies, QJM 92, 159-67 (1999).
Ivanisevic, N., "Circuit Design Techniques for Implantable Closed-Loop Neural Interfaces," Doctoral Thesis in Information and Communication Technology, KTH School of Electrical Engineering and Computer Science, Sweden, May 2019, 92 pages.
Janssen, B. J. A., et al. "Renal nerves in hypertension." Miner Electrolyte Metab., 15:74-82 (1989).
Janzen, Nicolette et al., Minimally Invasive Ablative Approaches in the Treatment of Renal Cell Carcinoma, Current Urology Reports, vol. 3 (2002).
Kaltenbach, Benjamin et al., Renal Artery Stenosis After Renal Sympathetic Denervation, Journal of the American College of Cardiology, vol. 60, No. 25 (2012).
Kapural, Leonardo, et al., "Radiofrequency Ablation for Chronic Pain Control," Anesthetic Techniques in Pain Management, pp. 517-525, 2001.
Katholi, R.E., et al., Importance of Renal Sympathetic Tone in the Development of DOCA-Salt Hypertension in The Rat, Hypertension, 2:266-273 (1980).
Kim, Yun-Hyeon et al., Pulmonary vein diameter, cross-sectional area, and shape: CT analysis, Radiology Society of North America, vol. 235, No. 1, 49-50 (2005).
Kirsh, Danielle, Balloon Catheters: What are some key design considerations?, Massdevice (Dec. 6, 2016).
Kompanowska-Jezierska, Elzbieta et al., Early Effects of Renal Denervation in the Anaesthetized Rat: Natriuresis and Increased Cortical Blood Flow, 531 J. Physiology No. 2, 527 (2001).
Koomans, Hein et al., Sympathetic Hyperactivity in Chronic Renal Failure: A wake-up call, Frontiers in Nephrology, vol. 15, 524-537 (2004).
Kuo, et al., "Atrial Fibrillation: New Horizons", Chang Gung Med J vol. 26 No. Oct. 10, 2003.
Lang, Roberto et al., Recommendations for Chamber Quantification: A Report from the American Society of Echocardiography's Guidelines and Standards Committee and the Chamber Quantification Writing Group, Developed in Conjunction with the European Association of Echocardiography, a Branch of the European Society of Cardiology, Journal of the American Society of Echocardiography, vol. 18, No. 12, 1440-1463 (2005).
Lee, Jong Deok et al., MR imaging-histopathologic correlation of radiofrequency thermal ablation lesion in a rabbit liver model: observation during acute and chronic stages, 2 Korean J. Radiol. 151 (2001).
Levin, S., et al., ARDIAN: Succeeding Where Drugs Fail—Treating Hypertension in the Cath Lab, In Vivo, 27:23 (2009).
Mahfoud, Felix et al., Catheter-Based Renal Denervation is No Simple Matter: Lessons to be Learned From Our Anatomy?, Journal of the American College of Cardiology, vol. 64, No. 7, 644-647 (2014).
Marine, Joseph E., Catheter ablation therapy for supraventricular arrhythmias, 298 JAMA 2768 (2007).
Martin, Louis K. et al., Long-term Results of Angioplasty in 110 Patients with Renal Artery Stenosis, Journal of Vascular and Interventional Radiology, vol. 3, No. 4, 619-626 (1992).
Maslov, P., "Recruitment Pattern of Muscle Sympathetic Nerve Activity in Chronic Stable Heart Failure Patients and in Healthy Control Subjects," Doctoral Dissertation, University of Split, Croatia, 2013, 69 pages.
Matsumoto, Edward D. et al., Short-term efficacy of temperature-based radiofrequency ablation of small renal tumors, 65 Urology 877 (2005).
Medtronic Press Release, Medtronic Announces U.S. Renal Denervation Pivotal Trial Fails to Meet Primary Efficacy Endpoint While Meeting Primary Safety Endpoint (Jan. 9, 2014).
Medtronic Inc., Renal Denervation (RDN): Novel Catheter-Based Treatment for Hypertension, Scientific Background, 2011.
Medtronic Scientific Background, Hypertension and the Symplicity Renal Denervation System.
Medtronic, Symplicity RDN Common System Q&A.
Medtronic Inc., The Symplicity RDN System, 2012.
Meyers, Philip et al., Temporary Endovascular Balloon Occlusion of the Internal Carotid Artery with a Nondetachable Silicone Balloon Catheter: Analysis Technique and Cost, American Journal of Neuroradiology, vol. 20, No. 4, 559-564 (1999).
Millard, et al., Renal Embolization for Ablation of Function in Renal Failure And Hypertension, Postgraduate Med. J. 65, 729-734 (1989).
Mitchell, et al., "The Renal Nerves" British Journal of Urology, Read by invitation at the Sixth Annual Meeting of the British Association of Urological Surgeons on Jun. 30, 1950.
Morrissey, D. M. "Sympathectomy in the treatment of hypertension." Lancet, CCLXIV:403-408 (1953).
Nair et al., "The Need for and the Challenges of Measuring Renal Sympathetic Nerve Activity," Heart Rhythm 2016; 13:1166-1171.
Natale, Andrea et al., First Human Experience with Pulmonary Vein Isolation Using a Through-the-Balloon Circumferential Ultrasound Ablation System for Recurrent Atrial Fibrillation, Circulation, vol. 102, 1879-1882 (2000).
Netter, Frank, Atlas of Human Anatomy, Icon Learning Systems, Rochester, NY (2002).
Neumann, Jutta, Sympathetic hyperactivity in chronic kidney disease: Pathogenesis, clinical relevance, and treatment, International Society of Nephrology, vol. 65, 1568-1576 (2004).
News, Columbia University Irving Medical Center, Zapping Nerves with Ultrasound Lowers Drug-Resistant Blood Pressure (May 16, 2021), https://www.cuimc.columbia.edu/news/zapping-nervesultrasound-lowers-drug-resistant-blood-pressure.
Notice of Deposition of Tucker, filed Dec. 30, 2022 in the Patent Trial and Appeal Board, United States Patent and Trademark Office, Petition No. PTAB-IPR2022-00431.

(56) References Cited

OTHER PUBLICATIONS

Notice of Deposition of van der Weide, filed Dec. 30, 2022 in the Patent Trial and Appeal Board, United States Patent and Trademark Office, Petition No. PTAB-IPR2022-00431.
Notice re filing date accorded, dated Feb. 10, 2022 in the Patent Trial and Appeal Board, United States Patent and Trademark Office, Petition No. PTAB-IPR2022-00431.
Nozawa, T., et al. "Effects of long-term renal sympathetic denervation on heart failure after myocardial infarction in rats." Heart Vessels, 16:51-56 (2002).
Oliveira, Vera L. et al., "Renal Denervation Normalizes Pressure and Baroreceptor Reflex in High Renin Hypertension in Conscious Rats", 19 Hypertension Suppl. II No. 2, 17 (1992) ("Oliveira 1992").
Order: Conduct of the Proceeding Scheduling Order 37 C.F.R. sec. 42.5, dated Aug. 8, 2022 in the Patent Trial and Appeal Board, United States Patent and Trademark Office, Petition No. PTAB-IPR2022-00431.
Olsson, R. et al., "A Three-Dimensional Neural Recording Microsystem With Implantable Data Compression 5 Circuitry," ISSCC. 2005 IEEE International Digest of Technical Papers. Solid-State Circuits Conference, 2005., San Francisco, CA, 2005, pp. 558-559 vol. 1 doi:10.1109/JSSC.2005.858479.
Order Setting Oral Hearing 37 C.F.R. § 42.70, dated Mar. 24, 2023 in the Patent Trial and Appeal Board, United States Patent and Trademark Office, Petition No. PTAB-IPR2022-00431.
Osborn, J., "Catheter-Based Renal Nerve Ablation as a Novel Hypertension Therapy, Lost, and Then Found," in Translation.
Page, Irvine H. & George J. Heuer, The Effect of Renal Denervation on the Level of Arterial Blood Pressure and Renal Function in Essential Hypertension, 14 J. Clinical Investigation 27 (1935) (received for publication in 1934).
Page, Irvine H. & George J. Heuer, The Effect of Renal Denervation on Patients Suffering from Nephritis, 14 J. Clinical Investigation 443 (1935) (received for publication in 1935).
Papademetriou, Vasilios et al., Renal Sympathetic Denervation for the Treatment of Difficult-to-Control or Resistant Hypertension, 2011 Int. J. Hypertension, Article 196518 (2011).
Papademetriou, et al., "Renal Sympathetic Denervation: Hibernation or Resurrection?", Cardiology 2016 ; 135, 11 pgs.
Pappone C, et al., "Circumferential radiofrequency ablation of pulmonary vein ostia: a new anatomic approach for curing atrial fibrillation", Circulation. 2000; 102(21): 2619-2628. (2000).
Patent Owner's Amended Objections to Evidence Under 37 C.F.R. §42.64.
Patent Owner's Mandatory Notice, filed Feb. 3, 2022 in the Patent Trial and Appeal Board, United States Patent and Trademark Office, Petition No. PTAB-IPR2022-00431.
Patent Owner's Notice of Deposition of Dr. Chris Daft, filed Sep. 20, 2022 in the Patent Trial and Appeal Board, United States Patent and Trademark Office, Petition No. PTAB-IPR2022-00431.
Patent Owner's Notice of Deposition of Dr. Chris Daft filed Feb. 21, 2023 in the Patent Trial and Appeal Board, United States Patent and Trademark Office, Petition No. PTAB-IPR2022-00431.
Patent Owner's Notice of Deposition of Dr. Farrell Mendelsohn, filed Sep. 21, 2022 in the Patent Trial and Appeal Board, United States Patent and Trademark Office, Petition No. PTAB-IPR2022-00431.
Patent Owner's Notice of Deposition of Dr. John Moriarty, filed Feb. 21, 2023 in the Patent Trial and Appeal Board, United States Patent and Trademark Office, Petition No. PTAB-IPR2022-00431.
Patent Owner's Objections to Evidence, filed Aug. 18, 2022 in the Patent Trial and Appeal Board, United States Patent and Trademark Office, Petition No. PTAB-IPR2022-00431.
Patent Owner's Power of Attorney, filed Feb. 3, 2022 in the Patent Trial and Appeal Board, United States Patent and Trademark Office, Petition No. PTAB-IPR2022-00431.
Patent Owner Medtronic Ireland Power of Attorney, filed May 10, 2022 in the Patent Trial and Appeal Board, United States Patent and Trademark Office, Petition No. PTAB-IPR2022-00431.
Patent Owner's Preliminary Response, filed May 10, 2022 in the Patent Trial and Appeal Board, United States Patent and Trademark Office, Petition No. PTAB-IPR2022-00431.
Patent Owner's Request for Oral Hearing, filed Mar. 23, 2023 in the Patent Trial and Appeal Board, United States Patent and Trademark Office, Petition No. PTAB-IPR2022-00431.
Patent Owner's Response, filed Oct. 27, 2022 in the Patent Trial and Appeal Board, United States Patent and Trademark Office, Petition No. PTAB-IPR2022-00431.
Patent Owner's Sur-Reply, filed Mar. 9, 2023 in the Patent Trial and Appeal Board, United States Patent and Trademark Office, Petition No. PTAB-IPR2022-00431.
Patent Owner's Updated Mandatory Notice, filed May 10, 2022 in the Patent Trial and Appeal Board, United States Patent and Trademark Office, Petition No. PTAB-IPR2022-00431.
Peet, M.M., Hypertension and Its Surgical Treatment by Bilateral Supradiaphragmatic Splanchnicectomy, Am. J. Surgery, LXXV:48-68 (1948).
Petition for Inter Partes Review of U.S. Pat. No. 8,845,629, dated Jan. 13, 2022 by ReCor Medical, Inc. and Otsuka Medical Devices Co., Ltd., in the Patent Trial and Appeal Board, United States Patent and Trademark Office, Petition No. PTAB-IPR2022-00431.
Petitioner ReCor's Biography of Dr. Neil C. Barman.
Petitioner's Power of Attorney for Otsuka Medical Devices Co., Ltd., filed Jan. 13, 2022 in the Patent Trial and Appeal Board, United States Patent and Trademark Office, Petition No. PTAB-IPR2022-00431.
Petitioner's Power of Attorney for Recor Medical, Inc., filed Jan. 13, 2022 in the Patent Trial and Appeal Board, United States Patent and Trademark Office, Petition No. PTAB-IPR2022-00431.
Petitioner Reply, filed Jan. 23, 2023 in the Patent Trial and Appeal Board, United States Patent and Trademark Office, Petition No. PTAB-IPR2022-00431.
Petitioners' Request for Oral Argument, filed Mar. 21, 2023 in the Patent Trial and Appeal Board, United States Patent and Trademark Office, Petition No. PTAB-IPR2022-00431.
Petitioners' Updated Mandatory Notices, dated Jan. 18, 2022 in the Patent Trial and Appeal Board, United States Patent and Trademark Office, Petition No. PTAB-IPR2022-00431.
Plaintiff's Nullity Brief, dated Jan. 14, 2022, in the Munich Federal Patent Court, Nullity Suit 6 Ni 32/22.
Plaintiff's Reply to the May 11, 2022 Response, dated Jul. 18, 2022, in the Munich Federal Patent Court, Nullity Suit 6 Ni 32/22.
Plaintiff's Response to Court Order disagreeing with Stay of Proceedings dated Oct. 28, 2022 in Mannheim District Court, Infringement suit 7 O 147/21.
Plaintiff's Technical Brief dated Sep. 29, 2022 in the Mannheim District Court, Infringement suit 7 O 147/21.
Plouin et al., Blood Pressure Outcome of Angioplasty in Atherosclerotic Renal Artery Stenosis: A Randomized Trial. Essai Multicentrique Medicaments vs Angioplastie (EMMA) Study Group, Hypertension 31, 823-29 (1998).
Prochnau, Dirk et al., Catheter-based renal denervation for drug-resistant hypertension by using a standard electrophysiology catheter, EuroIntervention, vol. 7, 1077-1080 (2012).
Pugsley, et al., The vascular system: An overview of structure and function, Journal of Pharmacological and Toxicological Methods 44 (2000) 333-340.
Pürerfellner, Helmut et al., Incidence, Management and Outcome in Significant Pulmonary Vein Stenosis Complicating Ablation for Atrial Fibrillation, 93 Am. J. Cardiol. 1428 (2004).
Pürerfellner, Helmut & Martin Martinek, Pulmonary vein stenosis following catheter ablation of atrial fibrillation, 20 Curr. Opin. Cardiol. 484 (2005).
Reaz, M.B.I., et al., "Techniques of EMG signal analysis: detection, processing, classification and applications," Biological Procedures Online, Jan. 2006, 25 pages.
Romanes, G.J., Cunningham's Textbook of Anatomy (11th ed. 1972).
Ryan, Thomas et al., Proceedings of Thermal Treatment of Tissue with Image Guidance, Progress in Biomedical Optics, vol. 3594 (1999).

(56) References Cited

OTHER PUBLICATIONS

Ryan, Thomas P._ Thermal Treatment of Tissue with Image Guidance; Ultrasound Catheters for Circumferential Cardiac Ablation 1999.
Ryan, Steve, What are the Risks Associated with a Pulmonary Vein Ablation Procedure?, Atrial Fibrillation: Resources for Patients (last accessed Oct. 18, 2022).
Sakakura, Kenichi et al., Anatomic Assessment of Sympathetic Peri-Arterial Renal Nerves in Man, Journal of the American College of Cardiology, vol. 64, No. 7, 635-643 (2014).
Salmanpour, A., L. J. Brown and J. K. Shoemaker, "Detection of Single Action Potential in Multi-Unit Postganglionic 7 Sympathetic Nerve Recordings in Humans: A Matched Wavelet Approach," 2010 IEEE International Conference on Acoustics, Speech and Signal Processing, Dallas, TX, 2010, pp. 554-557. doi: 10.1 109/ICASSP. 2010.5495604.
Sánchez-Quintana, Damian et al., How close are the phrenic nerves to cardiac structures? Implications for cardiac interventionalists, 16 J. Cardiovasc. Electrophysiol 309 (2005) ("Sánchez-Quintana").
Schlaich, M.P. et al., "Renal Denervation: A Potential New Treatment Modality for Polycystic Ovary Syndrome," Journal of Hypertension, vol. 29, No. 5, pp. 991-996 2011 . doi:10.1097/HJH. 0b013e328344db3a.
Schmieder, Ronald E., Renal denervation in patients with chronic kidney disease: current evidence and future perspectives, Nephrol. Dial. Transplant. gfac189 (2022).
Schmidt, Boris, et al., "Pulmonary Vein Isolation by High Intensity Focused Ultrasound," Indian Pacing and Electrophysiology Journal, pp. 126-133 (2006).
Schneider, Peter, Endovascular Skills: Guidewire and Catheter Skills for Endovascular Surgery, 2nd ed., Marcel Dekker, Inc., New York, NY (2003).
Schneider, Peter A., Endovascular Skills, Quality Medical Publishing, Inc., 1998 ("Schneider").
Selected documents from the File History of Inter Partes Reexamination No. 95/002,110, exhibit to Petition for Inter Partes Review of U.S. Pat. No. 8,845,629, filed Jan. 13, 2022 in the Patent Trial and Appeal Board, United States Patent and Trademark Office, Petition No. PTAB-IPR2022-00431.
Shimizu, Kazumasa et al., Sympathetic Dysfunction in Heart Failure, Bailliere's Clinical Endocrinology and Metabolism, vol. 7, No., 2 (1993).
Shonai et al., Renal Artery Aneurysm: Evaluation with Color Doppler Ultrasonography Before and lifter Percutaneous Transarterial Embolization, J. Ultrasound Med. 19, 277-80 (2000)("Shonai 2000").
Slide deck from Medtronic Circulatory System Devices Panel Meeting, General Issues Panel: Clinical Evaluation of Anti-Hyperintensive Devices (Dec. 5, 2018).
Smithwick, R. H., et al., "Splanchnicectomy for essential hypertension." J. Am. Med. Assoc., 152:1501-1504 (1953).
Stella, A., et al. "Effects of reversible renal denervation on haemodynamic and excretory functions of the ipsilateral and contralateral kidney in the cat." J Hypertension, 4: 181-188 (1986)("Stella").
Stipulation Modifying Schedule, dated Dec. 30, 2022 in the Patent Trial and Appeal Board, United States Patent and Trademark Office, Petition No. PTAB-IPR2022-00431.
Stipulation Modifying Schedule, dated Feb. 16, 2023 in the Patent Trial and Appeal Board, United States Patent and Trademark Office, Petition No. PTAB-IPR2022-00431.
Stoeckel, D. et al., A Survey of Stent Designs, Min Invas Ther & Allied Technol 2002: 11(4) 137-147 (2002).
Swartz, John F. et al., Radiofrequency Endocardial Catheter Ablation of Accessory Atrioventricular Pathway Atrial Insertion Sites, 87 Circulation 487 (1993).
Tank, J. et al., "Spike Rate of Multi-Unit Muscle Sympathetic Nerve Fibers Following Catheter-Based Renal Nerve Ablation," J Am. Soc Hypertens, Oct. 2015 ; 9(10): 794-801 . doi:10.1016/j.jash.2015. 07.012.
Teigen et al., Segmental Renal Artery Embolization for Treatment of Pediatric Renovascular Hypertension, J. Vasco Interv. Radiol. 3, 111-7 (1992).
Thatipelli, Mallik R., et al., CT angiography of renal artery anatomy for evaluating embolic protection devices, 18 J. Vasc. Interv. Radiol. 842 (2007).
The Doctors and Experts at WebMD, Webster's New World Medical Dictionary (3rd ed. 2008) ("WebsterMD").
Transcript of the Mar. 2, 2023 deposition of Dr. John Moriarty.
Transcript of the Mar. 3, 2023 deposition of Dr. Chris Daft.
Transcript of deposition of the Jan. 1, 2023 deposition of Dr. Robert Tucker.
Transcript of the Jan. 14, 2023 deposition of Dr. Daniel van der Weide.
Transcript of the Sep. 30, 2022 deposition of Dr. Chris Daft.
Transcript of the Oct. 1, 2022 deposition of Dr. Farrell Mendelsohn.
Tsao, Hsuan-Ming et al., Evaluation of Pulmonary Vein Stenosis after Catheter Ablation of Atrial Fibrillation, 6 Card. Electrophysiol. Rev. 397 (2002).
Turner, et al., "Initial Experience Using the Palmaz Corinthian Stent for Right Ventricular Outflow Obstruction in Infants and Small Children", Catheterization and Cardiovascular Interventions 51:444-449 (2000).
Uchida, et al., "Effect of radiofrequency catheter ablation on parasympathetic denervation: A comparison of three different ablation sites." Pace 21 :2517-2521 (1998).
Vaezy, Shahram et al., Image-Guided Acoustic Therapy, Annual Review Biomedical Engineering, vol. 3, 375-390 (2001).
Valente, John F. et al., Laparoscopic renal denervation for intractable ADPKD-related pain, 16 Nephrol. Dial. Transplant. 160 (2001).
Vujaskovic, Z. et al., (1994) Effects of intraoperative hyperthermia on canine sciatic nerve: histopathologic and morphometric studies, International Journal of Hyperthermia, 10:6, 845-855 (1994) ("Vujaskovic 1994").
Wanchoo, Nishey, Medtronic Gets European and Australian Approval for Symplicity Spyral Multi-Electrode Renal Denervation Catheter, Medgadget (2013).
Weinstock, Marta et al., "Renal Denervation Prevents Sodium Retention and Hypertension in Salt-Sensitive Rabbits with Genetic Baroreflex Impairment", 90 Clinical Science 287 (1996).
Xu, J. et al., "A Bidirectional Neuromodulation Technology for Nerve Recording and Stimulation, Micromachines," vol. 9, 1 1 538. Oct. 23, 2018. doi:10.3390/mi9110538.
Xu, J., T. Wu and Z. Yang, "A New System Architecture for Future Long-Term High-Density Neural Recording," IEEE Transactions on Circuits and Systems II: Express Briefs, vol. 60, No. 7, pp. 402-406, Jul. 2013. doi: 10.1109/TCSII.2013.2258270.
Zazgornik, "Bilateral Nephrectomy: The best, but often overlooked, treatment for refractory hypertension in hemodialysis patients," Am. J. Hypertension, 11:1364-1370 (1998).
Ziegler et al., Sources of Urinary Catecholamines in Renal Denervated Transplant Recipients, 8 J. Hypertension No. 10, 927 (1990).
U.S. Appl. No. 17/453,636, filed Nov. 4, 2021.
U.S. Appl. No. 10/408,665.
U.S. Appl. No. 60/624,793.
U.S. Appl. No. 60/370,190.
U.S. Appl. No. 60/415,575.
U.S. Appl. No. 60/442,970.
U.S. Appl. No. 60/616,254.
U.S. Appl. No. 60/816,999.
U.S. Appl. No. 14/683,966, Non Final Office Action mailed Jun. 12, 2017, 14 pgs.
U.S. Appl. No. 14/683,966, Response filed Nov. 10, 2017 to Non Final Office Action mailed Jun. 12, 2017, 13 pqs.
U.S. Appl. No. 14/683,966, Notice of Allowance mailed Jan. 31, 2018, 8 pgs.
U.S. Appl. No. 14/683,966, PTO Response to Rule 312 Communication mailed Mar. 29, 2018, 2 pgs.
U.S. Appl. No. 14/683,966, 312 Amendment filed Mar. 13, 2018, 10 pgs.
U.S. Appl. No. 14/683,966, Corrected Notice of Allowance mailed May 22, 2018, 4 pgs.

(56) References Cited

OTHER PUBLICATIONS

U.S. Appl. No. 15/204,349, Preliminary Amendment filed Nov. 30, 2016, 3 pgs.
U.S. Appl. No. 15/204,349, Restriction Requirement mailed May 17, 2018, 7 pgs.
U.S. Appl. No. 15/204,349, Response filed Jun. 5, 2018 to Restriction Requirement mailed May 18, 2017, 7 pgs.
U.S. Appl. No. 15/204,349, Non Final Office Action mailed Nov. 27, 2018, 14 pgs.
U.S. Appl. No. 15/204,349, Response filed Feb. 27, 2019 to Non Final Office Action mailed Nov. 27, 2018, 10 pgs.
U.S. Appl. No. 15/204,349, Final Office Action mailed Apr. 22, 2019, 16 pgs.
U.S. Appl. No. 15/204,349, Response filed Jun. 24, 2019 to Final Office Action mailed Apr. 22, 2019, 12 pgs.
U.S. Appl. No. 15/204,349, Advisory Action mailed Jul. 9, 2019, 5 pgs.
U.S. Appl. No. 15/299,694, Restriction Requirement mailed Aug. 6, 2018, 6 pgs.
U.S. Appl. No. 15/299,694, Response filed Oct. 8, 2018 to Restriction Requirement mailed Aug. 6, 2018, 7 pgs.
U.S. Appl. No. 15/299,694, Non Final Office Action mailed Nov. 27, 2018, 15 pgs.
U.S. Appl. No. 15/299,694, Response filed Feb. 27, 2019 to Non-Final Office Action mailed Nov. 27, 2018, 10 pgs.
U.S. Appl. No. 15/299,694, Final Office Action mailed Apr. 22, 2019, 16 pgs.
U.S. Appl. No. 15/299,694, Response filed Jun. 24, 2019 to Final Office Action mailed Apr. 22, 2019, 11 pgs.
U.S. Appl. No. 15/299,694, Advisory Action mailed Jul. 9, 2019, 5 pgs.
U.S. Appl. No. 15/943,354, Preliminary Amendment filed Apr. 3, 2018, 9 pgs.
U.S. Appl. No. 15/943,354, Restriction Requirement mailed Nov. 20, 2019, 8 pages.
U.S. Appl. No. 15/943,354, Response filed Dec. 19, 2019 to Restriction Requirement mailed Nov. 20, 2019, 8 pages.
U.S. Appl. No. 15/943,354, Non Final Office Action mailed Jan. 13, 2020, 6 pages.
U.S. Appl. No. 15/943,354, Non Final Office Action mailed Apr. 20, 2020, 7 pages.
U.S. Appl. No. 15/996,978, Preliminary Amendment filed Jun. 5, 2018, 11 pgs.
U.S. Appl. No. 15/996,978, Restriction Requirement mailed Feb. 7, 2020, 7 pages.
U.S. Appl. No. 15/996,978, Response filed Apr. 6, 2020 to Restriction Requirement mailed Feb. 7, 2020, 8 pages.
U.S. Appl. No. 15/996,978, Restriction Requirement mailed Apr. 16, 2020, 8 pages.
U.S. Appl. No. 15/996,978, Response filed May 1, 2020 to Restriction Requirement mailed Apr. 16, 2020, 8 pgs.
U.S. Appl. No. 15/996,978, Non Final Office Action mailed Jun. 11, 2020, 8 pages.
U.S. Appl. No. 16/517,180, Preliminary Amendment filed Jul. 19, 2019, 12 pgs.
File History of U.S. Appl. No. 12/754,337.
File History to U.S. Pat. No. 9,943,666.
File History to U.S. Pat. No. 9,981,108.
File History to U.S. Pat. No. 10,039,901.
Final Office Action dated Feb. 19, 2021, U.S. Appl. No. 15/996,978, filed Jun. 4, 2018.
Final Office Action dated Jun. 16, 2021, U.S. Appl. No. 15/996,978, filed Jun. 4, 2018.
Non-final Office Action dated Sep. 2, 2021, U.S. Appl. No. 15/996,978, filed Jun. 4, 2018.
Notice of Allowance dated Oct. 6, 2021, U.S. Appl. No. 15/996,978, filed Jun. 4, 2018.
Response to Office Action dated May 18, 2021, U.S. Appl. No. 15/996,978, filed Jun. 4, 2018.
Response to Office Action dated Jul. 20, 2021, U.S. Appl. No. 15/996,978, filed Jun. 4, 2018.
Response to Office Action dated Sep. 22, 2021, U.S. Appl. No. 15/996,978, filed Jun. 4, 2018.
Berjano, E., et al., "A Cooled Intraesophageal Balloom to Prevent Thermal Injury during Endocardial Surgical Radiofrequency Ablation of the left Atrium: a finite element study." Physics in Medicine and Biology, 50(20): 269-279, 2015.
Billard, B.E., et al., Effects of Physical Parameters on High Temperature Ultrasound Hyperthermia, Ultrasound in Med. & Biol. vol. 16, No. 4, pp. 409-420, 1990.
Chapelon, J.Y., "Treatment of Localised Prostate Cancer with Transrectal High Intensity Focused Ultrasound," European Journal of Ultrasound 9, 31-38, 1999.
Deardorff, Dana et al., Ultrasound Applicators with Internal Cooling for Interstitial Thermal Therapy, SPIE vol. 3594, 36-46, Jan. 1999.
Diederich, et al., "Catheter-based Ultrasound Applicators for Selective Thermal Ablation: progress towards MRI-guided applications in prostate," International Journal of Hyperthermia, 20:7, 739-756.
European Application No. 14188428.8, File History.
European Search Report dated Nov. 19, 2018 in European Patent Application No. 218186547.
Fan, Xiaobing, et al., "Control of the Necrosed Tissue Volume during Noninvasive Ultrasound Surgery using a 16-Element Phased Array," Department of Radiology, Brigham and Women's Hospital, Harvard Medical School, Oct. 31, 1994.
Foley, Jessica L., et al., "Image-Guided HIFU Neurolysis of Peripheral Nerves to Treat Spasticity and Pain," Ultrasound in Med & Biol., vol. 30, Np. 9 pp. 1199-1207, 2004.
Papadopoulos, N., "Evaluation of a Small Flat Rectangular Therapeutic Ultrasonic Transducer Intended for Intravascular Use," Ultrasonics 74, 196-203, 2017.
Prakash, Punit, et al., "Considerations for Theoretical Modeling of Thermal Ablation with Catheter-Based Ultrasonic Sources: Implications for Treatment Planning, Monitoring and Control," International Journal of Hyperthermia, 28:1, 69-86.
Reddy, Vivek Y., "Use of a Diode Laser Balloon Ablation Catheter to Generate Circumferential Pulmonary Venous Lesions in an Open-Thoracotomy Caprine Model," Pace, vol. 27, 52-57, Jan. 2004.
Ulmsten, Ulf et al., "The Safety and Efficacy of MenoTreat™, a new balloon device for thermal endometrial ablation," Acta Obstet Gynecol Scand 2001; 80: 52-57.
U.S. Appl. No. 60/747,137, File History.
U.S. Appl. No. 60/808,306, File History.
U.S. Appl. No. 61/405,472, File History.
Borchert, Bianca et al., "Lethal Atrioesophageal Fistual After Pulmonary Vein Isolation using High-Intensity Focused Ultrasound (HIFU)" J. Hrthm vol. 5, Issue 1, p. 145-148, Jan. 2008.
Calkins, Hugh et al., "Temperature Monitoring During Radiofrequency Catheter Ablation Procedures Using Closed Loop Control," Circulation vol. 90, No. 3, p. 1279-1286, Sep. 1994.
Deardorff, Dana L. et al., "Control of interstitial thermal coagulation: Comparative evaluation of microwave and ultrasound applicators," Medical Physics vol. 28, No. 1, p. 104-117, Jan. 2001.
Dinerman, Jay L. et al., "Temperature Monitoring During Radiofrequency Ablation," Journal of Cardiovascular Electrophysiology, vol. 7 No. 2, p. 163-173, Feb. 1996.
Esler, Murray et al., "The future of renal denervation," Autonomic Neuroscience: Basic and Clinical, vol. 204, p. 131-138, May 2017.
Filonenko, E.A. et al., "Heating of Biological Tissues by Two-Dimensional Phased Arrays with Random and Regular Element Distributions," Acoustical Physics, vol. 50 No. 2, p. 222-231, 2004.
Fry, William J., "Action of Ultrasound on Nerve Tissue—A review," The Journal of the Acoustical Society of America, vol. 25 No. 1, p. 1-5, Jan. 1953.
Fry, Frank J., "Precision High Intensity Focusing Ultrasonic Machines for Surgery," High Intensity Focused U.S., 152-156, Sep. 6-7, 1957.
Haines, David, "Biophysics of Ablation: Application to Technology," Journal of Cardiovascular Electrophysiology, vol. 15, No. 10, p. S2-S11, Oct. 2004.

(56) References Cited

OTHER PUBLICATIONS

Hynynen, K. et al., "Design of Ultrasonic Transducers for Local Hyperthermia," Ultrasound in Med. & Biol., vol. 7, No. 4, p. 397-402, Feb. 1981.

Hynynen, K. et al., "Temperature measurements during ultrasound hyperthermia," Medical Physics vol. 16, No. 4, p. 618-626, Jul./Aug. 1989.

Jolesz, Ferenc A. et al., "MR Imaging-Controlled Focused Ultrasound Ablation: A Noninvasive Image-Guided Surgery," Magnetic Resonance Imaging Clinics of North America, vol. 13, Issue 3, p. 545-560, 2005.

Kandzari, David A., et al., "Reply to letter to the editor by Kintur Sanghvi, MD; Allen McGrew, DO; and Kiran Hegde, BE, MBS," American Heart Journal, vol. 180, p. e3-e4, Oct. 2016.

Lafon, C. et al., "Design and Preliminary Results of an Ultrasound Applicator for Interstitial Thermal Coagulation," Ultrasound in Medicine & Biology, vol. 24, No. 1, p. 113-122, 1998.

Lewis, Matthew A. et al., "Thermometry and Ablation Monitoring with Ultrasound," Int. J. Hyperthermia vol. 31, Issue 2, p. 163-181, Mar. 2015.

Liu, Xinmeng et al., "Visualization and mapping of the right phrenic nerve by intracardiac echocardiography during atrial fibrillation ablation," Europace vol. 25, p. 1352-1360, 2023.

Mendelsohn, Farrell O., "Microanatomy of the Renal Sympathetic Nervous System," Endovascular Today, p. 59-62, Oct. 2013.

Okamura, Keisuke et al., "Intravascular Ultrasound Can Be Used to Locate Nerves, but not Confirm Ablation, During Renal Sympathetic Denervation," J. Clin. Med. Res., vol. 13, No. 12, p. 556-562, 2021.

Quadri, Syed A. et al., "High-intensity focused ultrasound: past, present, and future in neurosurgery," Neurosurgical Focus, vol. 44, No. 2, p. 1-9, Feb. 2018.

Ross, Anthony B. et al., "Highly directional transurethral ultrasound applicators with rotational control for MRI-guided prostatic thermal therapy," Physics in Medicine & Biology, vol. 49, p. 189-204, Jan. 2004.

Sakaoka, Atsushi, et al., "Accurate Depth of Radiofrequency-Induced Lesions in Renal Sympathetic Denervation Based on a Fine Histological Sectioning Approach in a Porcine Model," Cir. Cardiovasc. Interv., vol. 11, p. 1-8, 2018.

Sanghvi, Kintur et al., "Rationale and design for studies of renal denervation in the absence (Spyral HTN Off-Med) and presence (Spyral HTN On-Med) of antihypertensive medications," American Heart Journal, vol. 180, p. e1-e2. Oct. 2016.

Satou, Shunsuke et al., "Observation of renal sympathetic nerves by intravascular ultrasound," Hypertension Research vol. 42, p. 1092-1094, 2019.

Schmidt, Boris et al., "Balloon Catheters for Pulmonary Vein Isolation," Herz vol. 33, p. 580-584, 2008.

Smith, Nadine Barrie et al., "Transrectal Ultrasound Applicator for Prostate Heating Monitored Using MRI Thermometry," Int. J. Radiation Oncology Biol. Phys. vol. 43, No. 1, p. 217-225, 1998.

Stauffer, P.R. et al., "13 Interstitial Heating Technologies," Thermoradiotherapy and Thermochemotherapy, p. 279-320, 1995.

Swanson, David K. et al., "Tissue temperature Feedback Control of Power, The Key to Successful Ablation," Innovations, vol. 6 No. 4, p. 276-282, Jul./Aug. 2011.

Tabei, Makoto et al., "A k-space method for coupled first-order acoustic propagation equations," J. Acoust. Soc. Am., vol. 111, No. 1, pt. 1, p. 53-63, Jan. 2002.

Tzafriri, Abraham R. et al., "Innervation Patterns May Limit Response to Endovascular Renal Denervation," Journal of the American College of Cardiology, vol. 64, No. 11, p. 1079-1087, Sep. 2014.

Umemura, Shin-ichiro, "Focused ultrasound transducer for thermal treatment," International Journal of Hyperthermia, vol. 31, No. 2, p. 216-221, 2015.

Wan, Hong et al., "Thermal Dose Optimization for Ultrasound Tissue Ablation," IEE Transactions on Ultrasonics, Ferroelectrics, and Frequency Control, vol. 46, No. 4, p. 913-928, Jul. 1999.

Zivin, Adam, et al., "Temperature Monitoring versus Impedance Monitoring during RF Catheter Ablation," Radiofrequency Catheter Ablation of Cardiac Arrhythmias, Basic Concepts and Clinical Applications, Second Edition, Edited by Shoei K. Stephen Huang, MD & David J. Wilber, MD, p. 103-112, 2000.

\* cited by examiner

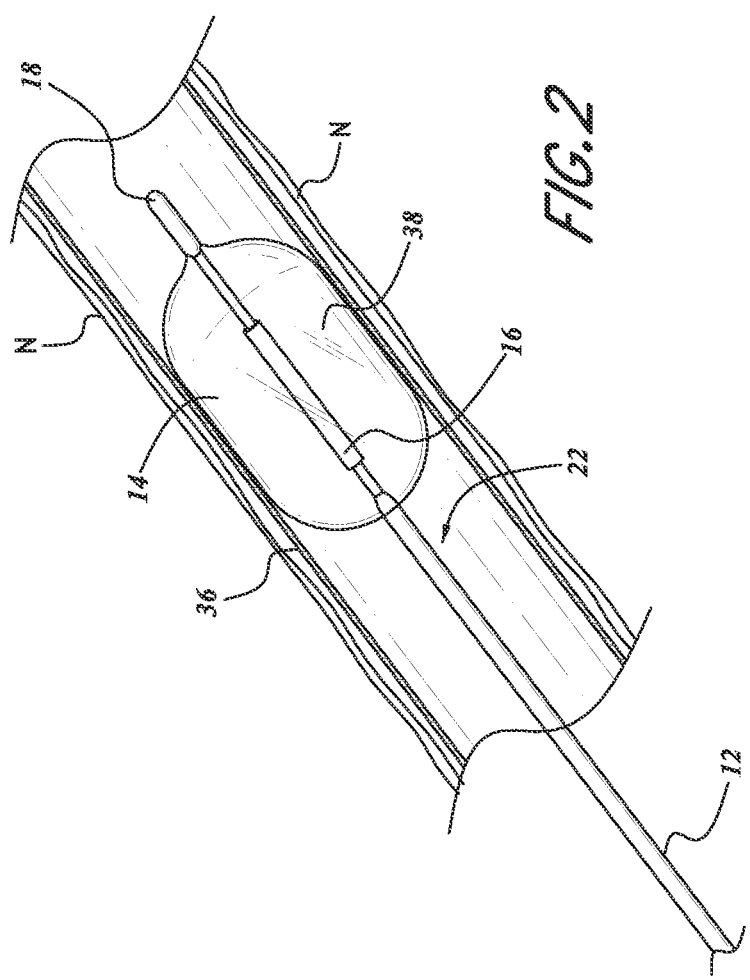

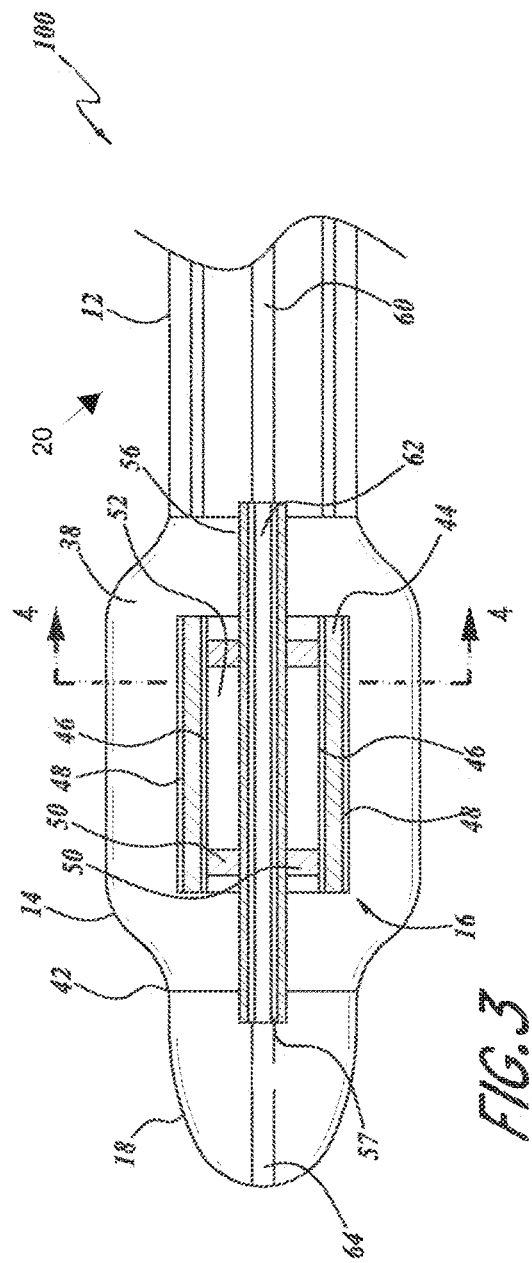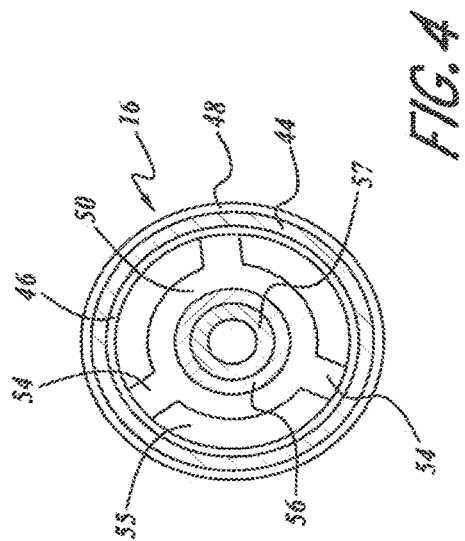

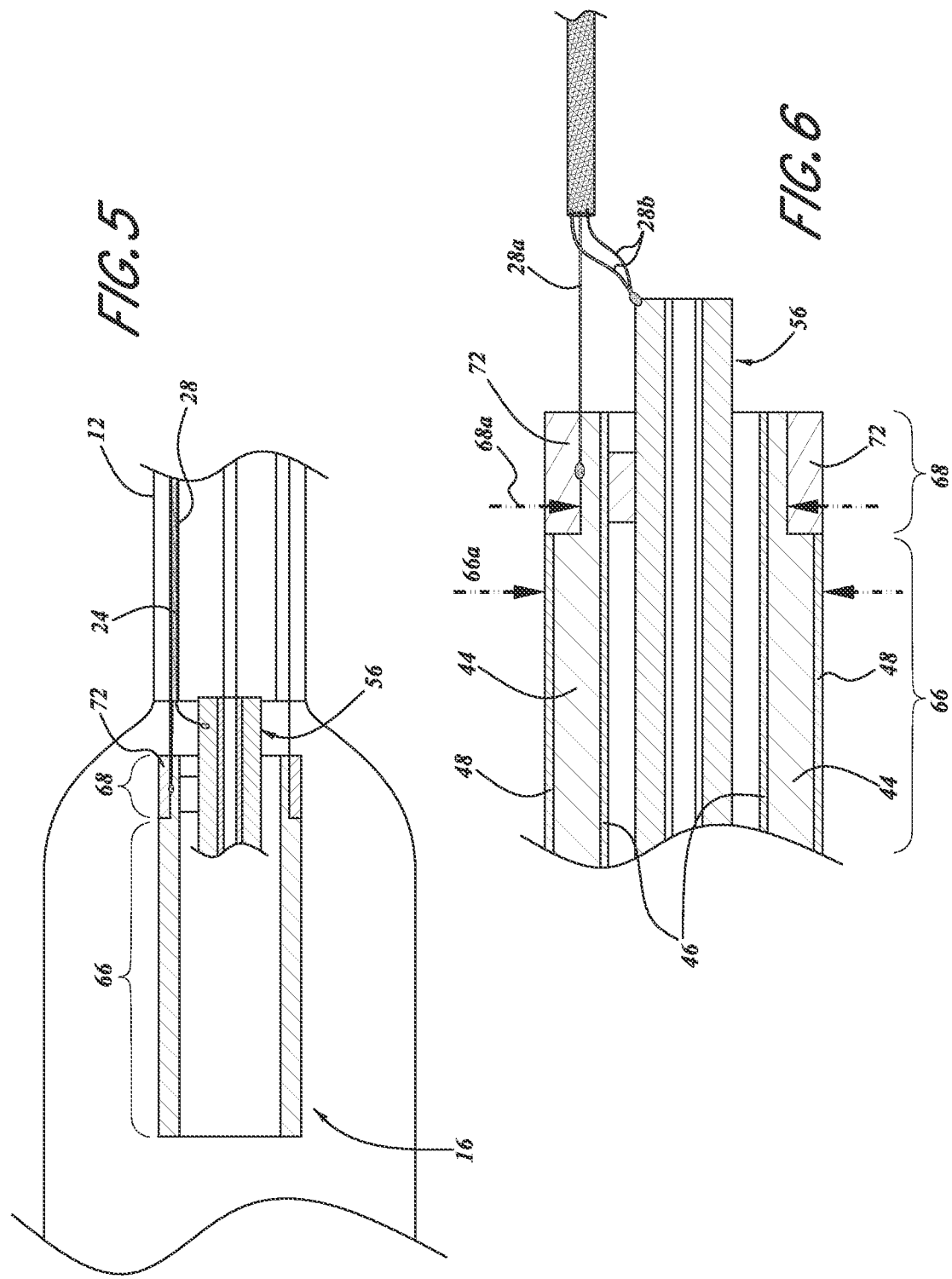

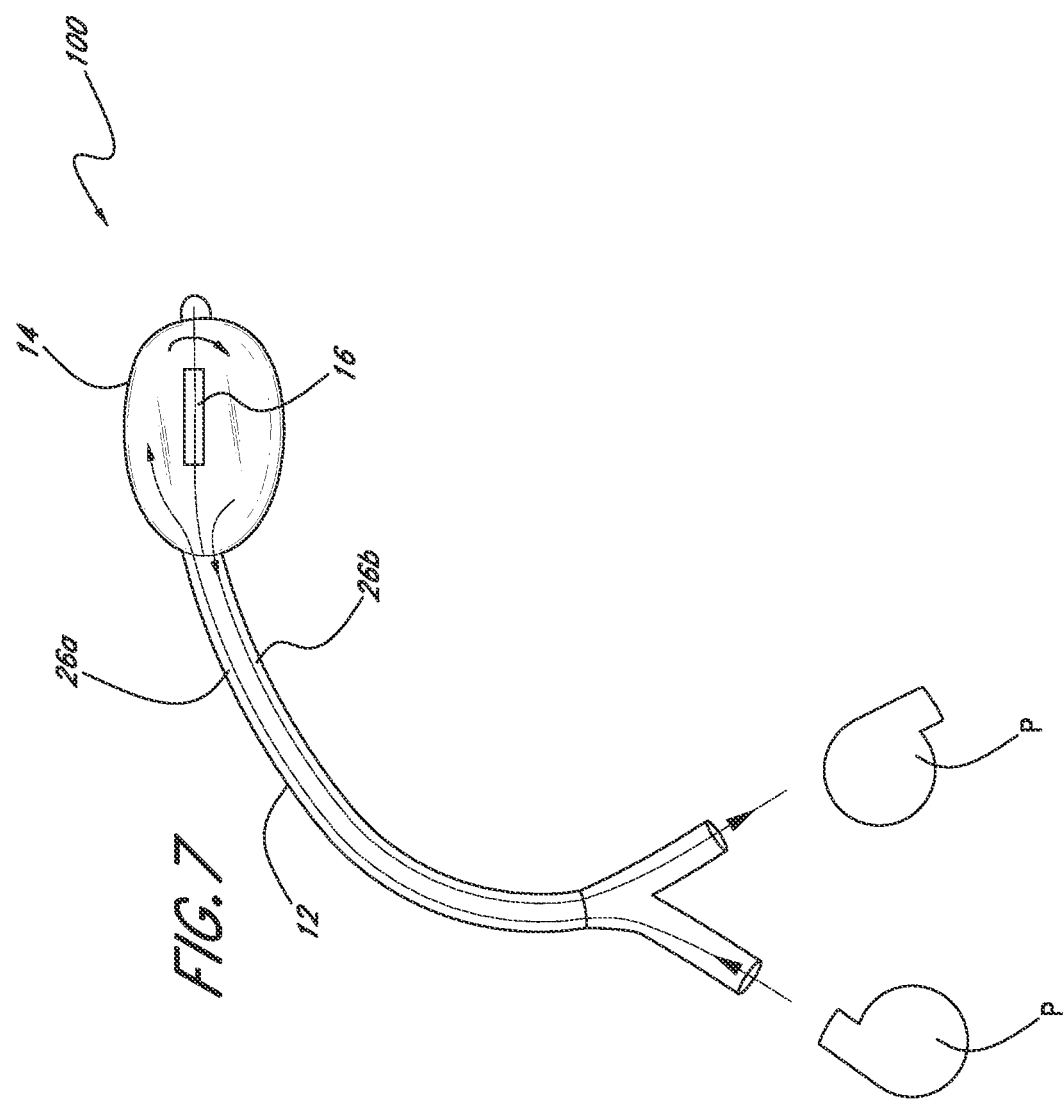

ULTRASOUND-BASED NEUROMODULATION SYSTEM

CROSS-REFERENCE TO RELATED APPLICATIONS

This application is a divisional application of U.S. patent application Ser. No. 14/773,285, filed Sep. 4, 2015, now U.S. Pat. No. 10,456,605, which is a national phase application under 35 U.S.C. § 371 of PCT/US2014/022804, filed Mar. 10, 2014, which claims the benefit of priority to U.S. Provisional Patent Application Ser. Nos. 61/814,167, filed Apr. 19, 2013, and 61/784,790, filed Mar. 14, 2013, the disclosures of each of which are incorporated herein by reference in their entireties. This application is also related to U.S. patent application Ser. No. 14/209,948, filed Mar. 13, 2014, now U.S. Pat. No. 10,350,440, which claims the benefit of priority to U.S. Provisional Patent Application Ser. No. 61/784,790, filed Mar. 14, 2013, the disclosures of each of which are incorporated herein by reference in their entireties.

BACKGROUND

Field

This application relates generally to minimally-invasive devices, systems and methods of energy delivery to a targeted anatomical location of a subject, and more specifically, to catheter-based, intraluminal devices and systems configured to emit ultrasonic energy for the neuromodulation (e.g., ablation, necrosing, etc.) of nerve tissue.

Description of the Related Art

Catheter-based energy delivery systems can be used to access and treat portions of a subject's anatomy minimally-invasively. Such systems can be advanced through a subject's vasculature to reach a target anatomical site. Various embodiments disclosed herein provide improved devices, systems and methods related to energy delivery within a subject.

SUMMARY

According to some embodiments, a catheter for enhancing fluid delivery to a distal end of the catheter while reducing an overall diameter of the catheter comprises a guidewire lumen oriented along an axis that is eccentric relative to a center axis of the catheter (e.g., not positioned along the radial centerline or along the central axis or longitudinal axis of the catheter). The guidewire lumen being can be configured to receive a guidewire therethrough in order to intraluminally deliver the catheter to a target location within a subject. The catheter further comprises at least one fluid lumen configured to transfer a fluid through the catheter. In one embodiment, the eccentric orientation of the guidewire lumen within the catheter allows the cross-sectional area of the at least one fluid lumen to be increased.

According to some embodiments, the catheter further comprises at least one centering assembly located at or near the distal end of the catheter, wherein the at least one centering assembly comprises a passage that is positioned along the center axis of the catheter. In some embodiments, a guidewire is configured to be positioned through the passage of the at least one centering assembly so that the guidewire is generally radially centered along the distal end of the catheter, while the guidewire is configured to eccentrically located within the guidewire lumen of the catheter. In some embodiments, the at least one centering assembly is located immediately adjacent the distal end of the catheter (e.g., such that the centering assembly at least partially touches or otherwise engages or abuts the catheter). In one embodiment, the at least one centering assembly is separated from the distal end of the catheter by a separation distance (e.g., 0-1 mm, 1-2 mm, 2-3 mm, 3-4 mm, 4-5 mm, 5-10 mm, more than 10 mm, etc.). In some embodiments, the at least one centering assembly is located proximal to the distal end of the catheter (e.g., at least partially within the catheter).

In some embodiments, the ultrasonic transducers are operated in a range of from 1 to 20 MHz (e.g., 1-5 MHz, 5-10 MHz, 10-15 MHz, 15-20 MHz, 8-10 MHz, other values or ranges within the foregoing, etc.). In one embodiment, for example, the ultrasound transducer of the system is configured to operate at a frequency of about 9 MHz. In other embodiments, however, the frequency at which a transducer is operated can be below 1 MHz (e.g., 0.1-0.2, 0.2-0.3, 0.3-0.4, 0.4-0.5, 0.5-0.6, 0.6-0.7, 0.7-0.8, 0.8-0.9, 0.9-1.0 MHz, frequencies between the foregoing ranges, less than 0.1 MHz, etc.) or above 20 MHz (e.g., 20-25, 25-30 MHz, frequencies between the foregoing ranges, above 30 MHz, etc.), as desired or required for a particular application or use. The power supplied to the ultrasound transducer can vary, as desired or required, and in some embodiments, is 5 to 80 Watts (e.g., 5 to 50, 5 to 10, 10 to 20, 20 to 30, 30 to 40, 40 to 50, 50 to 60, 60 to 70, 70 to 80 Watts, power levels between the foregoing ranges, etc.) at the transducer.

In some embodiments, the ultrasonic transducer is activated for about 10 seconds to 5 minutes (e.g., 10-30 seconds, 30 seconds to 1 minute, 30 seconds to 5 minutes, 1 to 3 minutes, about 2 minutes, 10 seconds to 1 minute, 1 to 2 minutes, 2 to 3 minutes, 3 to 4 minutes, 4 to 5 minutes, time periods between the foregoing ranges, etc.). In other embodiments, the ultrasonic transducer is activated for less than 10 seconds (e.g., 0-1, 1-2, 2-3, 3-4, 4-5, 5-6, 6-7, 7-8, 8-9, 9-10 seconds, time periods between the foregoing ranges, etc.) or more than 5 minutes (e.g., 5-6, 6-7, 7-8, 8-9, 9-10, 10-15, 15-20 minutes, time periods between the foregoing, more than 20 minutes, etc.).

According to some embodiments, the system comprises an ultrasound transducer having a variety of shapes. The transducer can be cylindrical or non-cylindrical. In some embodiments, the transducer comprises, at least in part, an hourglass shape, a barbell shape, a convex shape or surface, a concave shape or surface and cone shape, an irregular shape and/or the like.

According to some embodiments, prior to inflation of a balloon or other expandable member, the ultrasonic transducer is activated to measure the vessel's diameter. In one embodiment, this is accomplished by sending out a single (or a distinct number of) ultrasonic waves and recording the time period required for the signals to return (e.g., bounce back) to the transducer surface. Thus, in some embodiments, a control system of the system can be configured to both emit acoustic energy and detect it (e.g., at or along the outside of the transducer).

According to some embodiments, a system comprises an array of transducers (e.g., an array comprising 2, 3, 4, 5, 6, 7, 8, 9, 10, 10-15, more than 15 transducers, etc.). In embodiments comprising 2 or more transducers (e.g., an array of transducers), one or more of the transducers can be configured to emit more or less ultrasonic energy than one or more other transducers. In some embodiments, the amount of acoustic energy that is emitted by the plurality of transducers varies (e.g., linearly, non-linearly, randomly, etc.) along a longitudinal axis of the system. In some embodiments, one or some ultrasound transducer of a system emit (or are configured to emit) greater acoustic energy in one or more directions in relation to one or more other directions.

According to some embodiments, an ultrasound transducer includes differing wall thickness (e.g., along its longitudinal axis). In embodiments comprising two or more transducers, the wall thickness of one transducer is greater or less than the wall thickness of another transducer. In some embodiments, one or more transducers of a system can be independently controllable (e.g., such that power and/or frequency to one transducer can be different than power and/or frequency to another transducer, etc.). In some embodiments, two or more transducers of a system are controlled together or in unison. In one embodiment, a transducer can include an eccentric or non-uniform backing lumen or opening.

According to some embodiments, the transducer comprises a varying wall thickness along at least a portion of its circumferential extent. Accordingly, rotating the transducer can alter the acoustic energy pattern emitted by the transducer and/or alter one or more other aspects of energy emission (e.g., frequency, efficiency, etc.) during use. In some embodiments, one or more regions, surfaces and/or other portions of a transducer can be at least partially masked, covered, obstructed, etc. in order to alter the acoustic energy profile of the transducer during use. In one embodiment, at least a portion of the transducer is masked or otherwise covered by selective plating and/or etching of the electrodes along the transducer, covering a portion of the transducer, using one or more features of the balloon, etc.).

According to some embodiments, ultrasonic energy is directed directly within the tissue of the targeted nerve tissue (e.g., sympathetic nerves). In any of the embodiments disclosed herein, a balloon and/or other expandable structure or member can be used to at least partially expand the area or volume of tissue being treated (e.g., the renal artery, other body lumen or vessel, etc. can be radially expanded). In some embodiments, an ablation system includes a balloon (e.g., positioned at least partially around one or more transducers), but no fluid is configured to be circulated through the balloon during use. In one embodiment, the balloon can be inflated with one or more gases, liquids and/or fluids (e.g., in order to expand the balloon, so that balloon contacts the adjacent wall of the targeted vessel, so that the one or more transducers of the system are radially centered or generally radially centered within the vessel, etc.), but no fluids are circulated through the balloon. In some embodiments, the balloon is configured to maintain an inflated or expanded state without the continuous or intermittent delivery of fluid therethrough.

In some embodiments, a catheter of the system comprises a chip (e.g., a smart catheter) and/or one or more related components or features (e.g., an identification device or reader, a transducer, etc.). In one embodiment, a generator can detect which catheter is being used. In some embodiments, the system can monitor one or more aspects of a therapy or procedure using one or more metrics that are detected, such as, for example, pressure, temperature, flow-rate, vessel diameter, thermal profile, presence and/or degree of spasm of a vessel, degree of narrowing of a vessel and/or the like. In some embodiments, such information is used in a control scheme to regulate one or more aspects of the generator and/or other components or devices of the system (e.g., to modulate power, frequency, duration of procedure, automatic shutoff, billing, patient records or other record-keeping, memorization of a procedure for other reasons, etc.).

According to some embodiments, the at least one fluid lumen of the catheter includes an axis that is eccentric to the central axis of the catheter (e.g., one or more fluid lumens are not oriented along or near the central or longitudinal axis of the catheter). According to some embodiments, the at least one fluid lumen comprises a non-circular shape to increase the cross-sectional area of the at least one fluid lumen. In one embodiment, the at least one fluid lumen includes a circular shape along the periphery of the catheter. In some embodiments, the at least one fluid lumen comprises a fluid delivery lumen and a fluid return lumen.

According to some embodiments, the catheter comprises an over-the-wire design such that the guidewire lumen extends from a proximal end to the distal end of the catheter. In some embodiments, the catheter comprises a rapid exchange design such that the guidewire lumen is located only along a distal portion of the catheter. In one embodiment, a proximal portion of the catheter that does not include a guidewire lumen comprises a groove or recess along an exterior surface of the catheter, wherein the groove or recess is configured to receive a guidewire therein.

According to some embodiments, the distal end of the catheter is attached to a balloon, wherein the at least one fluid lumen is in fluid communication with an interior of the balloon to enable fluids to be delivered to and/or from the interior of the balloon through the at least one fluid lumen. In some embodiments, the catheter further includes an energy delivery device (e.g., ultrasound device, RF electrode, microwave device, etc.) located at least partially within the balloon. In some embodiments, the catheter comprises a 5 French or 6 French catheter.

According to some embodiments, an intraluminal (e.g., intravascular), ultrasound-based ablation system comprises a catheter comprising at least one fluid lumen and a guidewire lumen, wherein the guidewire lumen is not positioned along the cross-sectional centerline of the catheter, and a balloon positioned along a distal end of the catheter, an interior of the balloon being in fluid communication with the at least one fluid lumen of the catheter, wherein the balloon is configured to inflate when fluid is delivered into the interior through the at least one lumen of the catheter. The system further includes an ultrasound transducer positioned within the balloon, a distal tip comprising a central passage, wherein the balloon is positioned between the catheter and the distal tip and an electrically non-conductive member extending from the guidewire lumen to the central passage of the distal tip, the electrically non-conductive member positioned through an interior of the ultrasound transducer and configured to receive a guidewire. The system additionally comprises a backing member positioned between the electrically non-conductive member and the ultrasound transducer, the backing member being configured to support the ultrasound transducer. In some embodiments, the system comprises one or more centering assemblies positioned proximal to the catheter between the distal end of the catheter and the distal tip. In some embodiments, the centering assembly comprises a center opening or passage configured to receive the electrically non-conductive member, wherein the radial orientation of the center opening is offset relative to the radial orientation of the guidewire lumen of the catheter, wherein the center opening of the centering assembly is aligned with the cross-sectional centerline of the catheter and the balloon so as to radially center the ultrasound transducer when a guidewire is positioned through the electrically non-conductive member.

According to some embodiments, the electrically non-conductive member comprises polyimide. In some embodiments, the centering assembly comprises a plurality of wings extending radially outwardly from the center opening, the wings configured to engage an inner surface of the balloon. In one embodiment, the centering assembly comprises at least three wings. According to some embodiments, the centering assembly a plurality of wings that are evenly or unevenly distributed around the circumference of the assembly (e.g., spaced apart at 90° or 120° intervals). In other embodiments, a centering assembly can include fewer (e.g., 1, 2) or more (e.g., 4, 5, 6, more than 6, etc.) than 3 wings. According to some embodiments, the outer diameter of the centering assembly (e.g., taken along the outermost portions of the wings) is identical or substantially identical (e.g., within about 0-1%, 1-2%, 2-3%, 3-4%, 4-5%, more than 5%) of the outer diameter of the catheter. In some embodiments, the centering assembly comprises one or more suitable materials (e.g., thermoplastics, metals, alloys, combinations thereof, etc.).

In some embodiments, the balloon 14 (e.g., including the proximal portion 15, the main radially expandable portion, etc.) is extruded from a single material or member. In some embodiments, the proximal portion of the balloon can comprise a greater thickness of the extruded material or portion relative to the distal portions of the balloon. In some embodiments, the thickness of the proximal portion of the balloon is greater than the thickness of more distally located portions (e.g., along the main, radially expandable portion of the balloon) by about 0-10%, 10-20%, 20-30%, 30-40%, 40-50%, 50-60%, 60-70%, 70-80%, 80-90%, 90-100%, 100-125%, 125-150%, 150-200%, greater than 200%, percentages between the foregoing values and/or the like. In some embodiments, the distal portion of the balloon includes a generally cylindrical portion that is configured to maintain its shape during use (e.g., when cooling fluid is circulated through the balloon interior). In some embodiments, the proximal and distal portions of the balloon can be secured to the catheter and the tip, respectively, using one or more attachment methods or devices (e.g., adhesives, pressure or friction fit connections, fasteners, etc.).

According to some embodiments, in order to transition from a peripheral lumen of the catheter to the central opening of the centering assembly, the guidewire is angled through a portion of the catheter system (e.g., between the distal end of the catheter and the proximal end of the centering assembly). The guidewire can be angled within the proximal, cylindrical portion of the balloon at angle $\Theta$, which, in some embodiments, is about 0-40° (e.g., about 0-5°, 5-10°, 10-15°, 15-20°, 20-25°, 25-30°, 30-35°, 35-40°, angles between the foregoing, etc.). In some embodiments, the angle $\Theta$ is greater than about 40° (e.g., about 40-50°, 50-60°, greater than 60°, etc.).

In some embodiments, the cross-sectional area of each of the fluid lumens of the catheter is about 0.00005 to 0.00012 square inches (e.g., 0.00005 to 0.00006, 0.00006 to 0.00007, 0.00007 to 0.00008, 0.00008 to 0.00009, 0.00009 to 0.00010, 0.00010 to 0.00011, 0.00011 to 0.00012 square inches, areas between the foregoing, etc.), less than about 0.00005 square inches, more than about 0.00012 square inches for a 6 French catheter, and about 0.00003 to 0.00010 square inches (e.g., 0.00003 to 0.00004, 0.00004 to 0.00005, 0.00005 to 0.00006, 0.00006 to 0.00007, 0.00007 to 0.00008, 0.00008 to 0.00009, 0.00009 to 0.00010 square inches, areas between the foregoing, etc.), less than about 0.00003 square inches, more than about 0.00010 square inches for a 5 French catheter. In some embodiments, by eliminating a central lumen (e.g., a central guidewire lumen) within the catheter, the size of one or more of the other lumens (e.g., the fluid lumens) can be increased.

In some embodiments, the at least one fluid lumen comprises a fluid delivery lumen and a fluid return lumen. In some embodiments, the catheter further comprises an electrical conductor lumen, wherein each of the electrical conductor lumen and the at least one fluid lumen is not positioned along the cross-sectional centerline of the catheter.

According to some embodiments, the guidewire lumen is positioned along an entire length of the catheter. In some embodiments, the guidewire lumen is positioned only along a distal portion of the catheter, so that the catheter comprises a rapid exchange type catheter. In one embodiment, the catheter comprises a groove or recess along at least a proximal length of the catheter that does not comprise a guidewire lumen, the groove being configured to at least partially receive an adjacent guidewire. In some embodiments, the catheter comprises a 5 French or 6 French catheter. In some embodiments, the system is configured to be advanced into a subject via femoral or radial access. In one embodiment, the at least one fluid lumen comprises a non-circular shape (e.g., oval, triangular, irregular, etc.).

In some embodiments, the catheter includes a rapid-exchange design in which the catheter comprises a guidewire lumen only partially along its length. In one embodiment, the guidewire lumen extends only through the distal-most portion of the catheter (e.g., along a length immediately proximal to the balloon). In some embodiments, the catheter comprises an interior guidewire lumen only along the last 5 to 30 cm (e.g., 5-6, 6-8, 8-10, 10-12, 12-14, 14-16, 16-18, 18-20, 20-25, 25-30 cm, lengths between the foregoing, etc.) of the catheter's distal end. In some embodiments, the catheter comprises a guidewire lumen only along 0-30% (e.g., 0-5%, 5-10%, 10-15%, 15-20%, 20-25%, 25-30%, percentages between the foregoing, etc.) of its length (e.g., the distal end of catheter).

According to some embodiments, an intravascular, ultrasound-based ablation system comprises a catheter including at least one fluid lumen, a guidewire lumen and an electrical cable lumen, wherein each of the at least one fluid lumen, the guidewire lumen and the electrical cable lumen is not positioned along the cross-sectional centerline of the catheter (e.g., the electrical cable lumen is eccentric relative to the longitudinal or central axis of the catheter). In some embodiments, the system additionally comprises a balloon positioned along a distal end of the catheter, wherein an interior of the balloon is in fluid communication with the at least one fluid lumen of the catheter, and wherein the balloon is configured to inflate when fluid is delivered into the interior through the at least one lumen of the catheter. In some embodiments, the system further comprises an ultrasound transducer (e.g., a cylindrical transducer) positioned within the balloon, a distal tip, wherein the balloon is positioned between the catheter and the distal tip, and an electrically non-conductive member extending distally from the guidewire lumen through an interior of the ultrasound transducer, the electrically non-conductive member being configured to receive a guidewire. In some embodiments, the system further includes a centering assembly positioned proximal to the catheter between the distal end of the catheter and the distal tip, the centering assembly comprising a center opening configured to receive the electrically non-conductive member, wherein the center opening of the centering assembly is aligned with the cross-sectional centerline of the catheter and the balloon so as to radially center the ultrasound transducer when a guidewire is positioned through the electrically non-conductive member.

According to some embodiments, the electrically non-conductive member comprises polyimide. In some embodiments, the centering assembly comprises a plurality of wings extending radially outwardly from the center opening, the wings configured to engage an inner surface of the balloon. In one embodiment, the guidewire lumen is positioned along an entire length of the catheter. In some embodiments, the guidewire lumen is positioned only along a distal portion of the catheter, so that the catheter comprises a rapid exchange type catheter. In some embodiments, the catheter comprises an exterior groove along at least a proximal length of the catheter, the groove being configured to at least partially receive an adjacent guidewire.

According to some embodiments, an intravascular, ultrasound-based ablation system includes a catheter comprising a guidewire lumen, at least one cable lumen and at least one fluid lumen, and a balloon or other expandable structure or member positioned at a distal end of the catheter, wherein an interior of the balloon is in fluid communication with the at least one fluid lumen of the catheter. In some embodiments, the balloon is configured to inflate when fluid (e.g., cooling fluid) is delivered into the interior through the at least one fluid lumen of the catheter. The system further comprises a tip extending distally from a distal end of the balloon, wherein the tip comprises an internal guidewire passage, and one or more ultrasound transducers positioned within the balloon. In some embodiments, the ultrasound transducer includes a cylindrical tube with inner and outer surfaces, each of the inner and outer surfaces comprising an electrode, wherein the ultrasound transducer defines an internal space adjacent the inner electrode surface, the internal space being in fluid communication with the interior cavity of the balloon so that, when in use, fluid entering the balloon passes along both the inner and outer surfaces to transfer heat away from the ultrasound transducer.

In some embodiments, at least one electrical cable (e.g., coaxial cable) is routed or otherwise positioned within the at least one cable lumen of the catheter, wherein the at least one electrical cable is electrically coupled to the electrodes along the inner and outer surfaces of the ultrasound transducer. The system further includes a backing member or post extending from the catheter to the tip and connecting the catheter with the tip. In some embodiments, the backing member is positioned within the internal space of the ultrasound transducer, wherein the backing member comprises a central opening that is generally aligned with the guidewire lumen of the catheter and the internal guidewire passage of the tip to permit the system to be delivered to a desired vascular position over a guidewire. In some embodiments, the backing member serves as a fluid barrier between fluid circulated within the balloon interior and the central opening.

According to some embodiments, the backing member comprises an electrically insulating material (e.g., polyimide, another polymeric material, etc.) along an interior surface of the central opening of the backing member so as to prevent electrical conduction between a guidewire and the backing member. In some embodiments, the guidewire lumen extends from a proximal end of the catheter to the balloon. In other embodiments, the guidewire lumen extends from a location between the proximal and distal ends of the catheter to the distal end of the catheter, such that the catheter comprises a rapid exchange design.

According to some embodiments, an intravascular, ultrasound-based ablation system comprises a catheter having at least one cable lumen and at least one fluid lumen, a balloon or other expandable structure positioned at a distal end of the catheter, an interior of the balloon being in fluid communication with the at least one fluid lumen of the catheter and an ultrasound transducer positioned within the balloon, wherein the ultrasound transducer comprises a cylindrical tube having a proximal end and a distal end and inner and outer surfaces. In some embodiments, each of the inner and outer surfaces comprises an electrode, wherein the proximal end of the cylindrical tube comprising a stepped portion, and wherein a portion of the outer diameter formed by the outer surface of the cylindrical tube is smaller than a portion of the outer diameter of the cylindrical tube located distal to the stepped portion. The system further comprises at least one electrical cable positioned within the at least one cable lumen of the catheter, the at least one electrical cable being configured to supply electrical power to the ultrasound transducer, wherein the at least one electrical cable comprises a first conductor and a second conductor.

In some embodiments, the system further comprises one or more stand-off assemblies located within an interior and along or near the proximal end of the cylindrical tube of the ultrasound transducer. In one embodiment, the stand-off assembly is electrically conductive and in contact with, at least intermittently, the electrode along the inner surface of the cylindrical tube of the ultrasound transducer, wherein the first conductor is connected to an exterior of the cylindrical tube along the stepped portion, and wherein the second conductor is connected to the stand-off assembly so that the second conductor is electrically coupled to the electrode along the inner surface of the cylindrical tube. The system further comprise a ring surrounding the stepped portion of the cylindrical tube, the ring being sized and shaped to surround the portion of the outer diameter of the cylindrical tube located distal to the stepped portion, wherein the ring is electrically conductive so that the first connector is electrically coupled to the electrode along the outer surface of the cylindrical tube, and wherein the ring allows for more uniform electrical loading of the ultrasound transducer when the electrical transducer is energized.

According to some embodiments, the ring comprises conductive solder. In some embodiments, the ring comprises a conductive machined ring or other member or feature that couples around the stepped portion of the cylindrical tube. In some embodiments, the stepped portion extends approximately 5% to 25% (e.g., 5% to 10%, 10% to 15%, 15% to 20%, 20% to 25%, etc.) of a length of the cylindrical tube. In one embodiment, the stepped portion comprises a portion of the cylindrical tube that is removed using grinding or other removal techniques. In some embodiments, an impedance of the at least one electrical cable substantially matches an impedance of the ultrasound transducer. In some embodiments, the impedance of the electrical cable and the ultrasound transducer is approximately 40 to 60 ohms (e.g., 50, 40-42, 42-44, 44-46, 46-48, 48-50, 50-52, 52-54, 54-56, 56-58, 58-60 ohms, etc.). In some embodiments, the diameter or other cross-sectional dimension of the stepped portion 68a is 50-95% (e.g., 50-55, 55-60, 60-65, 65-70, 70-75, 75-80, 80-85, 85-90, 90-95%, percentages between the foregoing ranges, etc.) of the outer diameter 66a of the transducer. In other embodiments, the diameter or other cross-sectional dimension of the stepped portion 68a is less than 50% (e.g., 20-30, 30-40, 40-50%, percentages between the foregoing ranges, less than 20%, etc.) or greater than 95% (e.g., 95-96, 96-97, 97-98, 98-99, 99-100%, percentages between the foregoing ranges, etc.) of the outer diameter 66a of the transducer.

According to some embodiments, the electrical impedance of the electrical conductors (e.g., the one or more electrical cables that electrically couple the transducer to the power supply) can be matched or substantially matched (e.g., within about 0-10%, 0.1%, 0.2%, 0.3%, 0.4%, 0.5%, 0.5-1%, 1-2%, 2-3%, 3-4%, 4-5%, 5-6%, 6-7%, 7-8%, 8-9%, 9-10%, etc.) to the electrical impedance of the ultrasound transducer.

According to some embodiments, an intravascular, ultrasound-based ablation system comprises a catheter having a cable lumen extending from a proximal end to a distal end of the catheter, an ultrasound transducer positioned at or near a distal end of the catheter, wherein the ultrasound transducer comprises a cylindrical tube with inner and outer surfaces, wherein each of the inner and outer surface comprising an electrode. The system further comprises a backing member or post extending from the distal end of the catheter and positioned within an interior of the ultrasound transducer, wherein the backing member is configured to support the ultrasound transducer, and wherein the backing member is electrically coupled to the electrode along the inner surface of the cylindrical tube of the ultrasound transducer. In some embodiments, the system comprises an electrical cable positioned within the cable lumen of the catheter and extending from the proximal end to the distal end of the catheter, wherein a proximal end of the electrical cable is coupled to a generator configured to selectively provide electrical power to the ultrasound transducer through the electrical cable. In one embodiment, the electrical cable comprises a first electrical connector and a second electrical connector, wherein the first connector is electrically coupled to the electrode along the outer surface of the ultrasound transducer, and wherein the second connector is electrically coupled to the backing member and the electrode along the inner surface of the ultrasound transducer. In some embodiments, an impedance of the electrical cable is substantially equal to an impedance of the ultrasound transducer, thereby providing a more efficient power transfer from the generator to the ultrasound transducer when the ablation system is in use.

According to some embodiments, the electrical cable comprises a coaxial cable. In one embodiment, the backing member or post comprises at least one stand-off assembly that electrically couples the backing member to the electrode along the inner surface of the cylindrical tube of the ultrasound transducer. In some embodiments, the backing member or post is coupled to both the proximal and the distal ends of the transducer. In some embodiments, the impedance of the electrical cable and the ultrasound transducer is approximately 40 to 60 ohms (e.g., approximately 50 ohms). In some embodiments, the first connector of the electrical cable is electrically coupled to the electrode while not physically attached to the outer surface of the ultrasound transducer.

According to some embodiments, an intravascular, ultrasound-based ablation system includes a catheter comprising at least one fluid lumen, a balloon or other expandable member positioned at a distal end of the catheter, wherein an interior of the balloon is in fluid communication with the at least one fluid lumen of the catheter, and wherein the balloon is configured to inflate when fluid is delivered into the interior through the at least one lumen of the catheter. The system further comprises an ultrasound transducer positioned within the balloon, wherein the ultrasound transducer includes a cylindrical tube with inner and outer surfaces, wherein each of the inner and outer surface comprising an electrode. In some embodiments, the ultrasound transducer defines an internal space adjacent the inner electrode surface, wherein the internal space is in fluid communication with the interior cavity of the balloon so that, when in use, fluid entering the balloon passes along both the inner and outer surfaces to cool the ultrasound transducer. In some embodiments, the system additionally comprises a fluid transfer device configured to selectively deliver a cooling fluid within the balloon when the ultrasound transducer is activated in order to transfer heat away from the ultrasound transducer during use, wherein the fluid transfer device comprises a reservoir for storing a volume of cooling fluid and a movable member configured to move within an interior of the reservoir in order to transfer cooling fluid through the at least one fluid lumen of the catheter to the balloon, and wherein the reservoir is sized to store sufficient cooling fluid for an entire ablation procedure.

In some embodiments, cooling fluid is circulated through the system in such a manner so that the temperature along the interior wall of the vessel surrounding the transducer is maintained at a temperature of about 50-55° C. (e.g., 50° C., 51° C., 52° C., 53° C., 54° C., 55° C., etc.). In other embodiments, the target temperature can be below 50° C. (e.g., 30-35° C., 35-40° C., 40-45° C., 45-50° C., temperatures between the foregoing ranges, less than 30° C., etc.) or greater than 55° C. (e.g., 55-60° C., 60-65° C., 65-70° C., 70-75° C., temperatures between the foregoing ranges, greater than 75° C., etc.). In addition, in some embodiments, the temperature of the vessel wall is maintained within such a target range (e.g., 50-55° C., 30-75° C., etc.), while the temperature of tissue approximately 0.5 mm to 8 mm (e.g., 1 mm to 6 mm, where, in some embodiments, target tissue is located) is heated to about 60-80° C. (e.g., 60-70° C., 70-80° C., 65-75° C., etc.), 50-100° C. (e.g., 50-60° C., 60-70° C., 70-80° C., 80-90° C., 90-100° C., temperatures between the foregoing ranges, etc.), greater than 100° C., when the transducer is activated.

In some embodiments, the volume of the reservoir is approximately 50 ml to 1,000 ml (e.g., 50-100, 100-200, 200-300, 300-400, 400-500, 500-600, 600-700, 700-800, 800-900, 900-1,000 ml, capacities between the foregoing, etc.). In other embodiments, the volume of the reservoir is less than 50 ml (e.g., 20-30, 30-40, 40-50 ml, volumes between the foregoing ranges, less than 20 ml) or greater than 1,000 ml (e.g., 1,000-1,100, 1,100-1,200, 1,200-1,300, 1,300-1,400, 1,400-1,500, 1,500-2,000, 2,000-3,000, 3,000-5,000 ml, volumes between the foregoing ranges, greater than 5,000 ml, etc.).

According to some embodiments, the movable member is coupled to a motor for selectively advancing the movable member relative to the reservoir. In one embodiment, the motor comprises a stepper motor or another type of motor. In some embodiments, the fluid transfer device comprises a syringe pump. In some embodiments, the catheter comprises a fluid delivery lumen and a fluid return lumen, wherein cooling fluid is delivered to the balloon from the fluid transfer device via the fluid delivery lumen, and wherein cooling fluid is withdrawn from the balloon via the fluid return lumen. In some embodiments, the fluid transfer lumen is in fluid communication with a first fluid transfer device, and wherein the fluid return lumen is in fluid communication with a second fluid transfer device, wherein both the first and the second fluid transfer devices are operated simultaneously to circulate cooling fluid through the balloon during an ablation procedure. In some embodiments, the fluid transfer device is configured to deliver cooling fluid through the at least one fluid lumen of the catheter and into the balloon at a flowrate of 30-50 ml/min (e.g., 30-40 ml/min, 40-50 ml/min, 35-45 ml/min, 40 ml/min). In other embodiments, the fluid transfer device is configured to deliver cooling fluid through the at least one fluid lumen of the catheter and into the balloon at a flowrate of less than 30 ml/min (e.g., 0-10, 10-20, 20-25, 25-30 ml/min, flowrates between the foregoing, etc.) or greater than 50 ml/min (e.g., 50-60, 60-70, 70-80, 80-90, 90-100 ml/min, flowrates between the foregoing, greater than 100 ml/min, etc.).

A method of intraluminally ablating or otherwise neuromodulating nerve tissue using an ultrasound-based ablation system includes advancing a catheter of the ablation system intraluminally to a target anatomical location of a subject, wherein the system comprises a balloon positioned at a distal end of the catheter, an interior of the balloon being in fluid communication with at least one fluid delivery lumen and at least one fluid return lumen of the catheter, wherein an ultrasound transducer is positioned within the interior of the balloon. The method further includes circulating cooling fluid through the interior of the balloon by transferring cooling fluid from a fluid transfer device through the at least one fluid lumen of the catheter and transferring cooling fluid away from the interior of the balloon through the at least one fluid return lumen and activating the ultrasound transducer positioned within the balloon to ablate nerve tissue adjacent to the target anatomical location of the subject. In some embodiments, cooling fluid is circulated adjacent the ultrasound transducer within the balloon when the ultrasound transducer is activated. In some embodiments, the fluid transfer device comprises a reservoir for storing a volume of cooling fluid and a movable member configured to move within an interior of the reservoir in order to transfer cooling fluid through the at least one fluid lumen of the catheter to the balloon, wherein the reservoir is sized to store sufficient cooling fluid for an entire ablation procedure.

According to some embodiments, the movable member (e.g., plunger) is coupled to a motor for selectively advancing the movable member relative to the reservoir. In one embodiment, the motor comprises a stepper motor or another type of motor or actuator. In some embodiments, the fluid transfer device comprises a syringe pump or another type of pump. In some embodiments, cooling fluid is circulated through the balloon at a flowrate of 30-50 ml/min (e.g., 30-40 ml/min, 40-50 ml/min, 35-45 ml/min, 40 ml/min, etc.).

According to some embodiments, a coupling configured for use in an outlet of a fluid container (e.g., IV bag) includes a hub configured to abut against the outlet of the coupling, wherein the hub is configured to prevent over-insertion of the coupling into the fluid container. In some embodiments, a proximal end of the hub comprises a fitting configured for attachment to a fluid conduit. The coupling further comprises a spike portion extending distally from the hub, wherein a length of the spike is 0.5 inches to 3 inches. In some embodiments, the coupling comprises at least two fluid lumens (e.g., 2, 3, 4, 5, more than 5, etc.) that extend throughout an entire length of the coupling from the proximal end of the hub to a distal end of the spike, wherein the lumens place an interior of the fluid container in fluid communication with at least one fluid conduit secured to the hub. In some embodiments, the coupling permits at two different fluid sources to be placed in fluid communication with an interior of a fluid container comprising only a single outlet. In some embodiments, such a coupling or spike can be used on an IV bag or other fluid container that is placed in fluid communication with a syringe pump of a treatment system. Thus, the IV bag can be configured to store additional fluid that will be delivered through a delivery lumen into a balloon and/or can be configured to store excess fluid being returned from the balloon via a return lumen in the catheter. Thus, the coupling can be placed in fluid communication with the catheter and/or the syringe pump of the treatment system. In some embodiments, the inner diameters of the internal lumens or passages of the spike or coupling are approximately 0.05 to 0.125 inches (e.g., 0.05-0.06, 0.06-0.07, 0.07-0.08, 0.08-0.09, 0.09-0.1, 0.1-0.11, 0.11-0.125 inches, diameter between the foregoing, etc.) and the minimum penetration distance 80 is about 1.5 inches (e.g., 0.75, 1.0, 1.25, 1.5 inches, distances between the foregoing, less than 0.75 inches, more than 1.5 inches, 1.5-2.0 inches, 2.0-3.0 inches, more than about 3 inches, etc.).

In some embodiments, the spike includes a taper along at least a portion of its length, so that a cross-sectional dimension of the spike is smaller along the distal end of the spike than a cross-sectional dimension of the spike along a proximal end of the spike. In some embodiments, the spike comprises a cone-shaped, with either a linear or non-linear (e.g., curved) profile. In some embodiments, the spike is configured for placement into an IV bag comprising only a single outlet or port. In some embodiments, the coupling comprises two fluid lumens.

The methods summarized above and set forth in further detail below describe certain actions taken by a practitioner; however, it should be understood that they can also include the instruction of those actions by another party. Thus, actions such as "advancing a catheter intraluminally" or "activating a transducer" include "instructing advancing a catheter intraluminally" and "instructing activating a transducer."

BRIEF DESCRIPTION OF THE DRAWINGS

FIG. 2 illustrates a detailed side view of a distal end of the system depicted in FIG. 1.

FIG. 3 illustrates a side cross-sectional view of the distal end of an ultrasound-based system according to one embodiment.

FIG. 4 illustrates a section view across a portion of the system of FIG. 3.

FIG. 5 illustrates a partial cross-sectional view of the expandable member and ultrasound transducer according to one embodiment.

FIG. 6 illustrates a partial cross-sectional view of the ultrasound transducer of FIG. 5.

FIG. 7 illustrates the fluid lumens of an ultrasound-based system according to one embodiment.

DETAILED DESCRIPTION

Figure 1:
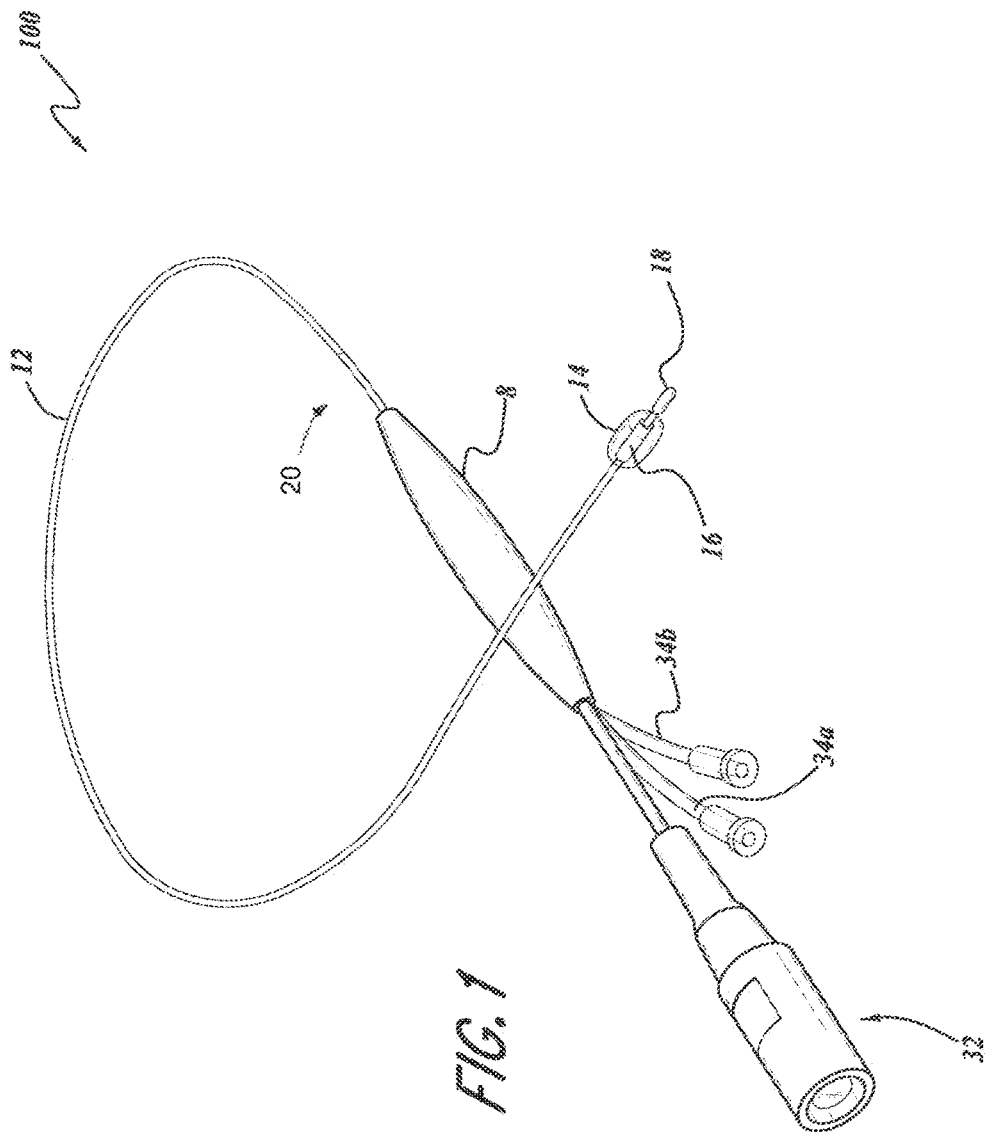
FIG. 1 illustrates an ultrasound-based treatment system according to one embodiment.

In the various embodiments described herein, catheter-based systems and methods for treating targeted tissue of a subject are disclosed. The systems and methods are particularly useful in neuromodulation procedures (e.g., denervation). For example, as discussed in greater detail herein, the systems can be used to target select nerve tissue of the subject. Targeted nerve tissue can be heated by the application of ultrasonic energy thereto in order to neuromodulate (e.g., ablate, necrose, stimulate, etc.) the tissue. In other embodiments, the application of ultrasonic energy can be used to target other adjacent tissue of a subject, either in lieu of or in addition to nerve tissue. Accordingly, the systems and methods disclosed herein can be used to treat hypertension, other nerve-mediated diseases and/or any other ailment. The systems and methods disclosed herein can also be used in ablative procedures of non-nerve tissue (including, but not limited to, tumors, cardiac tissue, and other tissue types). Arrhythmias are treated according to one embodiment.

The catheter-based systems disclosed herein can be delivered intraluminally (e.g., intravascularly) to a target anatomical region of the subject, such as, for example, the renal artery, another targeted vessel or lumen, etc. Once properly positioned within the target vessel, the ultrasound transducer can be activated to selectively deliver acoustic energy radially outwardly from a distal end of the system and toward the targeted tissue. The transducer can be activated for a particular time period and at a particular energy level (e.g., power, frequency, etc.) in order to accomplish the desired effect on the targeted tissue (e.g., to achieve a target temperature). In embodiments where the targeted tissue is nerve tissue, the systems are configured to deliver ultrasonic energy through the adjacent wall of the vessel in which the system is positioned. For example, with respect to the renal artery, targeted nerve tissue is typically located about 0.5 mm to 8 mm (e.g., about 1 mm to 6 mm) from the vessel wall. In some embodiments, nerve tissue is located 0.5, 1, 1.5, 2, 2.5, 3, 3.5, 4, 4.5, 5, 5.5, 6, 6.5, 7, 7.5, 8 mm, distances between the foregoing, away from the interior wall of the vessel. In other embodiments, nerve tissue can be located less than 0.5 mm or greater than 8 mm from the interior wall of the vessel. Accordingly, ultrasonic energy can be used to heat the nerve tissue to at least partially neuromodulate the nerve tissue. As used herein, neuromodulation shall be given its ordinary meaning and shall include, without limitation, complete or partial ablation, necrosis, stimulation and/or the like. In some embodiments, the acoustic energy is delivered radially outwardly from the ultrasound transducer, permitting the delivery of ultrasonic energy to target nerve tissue regardless of the radial orientation of such nerve tissue relative to a vessel (e.g., renal artery). In some embodiments, the acoustic energy is delivered along an entire, continuous circumference of the transducer. In other embodiments, however, the acoustic energy is emitted non-continuously or intermittently around the circumference of the transducer. Further, as discussed in greater detail herein, the various systems disclosed herein can be configured to deliver a cooling fluid to the anatomical region being treated in order to protect certain tissue of the subject (e.g., to prevent or reduce the likelihood of stenosis or other damage to the wall of the vessel through which energy is delivered during a procedure). For example, cooling fluid can be selectively delivered to and/or circulated within a balloon that at least partially surrounds the transducer.

General System Components and Features

FIGS. 1 and 2 illustrate an ultrasound-based ablation system 100 according to one embodiment. As shown, the system 10 can comprise a catheter 12 having a proximal end 20 and a distal end 22, an expandable member 14 (e.g., balloon) along the distal end of the catheter and one or more ultrasound transducers 16 positioned within the expandable member 14. A proximal portion of the system can comprise a handle 8 and one or more connectors or couplings (e.g., an electrical coupling 32 for connecting the system to a power generator, one or more ports 34 for placing the system in fluid communication with a cooling fluid, etc.).

In some embodiments, the catheter 12 includes one or more lumens that can be used as fluid conduits, electrical cable passageways, guidewire lumen and/or the like. For example, as illustrated in FIG. 5, the catheter 12 can include at least one cable lumen 24 that is shaped, sized and otherwise configured to receive an electrical cable 28 (e.g., coaxial cable, wire, other electrical conductor, etc.). The electrical cable 28 advantageously permits the electrode of the system's ultrasound transducer to be selectively activated in order to emit acoustic energy to a subject.

The catheter 12 can also include at least one fluid lumen 26 for transferring cooling fluid (e.g., water, saline, other liquids or gases, etc.) to and from the balloon or other expandable member 14 located at the distal end of the system. As discussed in greater detail herein, in some embodiments, the catheter comprises at least two fluid lumens 26, one for delivering cooling fluid to the balloon and the other for returning the cooling fluid from the balloon. However, the catheter 12 can include only a single fluid lumen or more than two fluid lumen (e.g., 3, 4, more than 4, etc.), as desired or required. As described in greater detail herein, the lumens can be located along any part of the cross-sectional area of the catheter (e.g., along the centerline, offset from the centerline, etc.) and/or can include any cross-sectional shape (e.g., circular, oval, rectangular or other polygonal, irregular, etc.), as desired or required.

As illustrated in FIGS. 2 and 3, the ultrasound transducer 16 can be positioned completely within an interior of the expandable member 14 (e.g., balloon). In some embodiments, as shown in FIG. 2, when expanded, the outer wall of the balloon 14 is generally parallel with the walls of the cylindrical ultrasound transducer 16. The balloon 14 can be a compliant, semi-compliant or non-compliant medical balloon, as desired or required. Thus, when inflated, the balloon or other expandable member that at least partially surrounds the transducer can at least partially contact the adjacent wall of the vessel. In some embodiments, however, one or more portions of the balloon are configured to not contact the adjacent vessel wall when expanded. In some embodiments, the ultrasound transducer 16 is liquid cooled along both its outer and inner electrodes, meaning that cooling liquid entering the balloon 14 is permitted to pass across both the exterior and interior surfaces of the cylindrical transducer to transfer heat away from the transducer. In some embodiments, the cooling liquid or other fluid can directly contact the exterior and/or interior surfaces of the transducer. The transducer 16 can include a reflective interface (e.g., along its interior) so as to permit ultrasonic energy generated at the inner electrode (e.g. along the interior surface of the cylindrical transducer) to be reflected radially outwardly.

Additional details regarding possible ultrasonic transducer designs and embodiments (e.g., both structurally and operationally) and/or catheter-based ultrasound delivery systems are provided in U.S. patent application Ser. No. 11/267,123, filed on Jul. 13, 2001 and published as U.S. Publ. No. 2002/0068885 on Jun. 6, 2002; U.S. patent application Ser. No. 09/905,227, filed Jul. 13, 2001 and issued as U.S. Pat. No. 6,635,054 on Oct. 21, 2003; U.S. patent application Ser. No. 09/904,620, filed on Jul. 13, 2001 and issued as U.S. Pat. No. 6,763,722 on Jul. 20, 2004; U.S. patent application Ser. No. 10/783,310, filed Feb. 20, 2004 and issued as U.S. Pat. No. 7,837,676 on Nov. 23, 2010; U.S. patent application Ser. No. 12/227,508, filed on Feb. 3, 2010 and published as U.S. Publ. No. 2010/0130892 on May 27, 2010; U.S. patent application Ser. No. 10/611,838, filed on Jun. 30, 2003 and published as U.S. Publ. No. 2004/0082859 on Apr. 29, 2004; and PCT Appl. No. PCT/US2011/025543, filed on Feb. 18, 2011 and published as PCT Publ. No. WO 2012/112165 on Aug. 23, 2012. The entireties of all the foregoing applications is hereby incorporated by reference herein and made a part of the present application.

With continued reference to FIG. 1, one or more electrical cables that supply electrical power to the transducer 16 can be coupled via the electrical coupling 32 located at the proximal end of the system. In some embodiments, the electrical coupling comprises a standard or non-standard connection to a power supply and controller (not illustrated). For example, in some embodiments, the electrical coupling 32 can be easily and quickly attached and detached to a power supply and controller. As is described in greater detail below, the fluid lumen(s) 26 of the catheter can be used to selectively transfer fluid (e.g., cooling fluid) between a fluid transfer device (e.g., fluid pump) and the interior of the balloon or other expandable member 14. The cooling fluid can be used to inflate the expandable member 14 and to provide cooling (e.g., when the ultrasound transducer 16 is activated) in order to transfer heat away from the ultrasound transducer 16 and/or the surrounding tissue of the subject during use.

The system 100 can be delivered to the target anatomical location (e.g., a renal artery) via femoral, radial or other intravascular access. The system can be delivered through the vasculature or other lumen of the subject either with or without the assistance of a guidewire. Accordingly, as discussed in greater detail below, the catheter and other components of the system can include a guidewire lumen or other passages to permit delivery over a guidewire. In other embodiments, a steerable catheter or sheath and/or any other guiding device or method can be used to deliver the system to the targeted anatomical location of the subject.

In some embodiments, the ultrasonic transducers are operated in a range of from 1 to 20 MHz (e.g., 1-5 MHz, 5-10 MHz, 10-15 MHz, 15-20 MHz, 8-10 MHz, other values or ranges within the foregoing, etc.). In one embodiment, for example, the ultrasound transducer of the system is configured to operate at a frequency of about 9 MHz. In other embodiments, however, the frequency at which a transducer is operated can be below 1 MHz (e.g., 0.1-0.2, 0.2-0.3, 0.3-0.4, 0.4-0.5, 0.5-0.6, 0.6-0.7, 0.7-0.8, 0.8-0.9, 0.9-1.0 MHz, frequencies between the foregoing ranges, less than 0.1 MHz, etc.) or above 20 MHz (e.g., 20-25, 25-30 MHz, frequencies between the foregoing ranges, above 30 MHz, etc.), as desired or required for a particular application or use. The power supplied to the ultrasound transducer can vary, as desired or required, and in some embodiments, is 5 to 80 Watts (e.g., 5 to 50, 5 to 10, 10 to 20, 20 to 30, 30 to 40, 40 to 50, 50 to 60, 60 to 70, 70 to 80 Watts, power levels between the foregoing ranges, etc.) at the transducer. As noted above, the period of time during which the ultrasound is activated for a particular treatment procedure can vary, and can also depend on one or more other factors, such as, for example, the power level at the transducer, the frequency of ultrasonic energy emitted, the size of the vessel or other tissue being treated, the age, weight and gender of the patient being treated and/or the like. However, in some embodiments, the ultrasonic transducer is activated for about 10 seconds to 5 minutes (e.g., 10-30 seconds, 30 seconds to 1 minute, 30 seconds to 5 minutes, 1 to 3 minutes, about 2 minutes, 10 seconds to 1 minute, 1 to 2 minutes, 2 to 3 minutes, 3 to 4 minutes, 4 to 5 minutes, time periods between the foregoing ranges, etc.). In other embodiments, the ultrasonic transducer is activated for less than 10 seconds (e.g., 0-1, 1-2, 2-3, 3-4, 4-5, 5-6, 6-7, 7-8, 8-9, 9-10 seconds, time periods between the foregoing ranges, etc.) or more than 5 minutes (e.g., 5-6, 6-7, 7-8, 8-9, 9-10, 10-15, 15-20 minutes, time periods between the foregoing, more than 20 minutes, etc.), as desired or required for a particular application or treatment protocol.

In some embodiments, the delivery of ultrasound energy during the execution of a treatment protocol is continuous or substantially continuous, e.g., without any interruptions or fluctuations in frequency, power, duty cycle and/or any other parameters. In other embodiments, however, the frequency, power, duty cycle and/or any other parameter is modified during the course of a procedure. For example, in some embodiments, the delivery of acoustic energy is modulated (e.g., between an on or off position, between a high and low level, etc.) to prevent or reduce the likelihood of overheating of adjacent (e.g., targeted or non-targeted tissue). Additional information regarding such modulation is provided in co-pending U.S. application Ser. No. 12/227,508, filed on Feb. 3, 2010 and published as U.S. Publication No. 2010/0130892 on May 27, 2010, the entirety of which is incorporated by reference herein and made part of the present application.

Referring now to FIG. 2, in several embodiments, the system can be delivered intravascularly through a subject so that the transducer is positioned within a target vessel (e.g., a renal artery) 36 and adjacent nerve tissue N to be neuromodulated. As shown, the expandable member (e.g., balloon) 14 can inflated (e.g., using a cooling fluid and/or any other fluid). Expansion of the balloon 14 can cause the wall of the balloon to at least partially engage the adjacent interior wall of the vessel 36. As discussed herein, however, in some embodiments, inflation of the balloon does not cause the balloon to contact the interior wall and/or any other portion of the adjacent vessel or lumen. In addition, in some embodiments, expansion of the balloon or other expandable member 14 causes the transducer 16 to be generally centered within the vessel. The ultrasound transducer 16 can be activated to generate ultrasonic energy that passes radially outwardly through the balloon and to the adjacent tissue of the subject. For example, the ultrasonic or acoustic energy can pass through the wall of the vessel 36 and heat the adjacent nerve tissue N. In some embodiments, sufficient energy is delivered to the nerve tissue N to cause a desired heating and/or other response. Thus, the energy delivered to the nerve tissue can neuromodulate (e.g., necrose, ablate, stimulate, etc.) the nerves, as desired or required.

Guidewire-Enabled Catheter System

As noted above, the ultrasound treatment systems described herein can be configured to be delivered to a target anatomical location of a subject with or without the use of a guidewire. FIG. 3 illustrates a cross-sectional view of the distal end of an ultrasound-based ablation system 100 that is configured to be delivered over a guidewire. As shown, the ultrasound transducer 16 can comprise a cylindrical tube 44 comprising a piezoelectric material (e.g., PZT, lead zirconate titanate, etc.) with inner and outer electrodes 46, 48 along the inner and outer surfaces of the cylindrical tube 44, respectively. When activated, the piezoelectric material vibrates transverse to the longitudinal direction of the cylindrical tube 44 (e.g., radially).

With continued reference to FIG. 3, the transducer 16 is generally supported within the interior of the balloon 14 using a backing member or post 56. As shown, the backing member 56 can extend from the catheter 12 to a distal tip 18. For example, in some embodiments, the backing member 56 is positioned within adjacent openings of the catheter and tip. Further, the balloon or other expandable member 14 can be secured along an exterior or other portion of the catheter and tip.

In order to permit liquid cooling along both the inner and outer electrodes 46, 48 of the transducer, the transducer can include one or more stand-off assemblies 50. As shown schematically in FIGS. 3 and 4, for example, the stand-off assemblies 50 can be positioned along or near each end of the transducer and couple the cylindrical portion of the transducer 16 to the backing member 56. The stand-off assemblies 50 can define one or more annular openings 55 through which cooling fluid may enter the interior space 52 of the cylindrical tube. One or more of the stand-off assemblies 50 can be electrically conductive so as to electrically couple the inner electrode 46 of the transducer 16 to the backing member or post 56. As discussed in greater detail herein, for example, in some embodiments, one or more conductors of the electrical cable 28 can be electrically coupled to the backing member 56. The conductors can be directly or indirectly coupled to the backing member, as desired or required. Thus, as the power generator is activated, current can be delivered from the cable 28 to the inner electrode 46 of the transducer via the post 56 and the stand-off assembly 50. According to one embodiment, this advantageously eliminates the need to electrically couple the cable directly to the inner electrode of the transducer.

With reference to FIG. 4, the stand-off assembly 50 can have a plurality of ribs or attachment points 54 that engage the inner electrode 46. The number, dimensions and placement of the ribs 54 can vary, as desired or required. For example, in some embodiments, as illustrated in FIG. 4, a total of three ribs 54 are generally equally-spaced apart from one another at an angle of 120°. However, in other embodiments, the quantity, shape, size, orientation, spacing and/or other details of the rigs or other attachment points can vary, as desired or required by a particular design or application.

With further reference to FIG. 3, the internal space 52 defined by the ultrasound transducer 16 can allow the piezoelectric material to vibrate both outwardly and inwardly in the transverse direction. As discussed herein, the internal space 52 of the transducer can be in fluid communication with the interior cavity 38 of the expandable member 14 so that, when in use, fluid entering the expandable member 14 can pass along and cool both the inner and outer surfaces of the ultrasound transducer 44. The cooling fluid can be used to maintain a desired temperature threshold along the interior wall of the vessel (e.g., renal artery) while allowing a higher temperature profile a particular distance radially away from the vessel wall. For example, such a configuration can permit ultrasonic energy to provide targeted heating to a specific location or zone located at a particular distance from the transducer. In some embodiments, such a configuration can advantageously permit targeted nerve tissue to be neuromodulated (e.g., necrosed, ablated, etc.) while protecting the vessel wall from unwanted harm or injury (e.g., stenosis, ablation or reconstruction, scarring, etc.). Likewise, for embodiments that treat tissue other than nerves, target tissue can be treated, while protecting non-target tissue.

According to some embodiments, as illustrated in FIGS. 3 and 4, the ultrasound-based ablation system 100 can be configured for delivery over a guidewire (e.g., regular guidewire, rapid-exchange system, etc.). Thus, the catheter can include a central guidewire lumen 60. In addition, other portions of the system can also include a lumen or other passage for receiving a guidewire. For example, the backing member or post 56 and the tip 18 can each comprise a central opening, lumen or passage 62, 64 that are generally aligned with the guidewire lumen 60 of the catheter. In one embodiment, the guide wire lumen 60 of the catheter 12 extends from the proximal end 20 of the catheter to the distal tip 18. Alternatively, a monorail guidewire configuration could be used, where the catheter rides on the wire just on the tip section distal to the transducer. In another embodiment, the guidewire lumen 58 extends from a location between the proximal 20 and distal 22 ends of the catheter to the distal end 22 of the catheter, such that the catheter comprises a rapid exchange design (e.g., one in which the guidewire lumen of the catheter does not extend to the proximal end of the catheter). In any of the embodiments disclosed herein, regardless of whether or not the system is configured for delivery over a guidewire, the catheter could comprise one or more pull wires or other features (e.g., steerable catheters or sheaths) that permit the system to be selectively manipulated (e.g., for selective deflection of the catheter) to aid in the delivery and placement within the subject, either in lieu of or in addition to a guidewire lumen.

In some embodiments, the backing member 56 advantageously serves as a fluid barrier between the cooling fluid circulated within the expandable member 14 and the central opening, lumen or passage 62 through which the guidewire is routed. In some embodiments, the backing member or post 56 can include one or more layers of an electrically insulating material or member 57 (e.g., polyimide, other polymeric or elastomeric material, other natural or synthetic material, etc.) along an interior surface of the central opening 62 of the backing member 56 so as to prevent or reduce the likelihood of electrical conduction between the guidewire 58 and the backing member 56. Such an electrically insulating member 57 can also provide one or more other benefits to the system, such as, for example, reduced friction between the guidewire and the post. As illustrated in FIG. 3, the various lumens or other openings of the catheter 12, backing member or post 56 and the distal tip 18 can be generally aligned and sized and shaped so at to allow a guidewire to freely and easily pass therethrough. Thus, the size, shape and other details of the lumens can be customized according to a particular application or use (e.g., based, at least in part, on the size of the catheter, the size of the guidewire, etc.).

Electrical Loading of Transducer

FIG. 5 illustrates a partial cross-sectional view of the expandable member (e.g., balloon) 14 and ultrasound transducer 16 of an ultrasound-based ablation system 100 according to one embodiment. As shown in FIG. 5, in some embodiments, the ultrasound transducer 16 comprises a uniform and cylindrical outer and inner diameters to provide for a uniform distribution of acoustic energy radially emanating therefrom (e.g., toward adjacent nerve tissue surrounding a vessel). In some embodiments, the outer and inner surfaces of the transducer 16 are coaxial and parallel with one another. Such a configuration can help ensure that a generally equal acoustic energy profile is delivered by the transducer during use. Accordingly, localized hotspots of ultrasonic energy, where a greater amount of heating is observed along one circumferential area and/or longitudinal area of the treatment region, are eliminated (or their likelihood is reduced). Further, as noted herein, adjacent portions of the balloon or other expandable member 14 can also include a uniform and/or flat profile upon expansion, such that outer and inner surfaces of the cylindrical transducer are generally parallel with the wall of the expanded balloon. Such a feature can help ensure that acoustic energy delivered by the transducer moves radially outwardly with little or no deflection at the balloon and/or the balloon-tissue interface.

In some embodiments, the acoustic energy profile of the transducer can be negatively affected by attaching anything to the outside and/or inside surfaces of the transducer tube (e.g., along the outer and/or inner electrodes of the transducer). For example, connecting an electrical conductor of the electrical cable that supplies current to the transducer can results in a diminished or undesirable acoustic energy profile. In such a configuration, for example, the wire or other electrical connection may be positioned along the outer surface of the electrode, which can disrupt the uniformity of such a surface and the uniformity of the acoustic energy pattern originating therefrom. Embodiments for eliminating the need to attach any electrical conductors or other leads to the outer and inner electrodes of a transducer are illustrated in, e.g., FIGS. 5, 6 and 6c.

In FIGS. 5 and 6, the cylindrical tube 44 can include a distal, non-stepped portion 66 and a proximal, stepped portion 68. As shown, the non-stepped portion comprises an outer electrode 48 along the exterior surface of the tube 44 and an inner electrode 46 along an interior surface of the tube. In some embodiments, the outer and/or inner electrodes can extend completely or partially along the length of the tube 44. As discussed in greater detail below, the non-stepped portion of the transducer 16 can comprise a vast majority of the transducer length, such as, for example, 50-95% or 60-90% (e.g., 50-60%, 60-70%, 70-80%, 80-90%, 90-95%, 90-99%, percentages between the foregoing ranges, etc.) of the overall length of the transducer 16. In other embodiments, however, the non-stepped portion can extend along less than 60% (e.g., 40-50%, 50-55%, 55-60%, less than 40%, etc.) or greater than 95% (e.g., 95-96, 96-97, 97-98, 98-99%, more than 99%, etc.) of the overall length of the transducer, as desired or required.

With continued reference to FIGS. 5 and 6, the proximal, stepped portion 68 includes an outer diameter 68a that is less than the outer diameter 66a of the non-stepped portion 66. In other words, the cylindrical tube 44 can comprise a step change in outer diameter along one of its ends (e.g., the proximal end). In the depicted embodiments, the stepped portion includes a generally flat or non-sloped step. However, in other embodiments, the step can include, without limitation, a sloped, non-flat, curved or rounded, undulating, roughened or otherwise uneven surface profile. Regardless of its exact shape and configuration, as shown in FIGS. 5 and 6, the stepped portion 68 of the tube can provide a surface on which a conductor of the electrical cable 28 can be positioned and/or to which it can attach. By placing an additional at least partially electrically conductive material or member along the outside of the conductor at the stepped portion of the tube, the cable can be advantageously electrically coupled to the outer electrode 48 of the transducer without attaching any conductors along an outer diameter or portion of the transducer. Accordingly, the cylindrical outer surface of the transducer can be maintained along the entire or substantially the entire length of the transducer to provide for a more even acoustic energy profile when the transducer is activated.

In some embodiments, the stepped portion 68 can be fabricated or otherwise manufactured by machining and/or grinding away a proximal portion of the tube's outer diameter 66a. As noted herein, such a step can include a uniform or constant outer diameter; however, in other embodiments, the stepped portion comprises a non-flat (e.g., rounded, curved, sloped, etc.) or irregular profile, as desired or required. In other embodiments, the stepped portion 68 can be fabricated or otherwise created by manufacturing the cylindrical tube 44 as a single piece of material with the step integrated into the tube during formation (e.g., by casting or molding the step into the original design). In yet another embodiment, the cylindrical tube 44 with the step can be created as two separate components (e.g., one with a larger diameter and one with the step diameter) which are bonded together (e.g., by welds, adhesives, rivets, screws, threaded couplings or features on the tube itself, press-fit connections, other mechanical or non-mechanical features, etc.).

In one embodiment, the cable 28 that supplies electrical current to the transducer comprises a coaxial cable having an inner conductor 28a and outer tubular conducting shield 28b. As shown in FIG. 6, the inner conductor 28a can be electrically coupled with the outer electrode 48 (e.g., via attachment to the stepped portion), while the outer tubular conducting shield 28b can be electrically coupled with the inner electrode 46 of the cylindrical tube 44. In other embodiments, the conductors of the coaxial cable can be reversed and/or different types of electrical cables or connectors can be used.

With continued reference to FIG. 5, one or more rings and/or other components 72 can be placed around the stepped portion 68 of the tube to form a generally constant outer diameter along an entire length of the transducer 16 (e.g., both along the stepped and non-stepped regions). For example, an electrically conductive ring 72 can surround the stepped portion 68 of the cylindrical tube 44 to electrically couple the outer electrode 48 to the inner conductor 28a. The ring 72 can be sized and shaped to have substantially the same outer diameter as the outer diameter 66a of the non-stepped portion 66 and provide a substantially continuous, flat and/or uniform outer surface for the entire transducer. In such an embodiment, the ring 72 can act as an active portion of the transducer 16 and allow for more uniform electrical loading of the ultrasound transducer when the electrical transducer is energized. The ring can be a machined ring having very precise dimensions. The ring, which comprises one or more metals or alloys (e.g., brass, stainless steel, etc.), can include a solid or partially-solid (e.g., having one or more hollow portions or area) design. The ring can include a uniform or unitary structure. Alternatively, in some embodiments, the ring or other member or components that is positioned along the outside of the stepped portion of the tube can include two or more pieces (e.g., 2, 3, 4, more than 4, etc.) that are configured to secure to one another when properly positioned relative to the stepped portion.

In other embodiments, one or more other components can be placed over the stepped portion 68 of the tube. For example, one or more layers of solder or other masses of at least partially electrically conductive can be deposited and secured to the outside of the stepped portion. Such layers or masses can include an outer diameter that matches the outer diameter 66*a* of the non-stepped portion 66 of the transducer. In some embodiments, an outer surface of the conductive electrical solder or other material or component placed along the outside of the stepped portion is reshaped or otherwise treated to achieve a substantially uniform overall outer diameter for the transducer (e.g., by mechanical grinding, etching, or polishing).

In some embodiments, the stepped portion 68 extends approximately 5% to 25% (e.g., 5% to 10%, 10% to 15%, 15% to 20%, 20% to 25%, etc.) of a length of the cylindrical tube 44. For example, the stepped portion 68 (and the corresponding ring, solder or other material or component placed around the stepped portion) can be approximately 1 mm in length, while the non-stepped portion 66 can be approximately 5 mm in length.

Alternatively, the cylindrical tube 44 can include a stepped portion 68 without an electrically conductive ring or other component 72. In such embodiments, the stepped portion 68 can form an inactive portion (or a partially inactive portion) of the transducer 16 and the distal, non-stepped portion 66 can form the active portion of the transducer 16. One or more electrical connections (e.g., wires, other conductors, traces, etc.) can be placed along the inactive stepped portion and be routed to the outer electrode of the non-stepped portion 66 of the transducer.

Figure 6A:
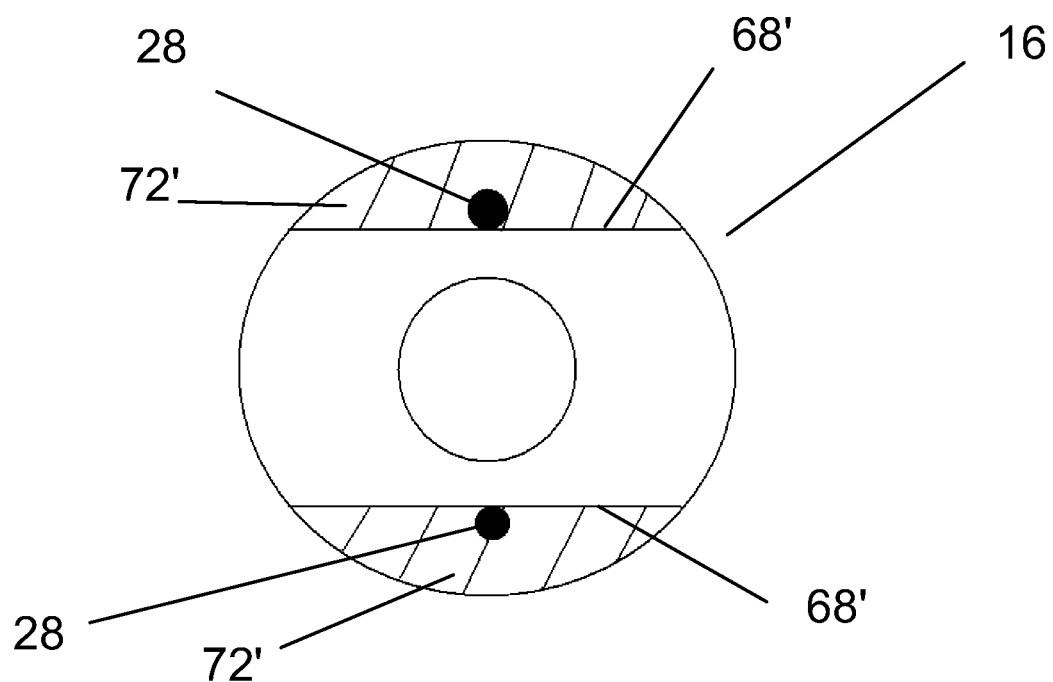
FIG. 6a illustrates a cross-sectional view of an ultrasound transducer having a stepped portion according to another embodiment.
Figure 6B:
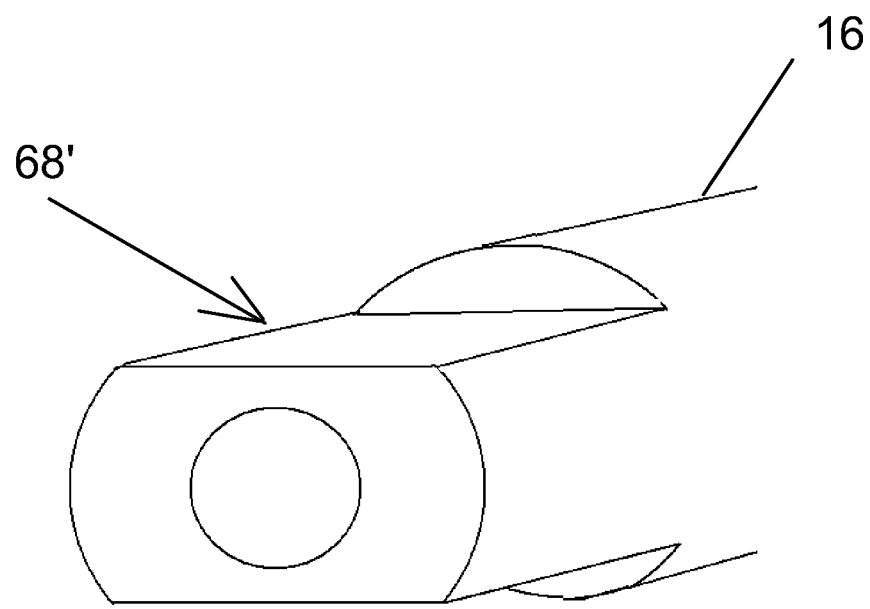
FIG. 6b illustrates a partial perspective view of the transducer of FIG. 6b.

In some embodiments, as illustrated in FIGS. 6*a* and 6*b*, the tube 16 comprises a stepped portion 68' that extends only partially around the tube. Thus, the stepped portion 68' can include one or more (e.g., 2, 3, 4, more than 4, etc.) regions of the tube 16 that are recessed or that otherwise do not extend to the outer circumference of the tube. Alternatively, as illustrated and discussed herein with reference to FIG. 6, the stepped portion 68 can extend completely around the tube.

With continued attention to the embodiment illustrated in FIGS. 6*a* and 6*b*, an end (e.g., proximal end) of the tube 16 can include, for example, oppositely oriented flattened or non-circular features along the stepped portion 68'. As noted in greater detail herein, the tube 16 can be manufactured (e.g., cast, formed, etc.) with a desired stepped portion 68'. In other embodiments, however, the features of the stepped portion 68' can be created by removing material from one or more regions of a cylindrical tube. For example, the stepped portion 68' can be created by selectively cutting, grinding and/or otherwise removing material from the tube.

As illustrated in the embodiment illustrated in FIGS. 6*a* and 6*b*, the tube 16 can comprise upper and lower flattened regions along the stepped portion 68'. In other embodiments, however, the stepped portion 68' can include fewer (e.g., one) or more (e.g., 3, 4, 5, 6, more than 6, etc.) flattened features or portions and/or other recesses (e.g., relative to the main outer diameter of the tube). Such features or recesses of the stepped portion can be continuous or discontinuous and/or may include any shape (e.g., flat, curved or rounded, irregular, fluted, undulating, etc.), as desired or required. In some embodiments, for example, the stepped portion includes a length of the tube 16 having a smaller outer diameter than the major outer diameter of the tube (e.g., the adjacent main portion of the tube). Therefore, the stepped portion can comprise a generally circular outer diameter (e.g., FIG. 6) that extends completely around the tube.

In some embodiments, the diameter or other cross-sectional dimension of the stepped portion 68*a* is 50-95% (e.g., 50-55, 55-60, 60-65, 65-70, 70-75, 75-80, 80-85, 85-90, 90-95%, percentages between the foregoing ranges, etc.) of the outer diameter 66*a* of the transducer. In other embodiments, the diameter or other cross-sectional dimension of the stepped portion 68*a* is less than 50% (e.g., 20-30, 30-40, 40-50%, percentages between the foregoing ranges, less than 20%, etc.) or greater than 95% (e.g., 95-96, 96-97, 97-98, 98-99, 99-100%, percentages between the foregoing ranges, etc.) of the outer diameter 66*a* of the transducer.

As shown in FIG. 6*a*, regardless of the exact shape and configuration of the stepped portion 68', one or more wires or other electrical conductors 28 (e.g., portions of a cable) can be advantageously secured to the outer surface of the tube. Since, in such embodiments, the outer surface of the tube 16 along the stepped portion 68' does not extend to the major outer diameter of the tube 16, the conductors 28 can be retained within the major outer diameter. As discussed herein with reference to FIG. 6, one or more components, materials and/or the like 72' can be positioned along the stepped portion 68' to match or substantially match the final major outer diameter of the stepped portion 68' to the adjacent portion (e.g., non-stepped portion) of the tube 16. Such components and/or materials 72' can comprise, without limitation, solder (e.g., silver-based solder, conductive epoxy, other flowable or malleable materials, mechanical rings and/or the like. Such components and/or materials can be at least partially electrically conductive in order to electrically couple the one or more conductors 28 positioned along the stepped portion 68' to the outer electrode of the transducer.

Figure 6C:
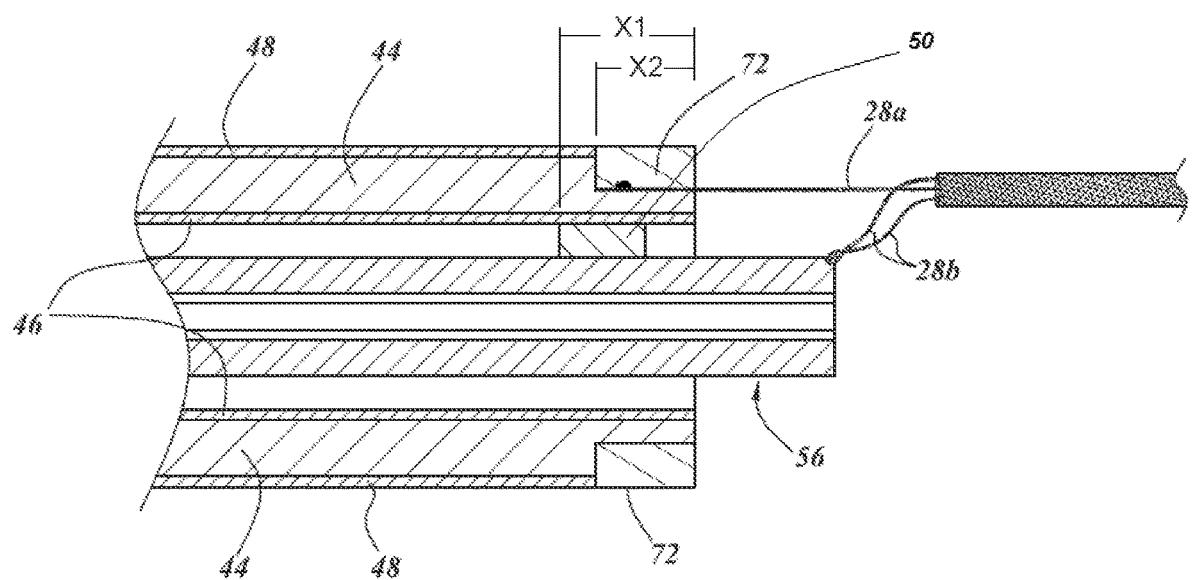
FIG. 6c illustrates a partial cross-sectional view of an ultrasound transducer according to another embodiment.

With reference to FIG. 6*c*, in some embodiments, the distal ring 72 does not extend past the innermost portion of the adjacent stand-off assembly 50 that is positioned between the backing member or post 56 and the transducer. In other words, the distance from the end of the transducer tube 44 to the proximal end of the ring 72 (designated as distance X2 in FIG. 6*c*) is less than the distance from the end of the tube to the proximal end of the stand-off assembly 50 (designated as distance X1 in FIG. 6*c*). Such a configuration can help ensure that the acoustic energy profile generated by the transducer is uniform, both radially around the circumference of the transducer and axially along the length of the transducer. In some embodiments, if X2 is equal to or greater than X1 (e.g., in other words, if the ring 72 extends proximally to the stand-off assembly 50), the manner in which the transducer is permitted to vibrate during use can be negatively impacted, thereby causing at least partial non-uniformity (e.g., radial and/or axial) of the resulting acoustic pattern generated from the transducer.

Electrical Impedance Matching

As discussed herein, the ultrasonic transducer 16 can convert input electrical energy into ultrasonic energy that is delivered radially outwardly (e.g., toward target nerve tissue or other tissue adjacent a vessel wall). In some embodiments, for ultrasonic transducers, the power factor, or conversion rate from electrical energy into generated acoustical energy, can be relatively low. Thus, a large portion of the electrical power delivered by the power supply may be lost as wasted heat. Accordingly, in one embodiment, to increase the efficiency of the ultrasound system, the electrical impedance of the electrical conductors (e.g., the one or more electrical cables 28 that electrically couple the transducer to the power supply) can be matched or substantially matched (e.g., within about 0-10%, 0.1%, 0.2%, 0.3%, 0.4%, 0.5%, 0.5-1%, 1-2%, 2-3%, 3-4%, 4-5%, 5-6%, 6-7%, 7-8%, 8-9%, 9-10%, etc.) to the electrical impedance of the ultrasound transducer 44. Thus, in some embodiments, by matching or substantially matching the impedance values of the cable and the transducer, the electrical load of the system can help reduce or minimize the electrical inefficiency of the system, while increasing or maximizing the amount of power transferred to the transducer.

Accordingly, in some embodiments, the ultrasound system 100 comprises only a single cable (e.g., coaxial cable) routed through a corresponding lumen of the catheter and electrically coupled to the transducer. The electrical cable can be selected to match or substantially match an impedance of the ultrasound transducer. For example, in some embodiments, the impedance of both the electrical cable and the ultrasound transducer is approximately 40 to 60 ohms (e.g., 50, 40-42, 42-44, 44-46, 46-48, 48-50, 50-52, 52-54, 54-56, 56-58, 58-60 ohms, etc.). In other embodiments, the impedance of the electrical cable and the ultrasound transducer can be less than 40 ohms or greater than 60 ohms, as desired or required.

Cooling Fluid Considerations

FIG. 7 schematically illustrates one embodiment of a catheter-based ultrasound system 100 having at least two fluid lumens 26a, 26b positioned within the catheter 12. As shown, each lumen 26a, 26b of the catheter is placed in fluid communication with a separate fluid transfer device (e.g., pump). Further, with reference back to FIG. 1, each lumen 26a, 26b can be in fluid communication with corresponding pumps or other fluid transfer devices (not shown) via ports 34a, 34b (e.g., a luer fittings, other standard or non-standard couplings, etc.). Accordingly, cooling fluid can be injected, infused or otherwise delivered into the vessel to transfer heat away from the transducer and/or other areas at or near the treatment site. As discussed herein, such heat transfer can protect adjacent tissue of the subject (e.g., the wall of the vessel in which the system is placed), can help maintain the transducer within a desired temperature range during use (e.g., for safety and/or performance reasons) and/or the like.

According to some embodiments, the cooling fluid that is circulated through the balloon at the distal end of the system can include, for example, saline, water and/or any other liquid or fluid. The cooling fluid can be room temperature or actively cooled (e.g., cooled relative to room temperature, body temperature, etc.), as desired or required. In some embodiments, cooling fluid is circulated through the system in such a manner so that the temperature along the interior wall of the vessel surrounding the transducer is maintained at a temperature of about 50-55° C. (e.g., 50° C., 51° C., 52° C., 53° C., 54° C., 55° C., etc.). In other embodiments, the target temperature can be below 50° C. (e.g., 30-35° C., 35-40° C., 40-45° C., 45-50° C., temperatures between the foregoing ranges, less than 30° C., etc.) or greater than 55° C. (e.g., 55-60° C., 60-65° C., 65-70° C., 70-75° C., temperatures between the foregoing ranges, greater than 75° C., etc.), as desired or required. In addition, in some embodiments, the temperature of the vessel wall is maintained within such a target range (e.g., 50-55° C., 30-75° C., etc.), while the temperature of tissue approximately 0.5 mm to 8 mm (e.g., 1 mm to 6 mm, where, in some embodiments, target tissue is located) is heated to about 60-80° C. (e.g., 60-70° C., 70-80° C., 65-75° C., etc.), 50-100° C. (e.g., 50-60° C., 60-70° C., 70-80° C., 80-90° C., 90-100° C., temperatures between the foregoing ranges, etc.), greater than 100° C., when the transducer is activated. The higher temperature at a particular distance away from the vessel wall can be due, at least in part, on the less effective cooling by the cooling fluid at those distances away from the balloon. In some embodiments, raising the temperature of nerve and/or other nerve tissue to about 60-80° C. can help perform the desired neuromodulation (e.g., ablation, necrosing, stimulation, etc.) to such tissue. A treatment protocol that accomplishes the desired heating of the targeted tissue (e.g. nerves) while maintaining adjacent vessel tissue to safe levels (e.g., to reduce the likelihood of stenosis or other damage to such tissue) can be based, either completely or in part, on empirical or experimental data.

Certain vessels (e.g., renal arteries) in which the system can be placed can have a relatively small catheter diameter. As a result, the diameter of the fluid lumens 26a, 26b located within the catheter may also need to be reduced. As the diameter of the fluid lumens 26 are decreased, the pressure required to move the cooling fluid increases (e.g., due to an increase in back pressure and head losses through the fluid lumens). As a result, in some arrangements, increased cooling fluid pressure can be required by one or more of the pumps or other fluid transfer devices in fluid communication with the system. However, if the system fluid pressure is increased to a high enough value, the increased pressure of the balloon can create one or more safety concerns. For example, the balloon itself may be susceptible to rupture or other damage. Further, the pressure created within the balloon can cause the balloon to expand to a degree that poses a risk of harm to the adjacent tissue of the subject (e.g., the artery or other vessel of the subject may rupture or otherwise be damaged). Accordingly, in some embodiments, it is desirable to regulate and limit the pressure within the balloon. For example, in some embodiments, the internal pressure of the balloon 14 is maintained at about 1.5-2 ATM (e.g., for a 6 FR catheter).

As illustrated in FIG. 7, in one embodiment, the fluid lumens 26a, 26b can include a delivery lumen 26a and a return lumen 26b for supplying and returning cooling fluid to and from, respectively, the balloon or other expandable member 14. The use of separate fluid lumens 26a, 26b can help reduce the overall internal pressure of the balloon during use, while still being able to circulate cooling fluid at a target flowrate through the balloon interior. Thus, a desired flowrate of cooling fluid can be sustained through the system without over-pressurizing the balloon 14. This is due, in part, because the vacuum created through the return lumen 26b (e.g., by one of other pumps P) helps reduce the pressure within the balloon interior accordingly. By way of example, the delivery lumen 26a can have a pressure of approximately 70 psig and the return lumen 26b can have a vacuum of 10 psig. Thus, under those circumstances, the internal pressure of the balloon is about 30 psig (e.g., (70 psig−10 psig)/2)=30 psig).

In one embodiment, the pumps P or other fluid transfer devices that are placed in fluid communication with the fluid lumens 26a, 26b comprise positive displacement pump, such as a peristaltic pump. However, in some circumstances, when the back-pressures associated with delivering the cooling fluid to the balloon is above a particular threshold, peristaltic pumps or similar positive displacement pumps are unable to deliver the necessary flowrate of cooling fluid to the balloon.

Accordingly, in some embodiments, one or more pumps P of the systems can comprise a syringe pump. A syringe pump can include a reservoir for storing a volume of cooling fluid and a movable member configured to move (e.g., slide) within an interior of the reservoir. The movement of the movable member within the corresponding reservoir exerts the necessary backpressure on the fluid (e.g., cooling fluid) stored within the reservoir and transfers the fluid through the fluid delivery lumen 26a of the catheter and into the balloon. In some embodiments, the use of such syringe pumps can provide sufficient force to achieve the required backpressure at a desired flowrate of cooling fluid. The movable members of syringe or other such pumps can be selectively moved by one or more stepper motors or other mechanical devices. In such embodiments, the stepper motor can prevent and/or minimize deflection of the movable member caused by the corresponding torques, moments and forces.

According to some embodiments, the reservoir of the syringe or other pump P in fluid communication with the fluid lumen 26a and the balloon 14 is sized and otherwise configured to store a sufficient volume of cooling fluid for an entire treatment procedure. In some embodiments, the volume of the reservoir is approximately 50 ml to 1,000 ml (e.g., 50-100, 100-200, 200-300, 300-400, 400-500, 500-600, 600-700, 700-800, 800-900, 900-1,000 ml, capacities between the foregoing, etc.). In other embodiments, the volume of the reservoir is less than 50 ml (e.g., 20-30, 30-40, 40-50 ml, volumes between the foregoing ranges, less than 20 ml) or greater than 1,000 ml (e.g., 1,000-1,100, 1,100-1,200, 1,200-1,300, 1,300-1,400, 1,400-1,500, 1,500-2,000, 2,000-3,000, 3,000-5,000 ml, volumes between the foregoing ranges, greater than 5,000 ml, etc.), as desired or required.

In one embodiment, the fluid lumens 26 can be operated simultaneously to circulate cooling fluid through the expandable members 14 during an ablation procedure. In one embodiment, the flowrate of cooling fluid through the lumens 26 can be between 30-50 ml/min (e.g., 30-40 ml/min, 40-50 ml/min, 35-45 ml/min, 40 ml/min).

IV Bag Connector

Figure 8:
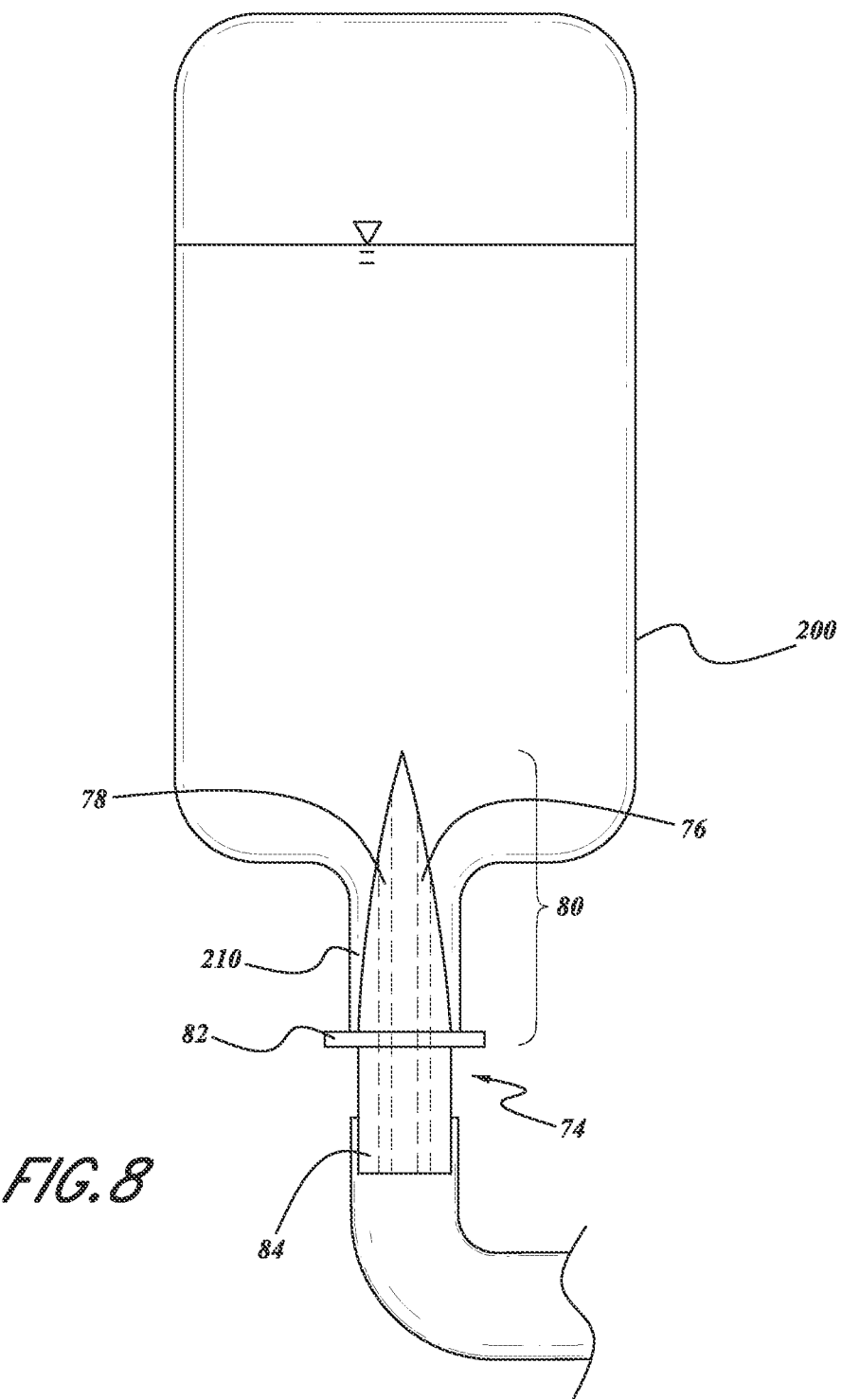
FIG. 8 illustrates an IV bag and spike or coupling inserted therein according to one embodiment.

IV bags used for the storage of cooling fluid in connection with the various systems disclosed herein can have two outlet ports (e.g., for mating to the two fluid lumens 26 of the catheter). In other embodiments, however, the IV bag 200 is constructed with only a single inlet/outlet port 210, as depicted in FIG. 8. In such embodiments, a dual lumen spike or coupling 74 can be inserted within the port 210 of the IV bag 200 to enable fluid to be transferred both to and from the bag. This can effectively turn a single-port IV bag into a dual port IV bag without redesigning the bag itself.

In some embodiments, the dual lumen spike or coupling 74 can comprise two or more lumens or passages 76, 78 that are separated from one another. Such separate passage 76, 78 can be connected to different fluid conduit or sources, as desired or required. As shown, the spike 74 can include a proximal hub 82 that is shaped, sized and otherwise configured to abut against an end of bag's port 210 (or other inlet or outlet). A proximal conduit 84 can be inserted within or otherwise placed in fluid communication with one or more fluid sources (e.g., lumen of a catheter as disclosed herein, a pump, etc.). In some embodiments, the spike can include a minimum penetration depth 80 into the IV bag to ensure adequate flow (e.g., supply and return) into and out of the bag. Such a minimum penetration depth can help prevent or reduce the likelihood of short-circuiting of fluids entering and exiting the bag 200. In some embodiments, the inner diameters of the internal lumens or passages 76, 78 of the spike or coupling 74 are approximately 0.05 to 0.125 inches (e.g., 0.05-0.06, 0.06-0.07, 0.07-0.08, 0.08-0.09, 0.09-0.1, 0.1-0.11, 0.11-0.125 inches, diameter between the foregoing, etc.) and the minimum penetration distance 80 is about 1.5 inches (e.g., 0.75, 1.0, 1.25, 1.5 inches, distances between the foregoing, less than 0.75 inches, more than 1.5 inches, 1.5-2.0 inches, 2.0-3.0 inches, more than about 3 inches, etc.).

In some embodiments, such a coupling or spike 74 can be used on an IV bag or other fluid container that is placed in fluid communication with a syringe pump of a treatment system. Thus, the IV bag can be configured to store additional fluid that will be delivered through a delivery lumen into a balloon and/or can be configured to store excess fluid being returned from the balloon via a return lumen in the catheter. Thus, the coupling 74 can be placed in fluid communication with the catheter and/or the syringe pump of the treatment system.

Vessel Diameter Detection

In some embodiments, prior to inflation of a balloon or other expandable member 14, the ultrasonic transducer 16 can be activated to measure the vessel's diameter. This can be accomplished by sending out a single (or a distinct number of) ultrasonic waves and recording the time period required for the signals to return (e.g., bounce back) to the transducer surface. Thus, in some embodiments, a control system of the system can be configured to both emit acoustic energy and detect it (e.g., at or along the outside of the transducer). By detecting the diameter of the vessel (e.g., renal artery) at a desired treatment location, the clinician can make any necessary adjustments to the procedure (e.g., what size balloon to use, how much energy should be delivered to the subject and for what time period, etc.).

Miscellaneous Concepts

In any of the embodiments disclosed herein, the system can comprise an ultrasound transducer having a variety of shapes. The transducer can be cylindrical or non-cylindrical, as desired or required. For example, in some embodiments, the transducer comprises, at least in part, an hourglass shape, a barbell shape, a convex shape or surface, a concave shape or surface and cone shape, an irregular shape and/or the like.

In some embodiments, a system comprises an array of transducers (e.g., an array comprising 2, 3, 4, 5, 6, 7, 8, 9, 10, 10-15, more than 15 transducers, etc.). In embodiments comprising 2 or more transducers (e.g., an array of transducers), one or more of the transducers can be configured to emit more or less ultrasonic energy than one or more other transducers. In some embodiments, the amount of acoustic energy that is emitted by the plurality of transducers varies (e.g., linearly, non-linearly, randomly, etc.) along a longitudinal axis of the system. In some embodiments, one or some ultrasound transducer of a system emit (or are configured to emit) greater acoustic energy in one or more directions in relation to one or more other directions.

In any of the embodiments disclosed herein, an ultrasound transducer can include differing wall thickness (e.g., along its longitudinal axis). In embodiments comprising two or more transducers, the wall thickness of one transducer is greater or less than the wall thickness of another transducer. In some embodiments, one or more transducers of a system can be independently controllable (e.g., such that power and/or frequency to one transducer can be different than power and/or frequency to another transducer, etc.). In some embodiments, two or more transducers of a system are controlled together or in unison. In one embodiment, a transducer can include an eccentric or non-uniform backing lumen or opening.

In any of the embodiments disclosed herein, the transducer comprises a varying wall thickness along at least a portion of its circumferential extent. Accordingly, rotating the transducer can alter the acoustic energy pattern emitted by the transducer and/or alter one or more other aspects of energy emission (e.g., frequency, efficiency, etc.) during use. In some embodiments, one or more regions, surfaces and/or other portions of a transducer can be at least partially masked, covered, obstructed, etc. in order to alter the acoustic energy profile of the transducer during use. For example, at least a portion of the transducer can be masked or otherwise covered by selective plating and/or etching of the electrodes along the transducer, covering a portion of the transducer, using one or more features of the balloon, etc.). Additional information regarding such masking or selective blocking of ultrasonic energy emitted from a transducer is provided in PCT Application No. PCT/US2011/025543, filed on Jan. 18, 2011 and published on Aug. 23, 2012 as PCT Publication WO 2012/112165, the entirety of which is incorporated by reference herein and made a part of this application.

In some embodiments, ultrasonic energy is directed directly within the tissue of the targeted nerve tissue (e.g., sympathetic nerves). In any of the embodiments disclosed herein, a balloon and/or other expandable structure or member can be used to at least partially expand the area or volume of tissue being treated (e.g., the renal artery, other body lumen or vessel, etc. can be radially expanded). In some embodiments, an ablation system includes a balloon (e.g., positioned at least partially around one or more transducers), but no fluid is configured to be circulated through the balloon during use. For example, in one embodiment, the balloon can be inflated with one or more gases, liquids and/or fluids (e.g., in order to expand the balloon, so that balloon contacts the adjacent wall of the targeted vessel, so that the one or more transducers of the system are radially centered or generally radially centered within the vessel, etc.), but no fluids are circulated through the balloon. Thus, the balloon can be configured to maintain an inflated or expanded state without the continuous or intermittent delivery of fluid therethrough.

In some embodiments, a catheter of the system comprises a chip (e.g., a smart catheter) and/or one or more related components or features (e.g., an identification device or reader, a transducer, etc.). Accordingly, the generator can detect which catheter is being used. Further, the system can monitor one or more aspects of a therapy or procedure using one or more metrics that are detected, such as, for example, pressure, temperature, flowrate, vessel diameter, thermal profile, presence and/or degree of spasm of a vessel, degree of narrowing of a vessel and/or the like. Such information can be used in a control scheme to regulate one or more aspects of the generator and/or other components or devices of the system (e.g., to modulate power, frequency, duration of procedure, automatic shutoff, billing, patient records or other recordkeeping, memorization of a procedure for other reasons, etc.).

Catheter Embodiments

According to some embodiments, as illustrated in FIG. 9-15, the catheter 12 comprises a guidewire lumen 13d that is generally offset relative to the centerline of the catheter. In other words, the guidewire lumen 13d of the catheter is not along the centerline or center of the catheter. Such a configuration could be incorporated into any catheter design, irrespective of size (5 French, 6 French, etc.), type (e.g., over-the-wire, rapid exchange, etc.) and/or the like. For example, such a catheter can be incorporated into any treatment system disclosed herein or variation thereof. As discussed in greater detail herein, an offset orientation of the guidewire lumen can permit other lumens (e.g., the delivery and/or return fluid lumens) 13b, 13c (see, e.g., FIGS. 16 and 17) to be enlarged given a specific catheter outer diameter.

With continued reference to FIGS. 9-15, a centering assembly 90 can be positioned adjacent or near the distal end of the catheter 12. Such a centering assembly 90 can center the guidewire GW within the interior of the balloon 14 and/or distal tip 18. Accordingly, the transducer 16 and other components (e.g., the electrically non-conductive member, backing member or post, etc.) through which the guidewire GW is routed can be advantageously centered (e.g., radially) within the balloon 14. As discussed in greater detail herein, centering of the transducer within the balloon 14 can help provide a more evenly distributed acoustic energy profile in the radial direction from the transducer 16 during use. As a result, if the balloon is centered or substantially centered within the target vessel (e.g., renal artery), acoustic energy is delivered in a uniform manner to the adjacent tissue of the subject. Thus, targeted anatomical tissues (e.g., nerves) surrounding the vessel in which the system is placed can be heated in a more predictable and consistent manner.

Figure 12:
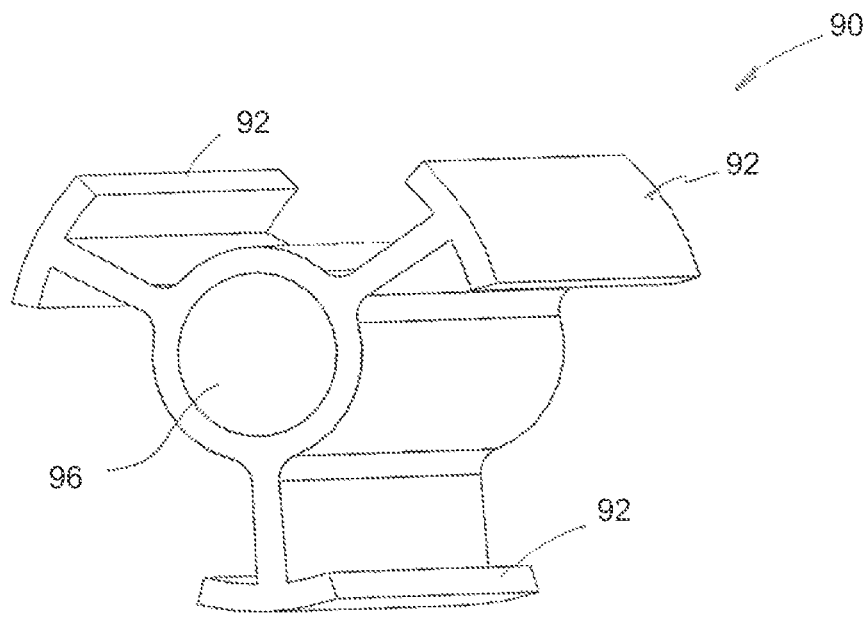
FIG. 12 illustrates one embodiment of a centering assembly.

As depicted in the perspective view of FIG. 12, the centering assembly 90 can include two or more wings 92 that extend radially outwardly from a central hub. The hub can include a central opening 96 through which a guidewide GW can pass. As discussed in greater detail herein, an electrically non-conductive tube or other member 57 (e.g., comprising polyimide) can be positioned within the central opening 96 of the centering assembly. Thus, in such embodiments, a guidewire GW can be routed through the electrically non-conductive tube 57 and the central opening 96 of the centering assembly. In any of the embodiments disclosed herein, the electrically non-conductive tube or member 57 can extend from the distal end of the catheter 12 (e.g., from a guidewire lumen of the catheter) to the distal tip 18 (e.g., an interior passage of the distal tip), through the interior of the transducer 16. According to some embodiments, the centering assembly 90 comprises three wings 92 that are evenly distributed around the circumference of the assembly 90 (e.g., spaced apart at 120° intervals). In other embodiments, however, a centering assembly can include fewer (e.g., 1, 2) or more (e.g., 4, 5, 6, more than 6, etc.) wings 92 as desired or required.

In some embodiments, the wings 92 include a curved outer surface. Such an outer surface can be generally smooth and configured to contact an adjacent surface of one or more components of the catheter system (e.g., catheter, balloon, etc.). In some embodiments, the curved outer surface of the wings 92 are shaped so as to match the adjacent interior surface of the balloon or other adjacent component of the system against which they may rest. As discussed in greater detail herein, the centering assembly 90 can be secured within a desired portion of the catheter system using one or more attachment methods or devices, such as, for example, adhesives, fasteners, hot melt connections, friction fit or press fit connections and/or the like. In some embodiments, the outer diameter of the centering assembly 90 (e.g., taken along the outermost portions of the wings 92) is identical or substantially identical (e.g., within about 0-1%, 1-2%, 2-3%, 3-4%, 4-5%, more than 5%) of the outer diameter of the catheter 12. The centering assembly can comprise one or more suitable materials (e.g., thermoplastics, metals, alloys, combinations thereof, etc.).

Figure 9:
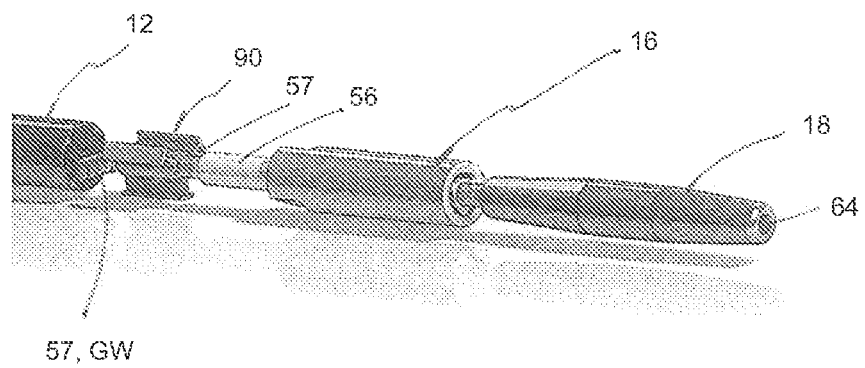
FIG. 9 illustrates a distal end of a catheter system (with the balloon hidden for clarity) according to one embodiment.
Figure 10:
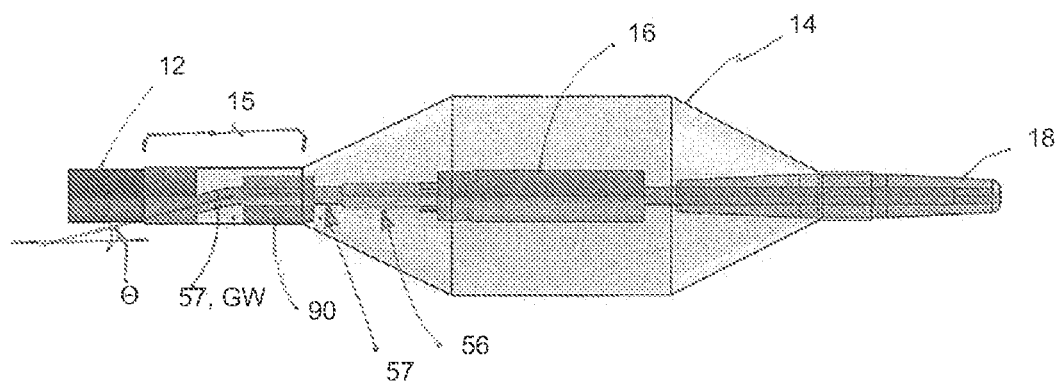
FIG. 10 illustrates a side view of the catheter system of FIG. 9.

With continued reference to FIGS. 9 and 10, the centering assembly 90 can help center the guidewire GW and the various components that are supported along the guidewire GW within the interior of the balloon 14 when the catheter system is in use. As shown, such components include the electrically non-conductive member (e.g., polyimide) 57, the ultrasound transducer 16 and the backing member or post 56 positioned between the non-conductive member and the transducer. As noted above, the electrically non-conductive member or tube 57 can extend partially or entirely through the interior of the balloon (e.g., from the distal end of the catheter 12 to the distal tip 18). The electrically non-conductive tube 57, which in some embodiments comprises polyimide and/or another thermoplastic material, can advantageously electrically shield a metal guidewire GW from other components of the system (e.g., the backing member or post 56, transducer 16, etc.). As noted above, by radially centering the transducer 16 within the balloon 14, the centering assembly 90 helps to ensure that the energy profile of the acoustic energy delivered by the transducer 16 during use is generally uniform in the radial direction (e.g., circumferentially around the transducer and balloon). In some embodiments, this provides more even and consistent heating of tissue (e.g., renal nerves) around the targeted portion of the vessel (e.g., renal artery) into which the catheter system is positioned during a treatment procedure.

Figure 13:
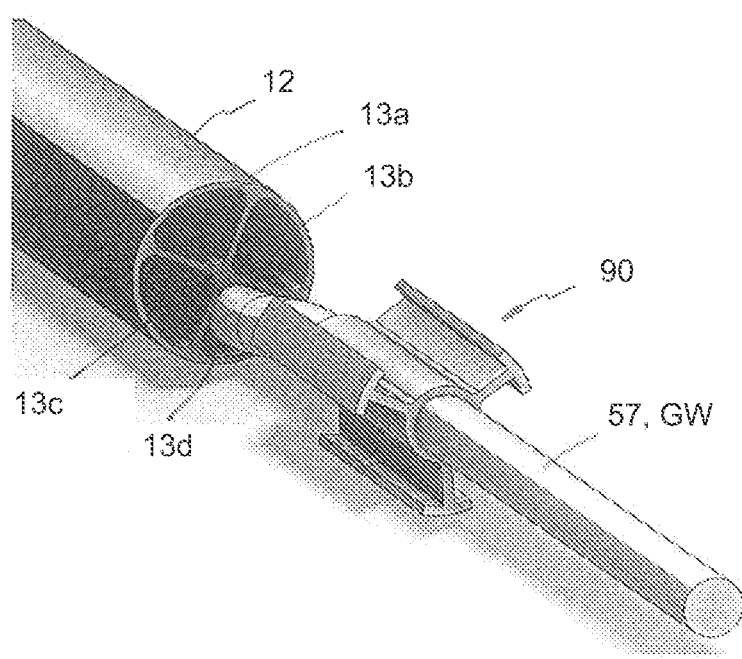
FIG. 13 illustrates the centering assembly of FIG. 12 positioned along the distal end of a catheter according to one embodiment.

As illustrated in FIGS. 9, 10 and 13, the centering assembly 90 enables the guidewire GW to transition from an radially non-centered position of the catheter 12 (e.g., from a peripheral or non-centered lumen 13d of the catheter 12) to a radially centered orientation through the assembly 90 and components distal to the assembly (e.g., a majority of the balloon 14, the distal tip 18, etc.). The guidewire GW can transition from a peripheral lumen 13d of the catheter 12 to the central opening 96 of the centering assembly 90 within a transition region along the proximal portion 15 of the balloon 14. In some embodiments, such a proximal portion 15 of the balloon comprises a generally cylindrical shape that is not configured to expand when fluid is circulated through the balloon 14. In other words, such a proximal portion 15 will maintain its outer shape during use (e.g., as cooling fluid is circulated within the balloon).

Figure 11:
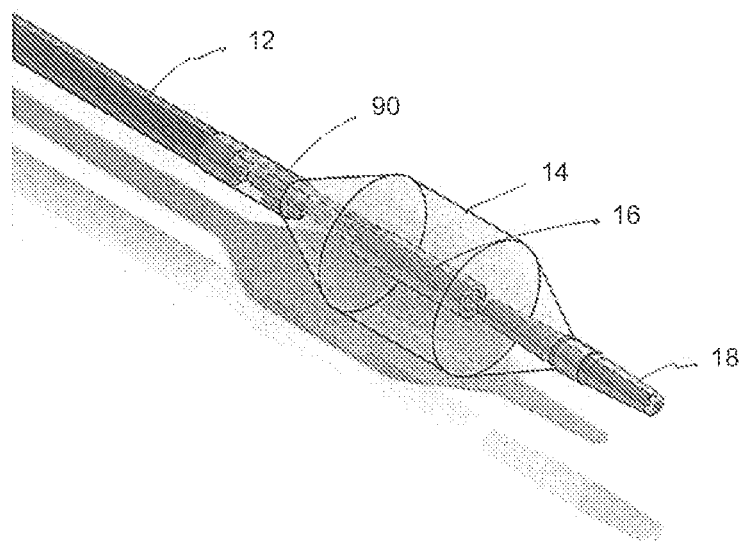
FIG. 11 illustrates a perspective view of the catheter system of FIG. 9.

In some embodiments, the entire balloon 14 (e.g., including the proximal portion 15, the main radially expandable portion, etc.) is extruded from a single material or member. In order to maintain the proximal portion 15 of the balloon from expanding during use, the proximal portion can comprise a greater thickness of the extruded material or portion relative to the distal portions of the balloon 14. For example, in some embodiments, the thickness of the proximal portion 15 of the balloon is greater than the thickness of more distally located portions (e.g., along the main, radially expandable portion of the balloon) by about 0-10%, 10-20%, 20-30%, 30-40%, 40-50%, 50-60%, 60-70%, 70-80%, 80-90%, 90-100%, 100-125%, 125-150%, 150-200%, greater than 200%, percentages between the foregoing values and/or the like. The distal portion of the balloon 14 can also include a generally cylindrical portion that is configured to maintain its shape during use (e.g., when cooling fluid is circulated through the balloon interior). As depicted in FIGS. 10 and 11, the proximal and distal portions of the balloon can be secured to the catheter 12 and the tip 18, respectively, using one or more attachment methods or devices (e.g., adhesives, pressure or friction fit connections, fasteners, etc.).

According to some embodiments, in order to transition from a peripheral lumen 13d of the catheter 12 to the central opening 96 of the centering assembly 90, the guidewire GW is angled through a portion of the catheter system (e.g., between the distal end of the catheter 12 and the proximal end of the centering assembly 90). For example, as illustrated in FIG. 10, the guidewire GW can be angled within the proximal, cylindrical portion 15 of the balloon 14 at angle Θ, which, in some embodiments, is about 0-40° (e.g., about 0-5°, 5-10°, 10-15°, 15-20°, 20-25°, 25-30°, 30-35°, 35-40°, angles between the foregoing, etc.). However, in other embodiments, the angle Θ is greater than about 40° (e.g., about 40-50°, 50-60°, greater than 60°), as desired or required.

Figure 14:
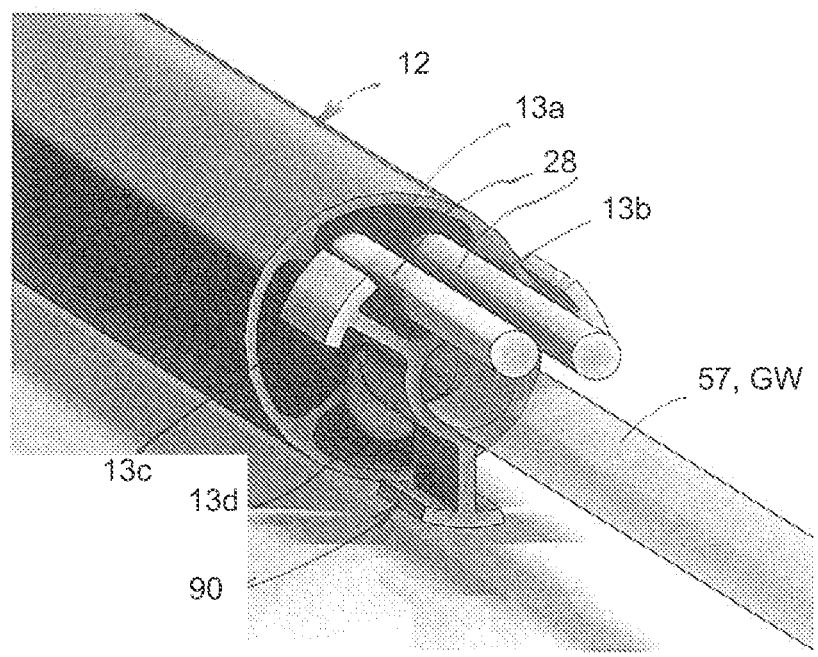
FIGS. 14 and 15 illustrate different perspective views of a distal end of a catheter assembly according to one embodiment comprising a centering assembly.
Figure 15:
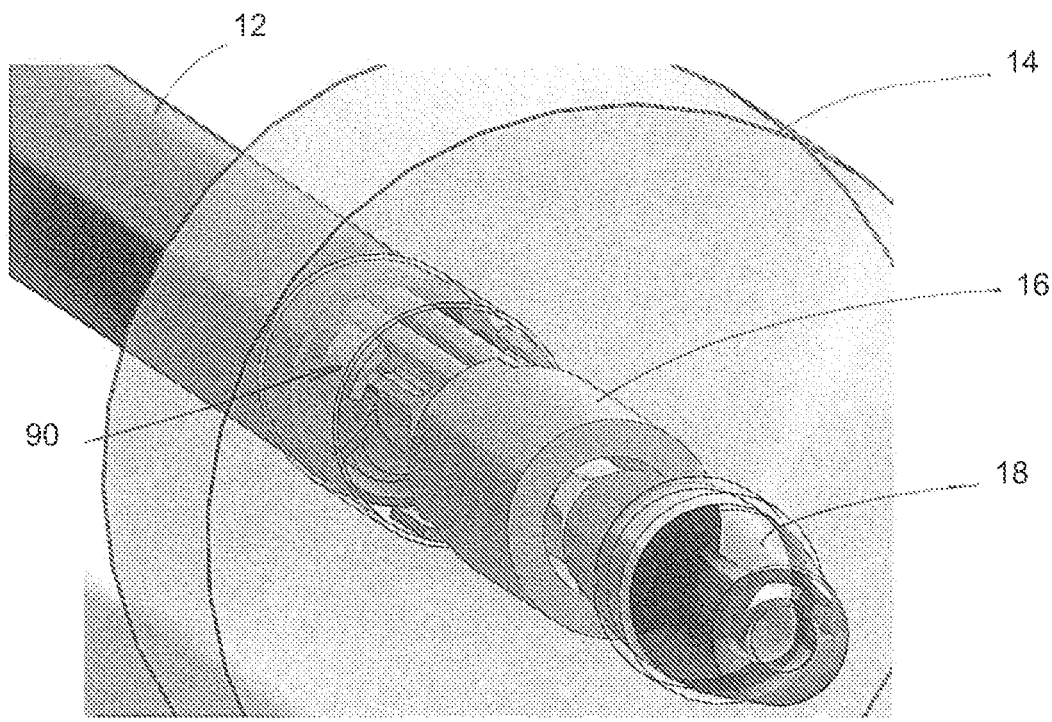

As illustrated in FIG. 14, in addition to the guidewire lumen 13d discussed above, the catheter 12 can comprise one or more other lumens 13a, 13b, 13c. For example, in the depicted embodiment, the catheter 12 includes a lumen 13a for routing one or more electrical conductors (e.g., coaxial cables) 28 to the distal end of the system. As discussed in greater detail herein, such cables or other electrical conductors 28 can electrically couple the inner and outer electrodes of the transducer 16 to a generator. In addition, the catheter can include one or more fluid lumens 13b, 13c that are shaped, sized and otherwise configured to transfer cooling fluid (e.g., water, saline, other liquid or gas, etc.) to and/or from the interior of the balloon 14. For example, in some embodiments, the catheter comprises separate fluid delivery 13b and fluid return 13c lumens that are in fluid communication with the balloon interior.

According to some embodiments, the catheter 12 does not include any central lumens. In other words, all of the lumens 13a-13d of the catheter can be located away from the radial centerline of the catheter (e.g., along the periphery of the catheter, locations between the radial centerline of the catheter and the periphery, etc.). Such a configuration can allow the various lumens 13a-13d to be more tightly packed within the cross-sectional area of the catheter. For example, in some embodiments, a certain minimum flowrate of cooling fluid is required or desired through the balloon 14 during use. For instance, the minimum required or desired flowrate for such a cooling fluid can be about 40 ml/min (e.g., about 40-42, 42-45, 45-50, 50-60 ml/min, flowrates between the foregoing, greater than 50 ml/min, etc.).

Accordingly, in order to transfer cooling fluid to and/or from the interior balloon at a desired or required flowrate while preventing over-pressurization of the balloon, the fluid lumens 13b, 13c of the catheter 12 can comprise a minimum cross sectional size. Such a design can also help ensure that the delivery of fluid through the catheter lumens occurs at acceptable flowrates, velocities, headlosses and/or other fluid dynamic considerations. In some embodiments, for example, the cross-sectional area of each of the fluid lumens 13b, 13c of the catheter 12 is about 0.00005 to 0.00012 square inches (e.g., 0.00005 to 0.00006, 0.00006 to 0.00007, 0.00007 to 0.00008, 0.00008 to 0.00009, 0.00009 to 0.00010, 0.00010 to 0.00011, 0.00011 to 0.00012 square inches, areas between the foregoing, etc.), less than about 0.00005 square inches, more than about 0.00012 square inches for a 6 French catheter, and about 0.00003 to 0.00010 square inches (e.g., 0.00003 to 0.00004, 0.00004 to 0.00005, 0.00005 to 0.00006, 0.00006 to 0.00007, 0.00007 to 0.00008, 0.00008 to 0.00009, 0.00009 to 0.00010 square inches, areas between the foregoing, etc.), less than about 0.00003 square inches, more than about 0.00010 square inches for a 5 French catheter. Thus, by eliminating a central lumen (e.g., a central guidewire lumen) within the catheter 12, the size of one or more of the other lumens (e.g., the fluid lumens 13b, 13c) can be advantageously increased. This can be particularly helpful smaller diameter catheters, such as, for example, 5 French catheters, which may be advanced through the subject's anatomy using radial access.

Figure 16:
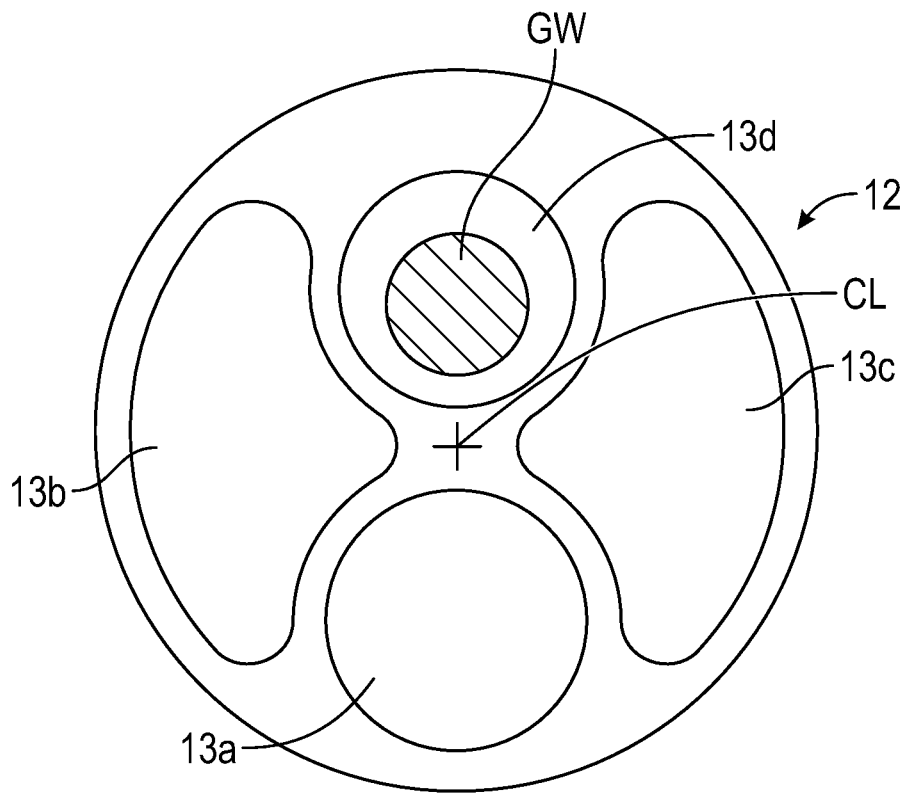
FIG. 16 illustrates a cross-sectional view of a catheter according to one embodiment.

One embodiment of a cross-sectional area of a catheter 12 is illustrated in FIG. 16. As shown, the catheter can include four lumens 13a-13d, each of which is oriented away from the radial centerline CL of the catheter. The lumens 13a, 13d can comprise a circular or oval shape. However, the shape of one or more of the lumens can be non-circular, as desired or required. For example, in the depicted embodiment, the catheter comprises two fluid lumens 13b, 13c having a generally irregular shape (e.g., having one or more curved portions that generally surround and fit around the adjacent circular lumens 13a, 13d). Thus, as shown, the cross-sectional size of each of the fluid lumens 13b, 13c can be advantageously increased (e.g., relative to a circular or oval lumen). In addition, such an orientation allows for the various lumens 13a-13d of a catheter to be more tightly packed. For example, in some embodiments, the combined cross-sectional shape of the lumens 13a-13d is approximately 60-90% (e.g., 60-65%, 65-70%, 70-75%, 75-80%, 80-85%, 85-90%, percentages between the foregoing values, etc.) of the entire cross-sectional area of the catheter. In some embodiments, none of the lumens 13a-13d comprises a circular or oval shape. For example, all of the lumens can include a generally irregular shape, such as the shape of the fluid lumens 13b, 13c of FIG. 16.

As noted above, such a strategic orientation of the lumens (e.g., in which the amount of non-lumen space is reduced or minimized) can permit the use of smaller catheter sizes for a particular treatment procedure. For example, the ability to include larger, non-circular fluid lumens 13b, 13c can allow for the necessary delivery of cooling fluid to and from the balloon interior by using a smaller catheter size (e.g., 5 French, 6 French, etc.). This can be particularly helpful when advancing the catheter through smaller diameter portions of the subject's vasculature (e.g., via radial access).

According to some embodiments, the cross-sectional orientation of the various lumens 13a-13d can be maintained throughout the entire length of the catheter. For example, the lumens illustrated in FIG. 16 can extend from a proximal to a distal end of the catheter 12. Such a catheter can include a traditional over-the-wire design in which the entire length of the catheter is routed over a guidewire GW during the advancement of the catheter to the target anatomical site.

However, in other embodiments, as noted herein, the catheter can include a rapid-exchange design in which the catheter comprises a guidewire lumen 13d only partially along its length. For example, the guidewire lumen 13d can extend only through the distal-most portion of the catheter (e.g., along a length immediately proximal to the balloon). In some embodiments, the catheter comprises an interior guidewire lumen 13d only along the last 5 to 30 cm (e.g., 5-6, 6-8, 8-10, 10-12, 12-14, 14-16, 16-18, 18-20, 20-25, 25-30 cm, lengths between the foregoing, etc.) of the catheter's distal end. In some embodiments, the catheter comprises a guidewire lumen 13d only along 0-30% (e.g., 0-5%, 5-10%, 10-15%, 15-20%, 20-25%, 25-30%, percentages between the foregoing, etc.) of its length (e.g., the distal end of catheter).

Figure 17:
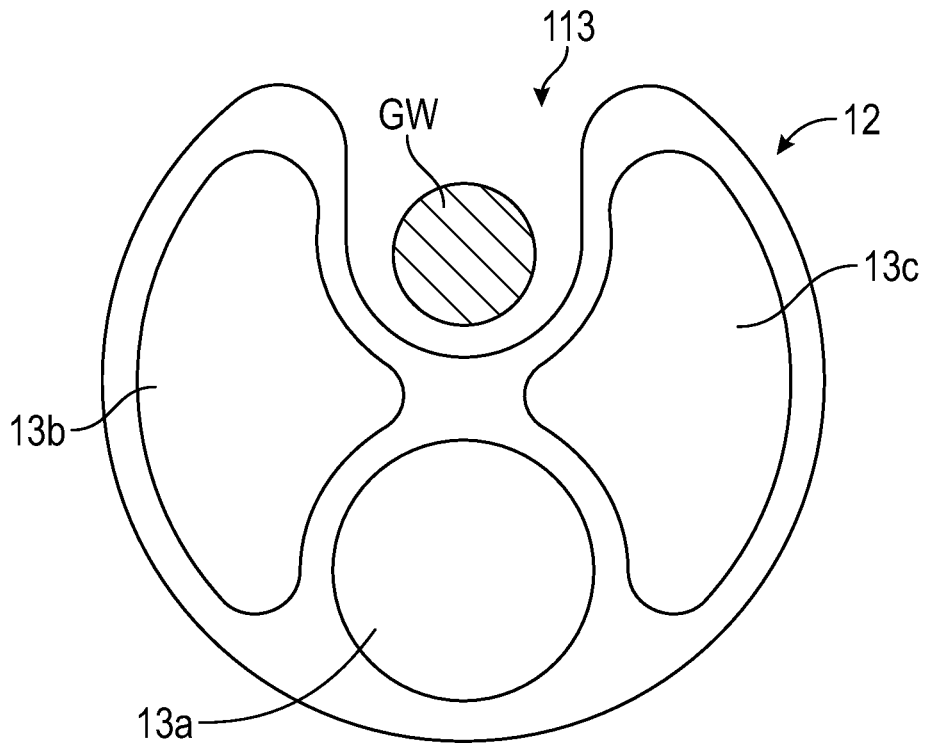
FIG. 17 illustrates a cross-sectional view of a catheter according to another embodiment.
Figure 18:
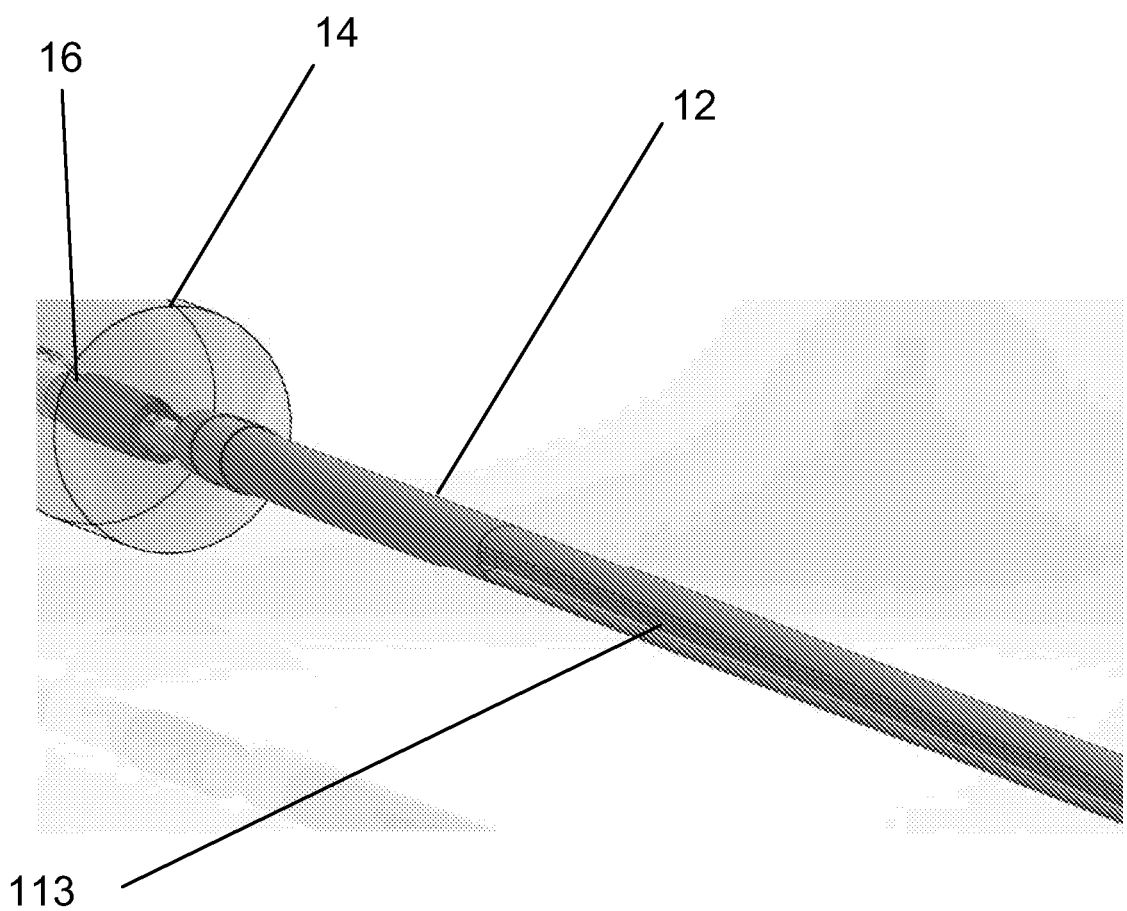
FIG. 18 illustrates a partial perspective view of one embodiment of a catheter comprising an external groove or recess.

According to some embodiments, for catheters 12 that include such a rapid-exchange design, a proximal portion of the catheter does not include an interior guidewire lumen. A cross-sectional area along a proximal end of one embodiment of such a catheter 12 is illustrated in FIG. 17. As shown, the catheter 12 can include a groove, slot, recess or other opening 113 that is sized, shaped and otherwise configured to accommodate an adjacent guidewire GW. Such a groove or recess 113 can advantageously permit the guidewire to be positioned therein (e.g., at least through the length of the proximal length of the catheter that does not include an interior guidewire lumen). One embodiment of a catheter 12 comprising such a groove or recess 113 is illustrated in the partial perspective view of FIG. 18. As shown in FIG. 18 and noted above, such a groove or recess 113 can extend from the proximal end of the catheter 12 to a location proximal to the distal end of the catheter 12 and the balloon 14.

Such a configuration comprising a groove or recess 113 can facilitate positioning the catheter 12 and the guidewire through a smaller diameter sheath or guiding catheter during a treatment procedure. As noted herein, the use of smaller catheters, sheaths and other components can be helpful when using a radial access approach. For example, in such a rapid exchange catheter design, the guidewire can be nestled or otherwise positioned within the groove or recess 113 of the catheter along the entire length or substantially the entire length of the catheter. In some embodiments, for the entire length of the catheter 12, the guidewire is configured to be located either within the groove or recess 113 (e.g., along the proximal end of the catheter) or within the guidewire lumen of the catheter 12 (e.g., along the most distal end of the catheter). Thus, in such embodiments, the guidewire does not need to extend along the outer circular area formed by the catheter. This can advantageously permit the catheter and guidewire to be positioned within a smaller delivery catheter or sheath. As noted herein, such a smaller delivery catheter or sheath can permit the device to be delivered to a target vessel of the subject through smaller vasculature or access points of the subject (e.g., radial access). Relatedly, such a configuration can allow the system to include a larger main catheter, which can provide the cross-sectional areas of one or more of the internal lumens of the main catheter to be maximized or increased. Accordingly, the area of the fluid lumens (e.g., the fluid delivery lumen, the fluid return lumen, etc.) can be increased (e.g., relative to a rapid exchange catheter that does not include a groove or recess 113).

In some embodiments, for example, such a design can facilitate the passage of cooling fluid through the catheter (e.g., reduced head loss), thereby improving circulation of cooling fluid through a balloon located along the distal end of the main catheter. These features can be especially advantageous when the guidewire lumen along the distal end of the catheter (e.g., distal to the groove or recess 113) is eccentrically-located in the catheter. For example, in such embodiments, the orientation of the eccentrically-located guidewire lumen further helps to increase the area of one or more other lumens of the catheter (e.g., fluid lumens).

Further, in some embodiments for example, the inclusion of a groove or recess 113 along the outside of the catheter can allow the ablation and/or other intravascular procedure to be performed using a shorter guidewire. This may, in certain circumstances, allow a procedure to be completed with fewer personnel (e.g., the surgeon or other physician may be able to handle the procedure by himself or herself and/or with fewer assistants).

To assist in the description of the disclosed embodiments, words such as upward, upper, bottom, downward, lower, rear, front, vertical, horizontal, upstream, downstream have been used above to describe different embodiments and/or the accompanying figures. It will be appreciated, however, that the different embodiments, whether illustrated or not, can be located and oriented in a variety of desired positions.

Although several embodiments and examples are disclosed herein, the present application extends beyond the specifically disclosed embodiments to other alternative embodiments and/or uses of the inventions and modifications and equivalents thereof. It is also contemplated that various combinations or subcombinations of the specific features and aspects of the embodiments may be made and still fall within the scope of the inventions. Accordingly, it should be understood that various features and aspects of the disclosed embodiments can be combine with or substituted for one another in order to form varying modes of the disclosed inventions. Thus, it is intended that the scope of the present inventions herein disclosed should not be limited by the particular disclosed embodiments described above, but should be determined only by a fair reading of the claims that follow.

While the inventions are susceptible to various modifications, and alternative forms, specific examples thereof have been shown in the drawings and are herein described in detail. It should be understood, however, that the inventions are not to be limited to the particular forms or methods disclosed, but, to the contrary, the inventions are to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "advancing a catheter intraluminally" or "activating a transducer" include "instructing advancing a catheter intraluminally" and "instructing activating a transducer." The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 mm" includes "10 mm" Terms or phrases preceded by a term such as "substantially" include the recited term or phrase. For example, "substantially parallel" includes "parallel."

What is claimed is:

1. A method of intraluminally ablating nerve tissue using an ultrasound-based ablation system, the method comprising:
    advancing a catheter of the ablation system within a blood vessel to a target anatomical location of a subject, wherein the ablation system comprises a balloon positioned at a distal end of the catheter, an interior of the balloon being defined by a balloon wall and in fluid communication with at least one fluid delivery lumen and at least one fluid return lumen of the catheter, wherein an ultrasound transducer is positioned within the interior of the balloon and constructed as a cylindrical tube having an inner surface and an outer surface, wherein the cylindrical tube is characterized by a length and a circumference that is substantially uniform along the length;
    circulating cooling fluid through the interior of the balloon at a flowrate in a range of 10-25 ml/min by transferring the cooling fluid from a first syringe pump through the at least one fluid delivery lumen to the interior of the balloon and transferring cooling fluid away from the interior of the balloon through the at least one fluid return lumen to a second syringe pump, wherein the inner surface and the outer surface are substantially parallel with the balloon wall; and
    activating the ultrasound transducer positioned within the balloon to ablate nerve tissue in an annular region 1 mm to 6 mm from an inner lumen of the blood vessel by simultaneously and uniformly emitting acoustic energy radially around the circumference of the cylindrical tube and along the length of the cylindrical tube to target the annular region that surrounds the outer surface of the cylindrical tube while protecting an inner wall of the blood vessel using the cooling fluid, wherein the cooling fluid is circulated adjacent to the ultrasound transducer within the balloon when the ultrasound transducer is activated,
    wherein the first syringe pump comprises a reservoir for storing a volume of the cooling fluid and a movable member configured to move within the reservoir in order to transfer the cooling fluid through the at least one fluid delivery lumen to the interior of the balloon.

2. The method of claim 1, wherein the movable member is coupled to a motor for selectively advancing the movable member relative to the reservoir and wherein the blood vessel is protected from stenosis while activating the ultrasound transducer.

3. The method of claim 1, wherein: circulating the cooling fluid through the interior of the balloon inflates the balloon, and the cooling fluid is room temperature, and the cooling fluid is circulated at the flowrate to maintain a temperature along the inner lumen of the blood vessel at 50° C. or lower.

4. The method of claim 1, further comprising supplying electrical power to the ultrasound transducer via an electrical cable electrically coupled to the ultrasound transducer and a generator.

5. The method of claim 4, wherein an impedance of the electrical cable matches an impedance of the ultrasound transducer.

6. The method of claim 5, wherein the impedance of the electrical cable and the ultrasound transducer is approximately 40 to 60 ohms.

7. The method of claim 4, further comprising electrically coupling a connector of the electrical cable to an electrode of the ultrasound transducer without physically attaching the connector to an outer surface of the ultrasound transducer.

8. The method of claim 1, further comprising preventing the cooling fluid from entering a guidewire lumen when the cooling fluid is circulated adjacent the ultrasound transducer within the balloon.

9. The method of claim 1, further comprising aligning a central opening of the ultrasound transducer with an internal guidewire passage of a distal tip of the catheter.

10. The method of claim 1, further comprising centering the ultrasound transducer within the balloon to provide an evenly distributed acoustic energy profile in a radial direction from the ultrasound transducer.

11. The method of claim 1, further comprising reflecting ultrasonic energy generated along an interior surface of the ultrasound transducer radially outwardly from the ultrasound transducer.

12. The method of claim 1, wherein, when circulating the cooling fluid, the flowrate is sustained through the ablation system without over-pressurizing the balloon.

13. The method of claim 1, wherein, when circulating the cooling fluid, an internal pressure in the balloon is sustained.

14. The method of claim 13, wherein the internal pressure is 30 psig.

15. The method of claim 1, wherein the at least one fluid delivery lumen and the at least one fluid return lumen are operated simultaneously to circulate the cooling fluid through the balloon at the flowrate when the ultrasound transducer is activated.

16. The method of claim 1, wherein the catheter is a 5 French or 6 French catheter.

17. The method of claim 1, wherein the at least one fluid delivery lumen and the at least one fluid return lumen each have a cross-sectional area greater than 0.00012 square inches.

18. The method of claim 1, wherein the first syringe pump is coupled to the at least one fluid delivery lumen and the second syringe pump is coupled to the at least one fluid return lumen, wherein the second syringe pump is configured to create a vacuum through the at least one fluid return lumen.

19. The method of claim 1, wherein the first syringe pump and the second syringe pump provide force to achieve a required back pressure at the flowrate of the cooling fluid.

20. The method of claim 1, wherein the second syringe pump comprises a second reservoir and a second movable member.

21. The method of claim 20, wherein the movable member and the second movable member are configured to be selectively moved by one or more stepper motors.

22. The method of claim 1, wherein the balloon is a compliant balloon.

23. The method of claim 1, further comprising actively cooling the cooling fluid.

24. The method of claim 1, wherein the cooling fluid is circulated at the flowrate to maintain a temperature along the inner lumen of the blood vessel at 30° C. or lower.

25. The method of claim 1, wherein the cooling fluid is circulated at the flowrate to maintain a temperature along the inner lumen of the blood vessel at 30° C. or lower, while the temperature of the nerve tissue from about 1 mm to about 6 mm is maintained between about 50° C.-100° C.

26. A method of ablating nerve tissue using an ultrasound-based ablation system, the method comprising:
   advancing a catheter of the ablation system within a blood vessel lumen to a target anatomical location of a subject, wherein the catheter is 6 French or 5 French, wherein the ablation system comprises a balloon positioned at a distal end of the catheter, an interior of the balloon being defined by a balloon wall and in fluid communication with at least one fluid delivery lumen and at least one fluid return lumen of the catheter, wherein an ultrasound transducer is positioned within the interior of the balloon and constructed as a cylindrical tube having an inner surface and an outer surface, wherein the cylindrical tube is characterized by a length and a circumference that is substantially uniform along the length;
   circulating cooling fluid through the interior of the balloon at a flowrate in a range of 10-25 ml/min by transferring the cooling fluid from a first syringe pump through the at least one fluid delivery lumen to the interior of the balloon and transferring cooling fluid away from the interior of the balloon through the at least one fluid return lumen to a second syringe pump, wherein the inner surface and the outer surface are substantially parallel with the balloon wall; and
   activating the ultrasound transducer positioned within the balloon to neuromodulate nerve tissue in an annular region about 1 mm to 6 mm from an interior of the blood vessel lumen by simultaneously and uniformly emitting acoustic energy radially around the circumference of the cylindrical tube and along the length of the cylindrical tube to target the annular region that surrounds the outer surface of the cylindrical tube while protecting an inner wall of the blood vessel lumen, wherein the cooling fluid is circulated adjacent to the ultrasound transducer within the balloon when the ultrasound transducer is activated,
   wherein the first syringe pump comprises a reservoir for storing a volume of the cooling fluid and a movable member configured to move within the reservoir in order to transfer the cooling fluid through the at least one fluid delivery lumen to the interior of the balloon, and
   wherein circulating the cooling fluid through the interior of the balloon maintains a desired temperature threshold along a wall of the target anatomical location of the subject while allowing a higher temperature profile a particular distance radially away from the wall of the target anatomical location.

27. A method of ablating renal nerves using an ultrasound-based ablation system, the method comprising:
   advancing a catheter of the ablation system within a renal artery, wherein the ablation system comprises a balloon positioned at a distal end of the catheter, an interior of the balloon being defined by a balloon wall and in fluid communication with at least one fluid delivery lumen and at least one fluid return lumen of the catheter, wherein an ultrasound transducer is positioned within the interior of the balloon and constructed as a cylindrical tube having an inner surface and an outer surface, wherein the cylindrical tube is characterized by a length and a circumference that is substantially uniform along the length;
   circulating cooling fluid through the interior of the balloon at a flowrate in a range of 10-25 ml/min by transferring the cooling fluid from a first syringe pump through the at least one fluid delivery lumen to the interior of the balloon and transferring cooling fluid away from the interior of the balloon through the at least one fluid return lumen to a second syringe pump, wherein the inner surface and the outer surface are substantially parallel with the balloon wall; and
   activating the ultrasound transducer positioned within the balloon to ablate nerve tissue in an annular region about 1 mm to 6 mm from an inner lumen of the renal artery by simultaneously and uniformly emitting acoustic energy radially around the circumference of the cylindrical tube and along the length of the cylindrical tube to target the annular region that surrounds the outer surface of the cylindrical tube while protecting an inner arterial wall using the cooling fluid, wherein the cooling fluid is circulated adjacent to the ultrasound transducer within the balloon when the ultrasound transducer is activated,
   wherein the first syringe pump comprises a reservoir for storing a volume of the cooling fluid and a movable member configured to move within the reservoir in order to transfer the cooling fluid through the at least one fluid delivery lumen to the interior of the balloon.

28. The method of claim 27, wherein advancing the catheter comprises advancing the catheter such that the ultrasound transducer is positioned within the renal artery of a subject, and
   wherein activating the ultrasound transducer comprises activating the ultrasound transducer to ablate renal nerve tissue 1 mm to 6 mm away from the inner lumen of the renal artery while protecting the renal artery from stenosis.

29. The method of claim 27, wherein the cooling fluid stored in the reservoir of the first syringe pump is room temperature.

30. The method of claim 27, wherein activating the ultrasound transducer positioned within the balloon to ablate nerve tissue comprises activating the ultrasound transducer for 7 seconds.

31. A method of ablating renal nerves using an ultrasound-based ablation system, the method comprising:

advancing a catheter of the ablation system within a renal artery, wherein the ablation system comprises a balloon positioned at a distal end of the catheter, an interior of the balloon being defined by a balloon wall and in fluid communication with at least one fluid delivery lumen and at least one fluid return lumen of the catheter, wherein an ultrasound transducer is positioned within the interior of the balloon and constructed as a cylindrical tube having an inner surface and an outer surface, wherein the cylindrical tube is characterized by a length and a circumference that is substantially uniform along the length;

circulating cooling fluid at a flowrate of 10-25 ml/min through the interior of the balloon by transferring the cooling fluid from a first syringe pump through the at least one fluid delivery lumen to the interior of the balloon and transferring cooling fluid away from the interior of the balloon through the at least one fluid return lumen to a second syringe pump, wherein the inner surface and the outer surface are substantially parallel with the balloon wall; and activating the ultrasound transducer positioned within the balloon to ablate nerve tissue in an annular region from an inner lumen of the renal artery by simultaneously and uniformly emitting acoustic energy radially around the circumference of the cylindrical tube and along the length of the cylindrical tube to target the annular region that surrounds the outer surface of the cylindrical tube while protecting an inner arterial wall using the cooling fluid, wherein the cooling fluid is circulated adjacent to the ultrasound transducer within the balloon when the ultrasound transducer is activated at the flowrate, wherein the first syringe pump comprises a reservoir for storing a volume of the cooling fluid and a movable member configured to move within the reservoir in order to transfer the cooling fluid through the at least one fluid delivery lumen to the interior of the balloon.

32. The method of claim 31, wherein the flowrate is sufficient to protect the renal artery from stenosis.

33. The method of claim 31, wherein the ultrasound transducer is activated to ablate the nerve tissue for 7 seconds.

34. The method of claim 31, wherein the ablation of the nerve tissue is sufficient to treat a patient's hypertension.

35. The method of claim 31, wherein the catheter is 6 French or 5 French.

36. The method of claim 31, wherein, when circulating the cooling fluid, the flowrate is sustained through the ablation system without over-pressurizing the balloon.

37. The method of claim 31, wherein the cooling fluid is room temperature.

38. The method of claim 31, wherein the catheter is 6 French, and wherein, when circulating the cooling fluid, an internal pressure in the balloon is sustained at 30 psig.

* * * * *